United States Patent
Kamatani et al.

(10) Patent No.: US 9,882,148 B2
(45) Date of Patent: Jan. 30, 2018

(54) ORGANIC COMPOUND, FIELD ELEMENT, ORGANIC LIGHT-EMITTING ELEMENT, DISPLAY APPARATUS, IMAGE INFORMATION-PROCESSING APPARATUS, LIGHTING APPARATUS, IMAGE-FORMING APPARATUS, AND EXPOSURE APPARATUS

(71) Applicant: CANON KABUSHIKI KAISHA, Tokyo (JP)

(72) Inventors: Jun Kamatani, Tokyo (JP); Tetsuya Kosuge, Yokohama (JP); Masumi Itabashi, Yamato (JP); Yosuke Nishide, Kawasaki (JP); Hirokazu Miyashita, Tokyo (JP); Naoki Yamada, Inagi (JP); Tetsuo Takahashi, Kawasaki (JP); Satoru Shiobara, Funabashi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/321,067

(22) PCT Filed: Jun. 22, 2015

(86) PCT No.: PCT/JP2015/003106
§ 371 (c)(1),
(2) Date: Dec. 21, 2016

(87) PCT Pub. No.: WO2015/198579
PCT Pub. Date: Dec. 30, 2015

(65) Prior Publication Data
US 2017/0155059 A1   Jun. 1, 2017

(30) Foreign Application Priority Data

Jun. 27, 2014  (JP) .................................. 2014-133280
Jan. 21, 2015  (JP) .................................. 2015-009743

(51) Int. Cl.
| | | |
|---|---|---|
| C07D 235/20 | (2006.01) | |
| H01L 51/00 | (2006.01) | |
| H01L 27/32 | (2006.01) | |
| H01L 29/786 | (2006.01) | |
| H01L 29/24 | (2006.01) | |
| F21V 29/70 | (2015.01) | |
| H05B 33/08 | (2006.01) | |
| G09G 3/3208 | (2016.01) | |

(Continued)

(52) U.S. Cl.
CPC ........ *H01L 51/0072* (2013.01); *C07D 235/20* (2013.01); *F21V 29/70* (2015.01); *G03G 15/04054* (2013.01); *G09G 3/3208* (2013.01); *H01L 27/322* (2013.01); *H01L 27/3244* (2013.01); *H01L 29/24* (2013.01); *H01L 29/7869* (2013.01); *H05B 33/0896* (2013.01); *F21Y 2115/15* (2016.08); *G03G 2215/0409* (2013.01); *H01L 51/504* (2013.01); *H01L 51/5092* (2013.01)

(58) Field of Classification Search
CPC ............ H01L 51/0072; H05B 33/0896; C07D 235/20
See application file for complete search history.

(56) References Cited

FOREIGN PATENT DOCUMENTS

| JP | 2002-100482 A | 4/2002 |
|---|---|---|
| JP | 2003-068468 A | 3/2003 |

(Continued)

OTHER PUBLICATIONS

Jean Bourson—Action of bases on 1,3-diphenyl benzimidazolium salts; Bulletin de la Societe Chimique de France, No. 10, pp. 3541-3547 (1971).

Farman Ullah, et al.—Annulated N-Heterocyclic Carbenes: 1,3-Ditolylphenanthreno[9,10-d]imidazol-2-ylidene and Transition Metal Complexes Thereof; Organometallics, vol. 28, No. 8, pp. 2441-2449 (2009).

F. Ekkehardt Hahn, et al.—N,N'-Bis(2,2-dimethylpropyl)benzimidazolin-2-ylidene: A Stable Nucleophilic Carbene Derived from Benzimidazole; Chem. Eur. J., vol. 5, No. 6, pp. 1931-1935 (1999).

(Continued)

*Primary Examiner* — Golam M M Shameem
(74) *Attorney, Agent, or Firm* — Canon U.S.A. Inc., IP Division

(57) ABSTRACT

A bibenzo[d]imidazolidene compound inert to oxygen is provided. A 1,1',3,3'-tetraphenyl-2,2'-bibenzo[d]imidazolidene compound is represented by general formula (1). In formula (1), $R_1$ to $R_{28}$ are each independently selected from a hydrogen atom and a substituent. The substituent is any of a halogen atom, an alkyl group containing 1 or more and 8 or less carbon atoms, and a substituted or unsubstituted aryl group. At least one of $R_1$ to $R_{28}$ is the substituent.

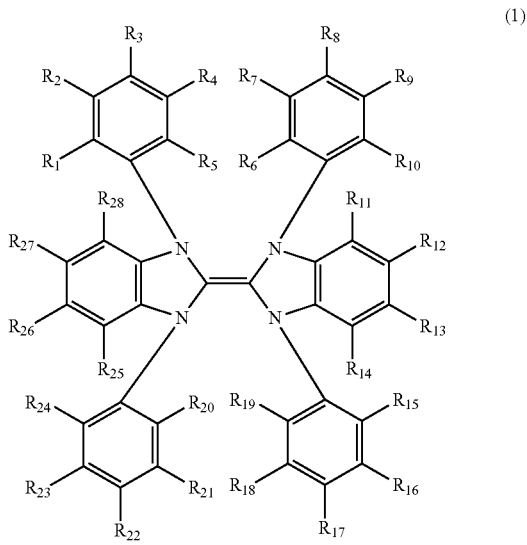

18 Claims, 5 Drawing Sheets

(51) Int. Cl.
    *G03G 15/04*     (2006.01)
    *H01L 51/50*     (2006.01)
    *F21Y 115/15*     (2016.01)

(56) References Cited

FOREIGN PATENT DOCUMENTS

| | | |
|---|---|---|
| JP | 2012-527089 A | 11/2012 |
| JP | 2015-115330 A | 6/2015 |
| JP | 2015-115331 A | 6/2015 |

OTHER PUBLICATIONS

D. Vasudevan, et al.—Electroreduction of oxygen in aprotic media; Journal of Electroanalytical Chemistry, vol. 192, pp. 69-74, Mar. 1995.

Hasan Kucukbay, et al.—L Farmaco; Synthesis, antibacterial and antifungal activities of electron-rich olefins derived benzimidazole compounds, vol. 58, pp. 431-437, Feb. 2003.

Yannick Borguet, et al., "Ruthenium catalysts bearing a benzimidazolylidene ligand for the metathetical ring-closure of tetrasubstituted cycloolefins," Dalton Transactions, An international journal of inorganic chemistry, Jun. 7, 2015, pp. 9744-9755, vol. 44, No. 21, Royal Society of Chemistry.

[Fig. 1]
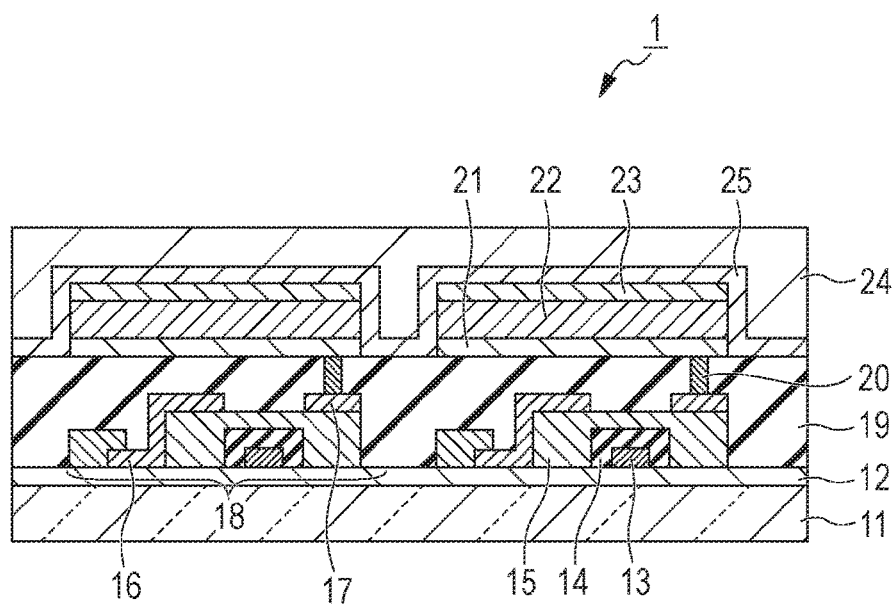

[Fig. 2]
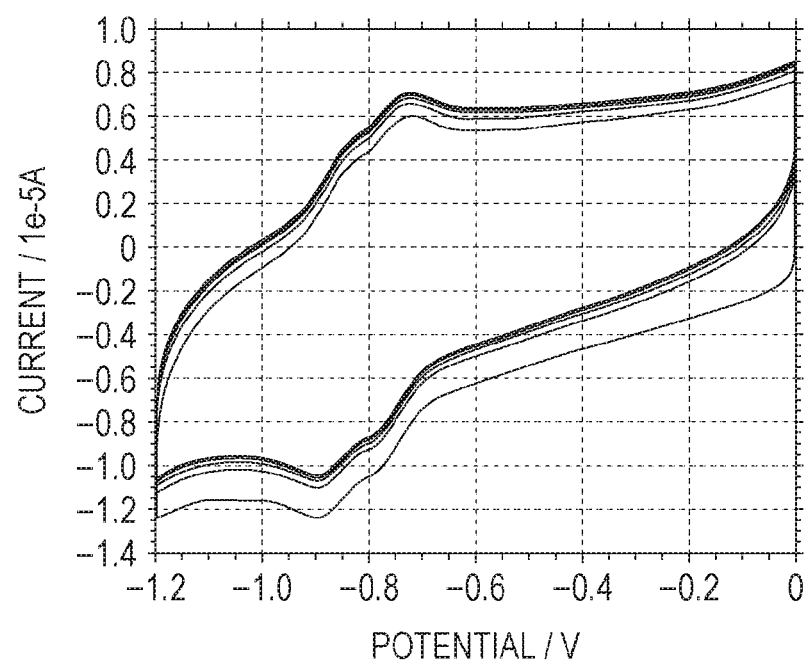

[Fig. 3]
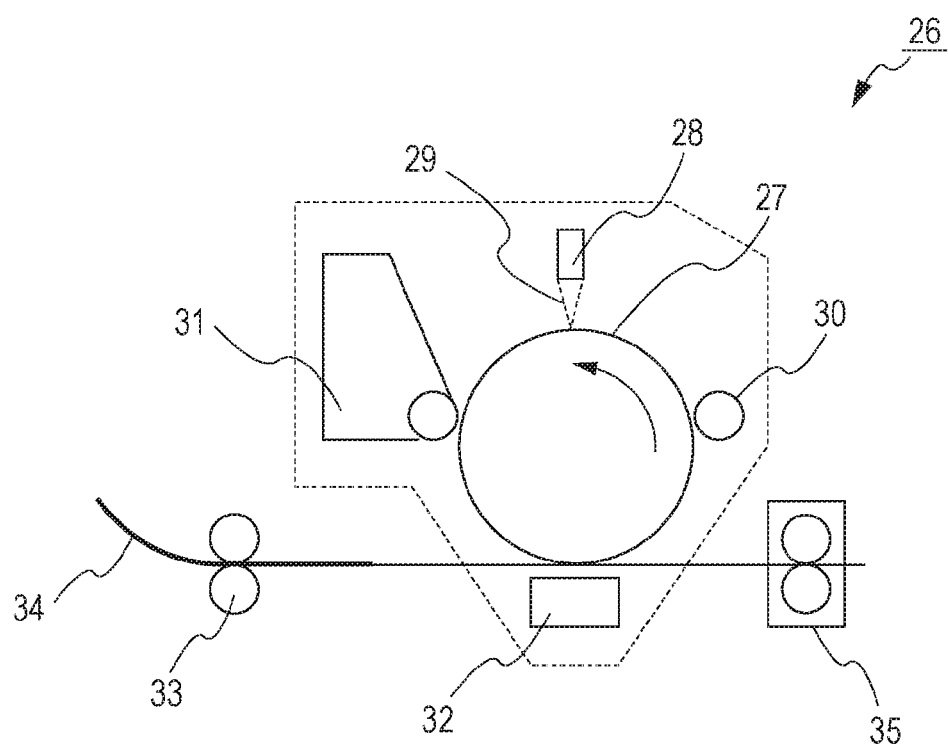

[Fig. 4]
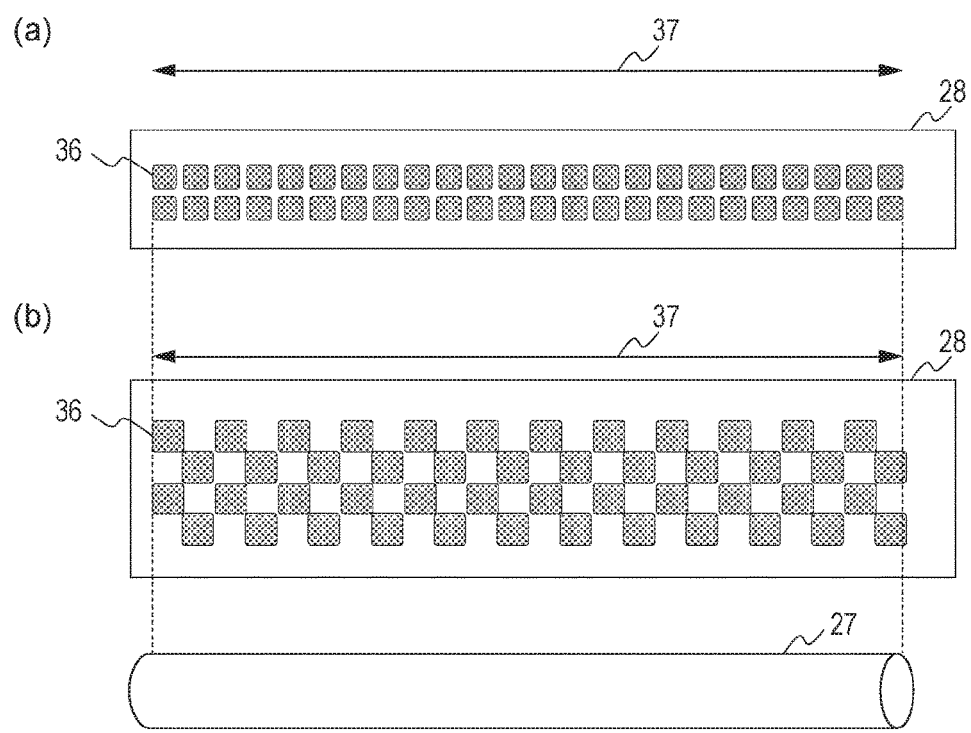

[Fig. 5]
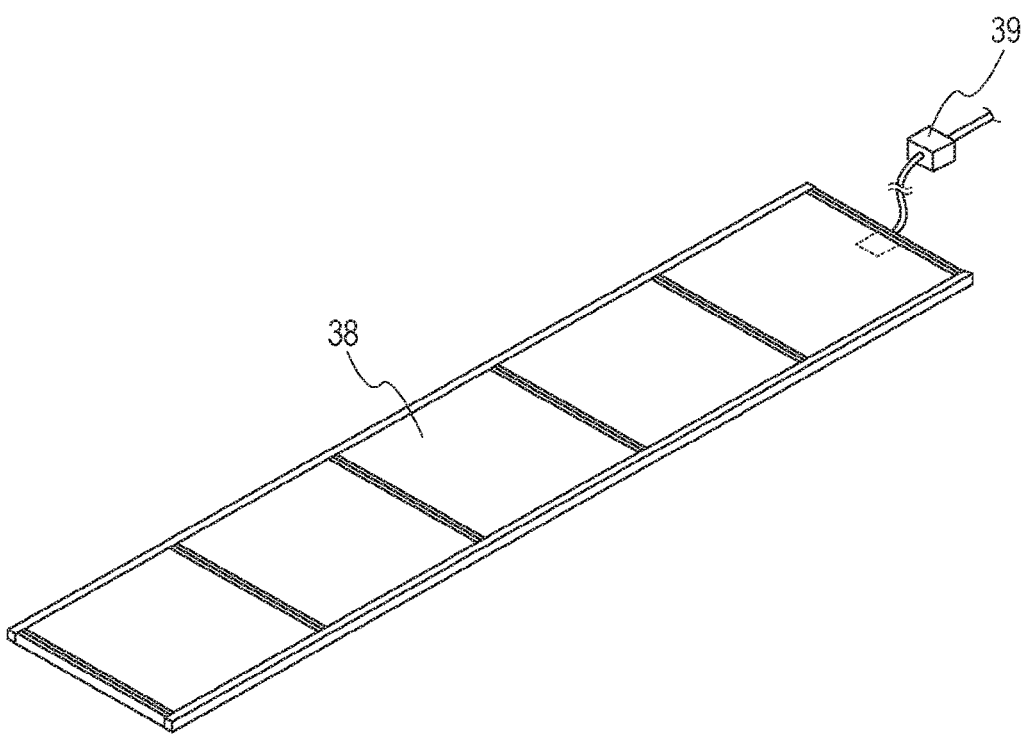

ORGANIC COMPOUND, FIELD ELEMENT, ORGANIC LIGHT-EMITTING ELEMENT, DISPLAY APPARATUS, IMAGE INFORMATION-PROCESSING APPARATUS, LIGHTING APPARATUS, IMAGE-FORMING APPARATUS, AND EXPOSURE APPARATUS

CROSS-REFERENCE TO RELATED APPLICATIONS

This application is a National Stage filing of International Application No. PCT/JP2015/003106 filed Jun. 22, 2015, which claims the benefit of Japanese Patent Application No. 2014-133280, filed Jun. 27, 2014 and Japanese Patent Application No. 2015-009743, filed Jan. 21, 2015, the disclosures of each of which are hereby incorporated by reference herein in their entirety.

TECHNICAL FIELD

The present invention relates to a 1,1',3,3'-tetraphenyl-2,2'-bibenzo[d]imidazolidene compound, a field element, an organic light-emitting element, a display apparatus, an image information-processing apparatus, a lighting apparatus, an image-forming apparatus, and an exposure apparatus.

BACKGROUND ART

Organic light-emitting elements are elements having an anode, a cathode, and an organic compound layer between the two electrodes. In an organic light-emitting element, holes and electrons injected from the two electrodes recombine in the organic compound layer as an emitting layer and form excitons. The element emits light when the excitons return to the ground state. The recent significant advances in organic light-emitting elements have enabled us to make them into thin and lightweight light-emitting devices with low driving voltages, a wide variety of emission wavelengths, and quick response.

It is important for lower-voltage organic light-emitting elements that the elements are improved in terms of electron injection. Examples of ways to improve electron injection include those described in PTL 1 and 2, in which metal is used.

Compounds such as 1-A, 1-B, and 1-C, for which synthetic processes described in NPL 1, 2, and 3 are known, are made from instable materials and are easily oxidized in the air.

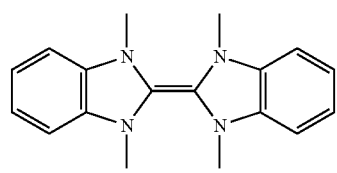

1-A

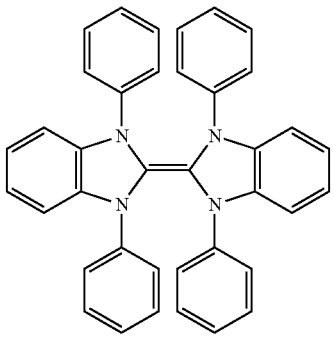

1-B

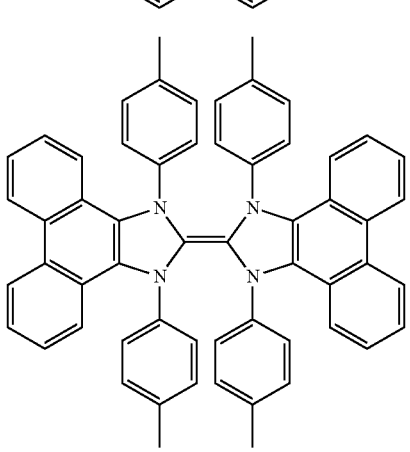

1-C

The organic light-emitting elements described in PTL 1 and 2 have an electron injection layer made from a metal-containing compound. This is advantageous in respect of electron injection, but on the other hand affects the life of the elements because such a compound is highly reactive with water.

The compounds described in NPL 1 to 3, which are susceptible to oxidation in the air, are difficult to handle in the air.

CITATION LIST

Patent Literature

PTL 1: Japanese Patent Laid-Open No. 2003-068468
PTL 2: Japanese Patent Laid-Open No. 2002-100482

Non Patent Literature

NPL 1: F. Ekkehardt Hahn "N,N'-Bis(2,2-dimethylpropyl) benzimidazolin-2-ylidene: A Stable Nucleophilic Carbene Derived from Benzimidazole," Chemistry—A European Journal (1999), 5, (6), 1931-1935.
NPL 2: Bourson, Jean, "Benzimidazoles. III. Action of bases on 1,3-diphenylbenzimidazolium salts" Bulletin de la Societe Chimique de France (1971), (10), 3541-7.
NPL 3: Farman Ullah, "Annulated N-Heterocyclic Carbenes: 1,3-Ditolylphenanthreno[9,10-d]imidazol-2-ylidene and Transition Metal Complexes Thereof," Organometallics (2009), 28 (8), 2441-2449.
NPL 4: D. Vasudevan "Electroreduction of oxygen in aprotic media" Journal of Electroanalytical Chemistry 192 (1995) 69-74.

SUMMARY OF INVENTION

An aspect of the invention provides an organic compound insusceptible to oxidation in the air.

In more specific terms, an aspect of the invention provides a 1,1',3,3'-tetraphenyl-2,2'-bibenzo[d]imidazolidene compound represented by general formula (1).

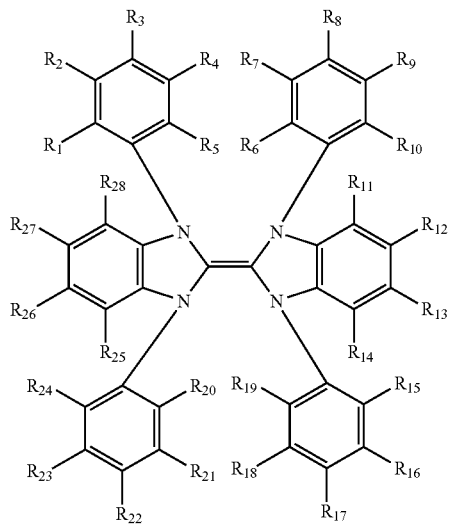

(1)

In formula (1), $R_1$ to $R_{28}$ are each independently selected from a hydrogen atom and a substituent. The substituent is any of a halogen atom, an alkyl group containing 1 or more and 8 or less carbon atoms, and a substituted or unsubstituted aryl group. At least one of $R_1$ to $R_{28}$ is the substituent.

Further features of the present invention will become apparent from the following description of exemplary embodiments with reference to the attached drawings.

BRIEF DESCRIPTION OF DRAWINGS

FIG. 1 is a schematic cross-sectional diagram illustrating an example of a display apparatus having organic light-emitting elements according to an embodiment and active elements coupled to the organic light-emitting elements.

FIG. 2 is a cyclic voltammogram of an organic compound as an example of the invention.

FIG. 3 is a schematic diagram illustrating an example of an image-forming apparatus according to an embodiment.

Part (a) of FIG. 4 is a schematic diagram illustrating an example of an exposure apparatus according to an embodiment. Part (b) of FIG. 4 is another schematic diagram illustrating the same example of an exposure apparatus according to an embodiment.

FIG. 5 is a schematic diagram illustrating an example of a lighting apparatus according to an embodiment.

DESCRIPTION OF EMBODIMENTS

An embodiment is a 1,1'3,3'-tetraphenyl-2,2'-bibenzo[d]imidazolidene compound having a substituent. The substituent reduces the reactivity of the compound with oxygen and water in the air, making the compound stable. Such a 1,1',3,3'-tetraphenyl-2,2'-bibenzo[d]imidazolidene compound may herein be referred to as an organic compound according to an embodiment.

An organic compound according to an embodiment is an organic compound represented by general formula (1).

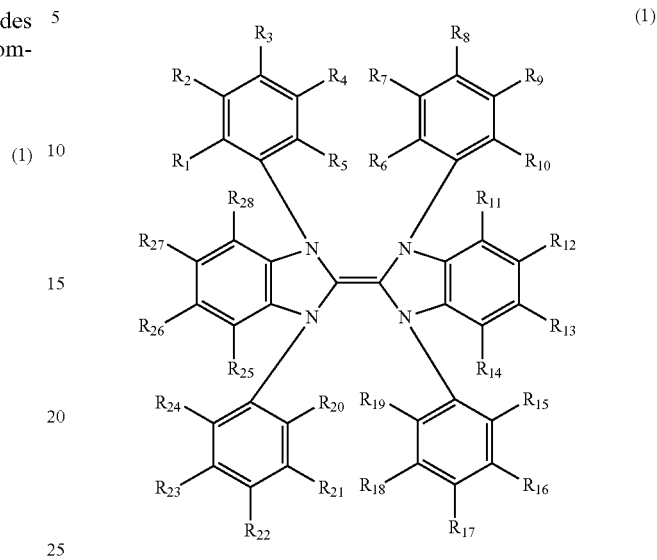

(1)

In formula (1), $R_1$ to $R_{28}$ are each independently selected from a hydrogen atom and a substituent. The substituent is any of a halogen atom, an alkyl group containing 1 or more and 8 or less carbon atoms, and a substituted or unsubstituted aryl group. At least one of the $R_1$ to $R_{28}$ is the substituent.

The halogen atom can be a fluorine atom, a chlorine atom, a bromine atom, an iodine atom, or similar, preferably a fluorine atom.

Specific examples of alkyl groups containing 1 or more and 8 or less carbon atoms include a methyl group, an ethyl group, a n-propyl group, an isopropyl group, a n-butyl group, a isobutyl group, a sec-butyl group, a tert-butyl group, a n-pentyl group, a n-hexyl group, and a n-octyl group.

The aryl group is, for example, a phenyl group, a naphthyl group, a phenanthrenyl group, a pyrenyl group, or a fluorenyl group, preferably a phenyl group.

The aryl group may have at least one substituent. Examples of the at least one substituent include alkyl groups such as a methyl group, an ethyl group, a n-propyl group, an isopropyl group, a n-butyl group, an isobutyl group, a sec-butyl group, and a tert-butyl group, aromatic hydrocarbon groups such as a phenyl group, a naphthyl group, a phenanthryl group, and a fluorenyl group, and halogen atoms such as a fluorine atom, a chlorine atom, a bromine atom, and an iodine atom. If the aryl group has a halogen atom as a substituent, it is preferred that the halogen atom be a fluorine atom.

It is preferred that an organic compound according to an embodiment have any of an alkyl group containing 1 or more and 8 or less carbon atoms and a phenyl group in at least one of $R_{11}$ to $R_{14}$ and $R_{25}$ to $R_{28}$ in general formula (1), more preferably at least one of $R_{12}$, $R_{13}$, $R_{26}$, and $R_{27}$ in general formula (1).

The compound is highly stable when at least one of $R_1$ to $R_{10}$ and $R_{15}$ to $R_{24}$ in general formula (1) is any of a fluorine atom, a tert-butyl group, a sec-butyl group, an isobutyl group, and an isopropyl group with $R_{12}$ to $R_{14}$ and $R_{25}$ to $R_{28}$ being hydrogen atoms.

Characteristics of an Organic Compound According to an Embodiment

An organic compound according to an embodiment has a structure in which a 1,1',3,3'-tetraphenyl-2,2'-bibenzo[d]imidazolidene compound has a substituent. The substituent provides bulkiness or makes the potential of the organic compound stable. This structure, in which 1,1',3,3'-tetraphenyl-2,2'-bibenzo[d]imidazolidene compound has a substituent, reduces the reactivity of the organic compound according to an embodiment with oxygen and water in the air, ensuring good electron injection combined with stability.

An advantage of the use of an organic molecule, rather than a metallic ion, as an electron injection material in an organic element is its low solubility in water. Commonly used alkali-metal-containing materials, such as lithium fluoride and lithium-quinolinol complexes, exhibits high electron injection properties, but on the other hand are highly soluble in water. The use of such a material in an organic light-emitting element, therefore, ensures injection from the electrode but on the other hand can be a cause of element instability because the material readily forms ions upon exposure to water or any other external agent.

Making an electron injection material from a metal-free organic compound therefore contributes to improving the stability of organic light-emitting elements. The electron injection material can have a HOMO level near the energy level of the electrode. The organic compound can have a low HOMO level because the electrode has a low energy level. The compound can therefore have a low (small) oxidation potential.

Having a low HOMO level is almost synonymous with having a low first oxidation potential as measured using CV. A lowering of a HOMO level represents its movement toward the vacuum level.

The use of such a compound with a low HOMO level reduces the energy barrier that electrons need to overcome to be injected from the cathode into the electron conduction level. A material can serve as an electron injection material only when having a somewhat low first oxidation potential, more specifically a first oxidation potential of 0 V or less (vs. Fc/Fc+), preferably −0.7 V or less (vs. Fc/Fc+).

The injection of electrons from the cathode into the electron injection layer can be further improved with the use of a material having a lower HOMO level, i.e., a lower first oxidation potential.

An n-type dopant, however, can be inert to oxygen only when the first oxidation potential of the n-type dopant is higher than at least the reduction potential of oxygen. Oxygen has a reduction potential ($O_2/O_2^-$) of −1.22 V (vs. Fc/Fc+) in DMF as solvent. Some reduction potentials of oxygen can be found in NPL 4.

This means that an electron injection material can have excellent electron injection properties while being inert to oxygen when its oxidation potential falls within an appropriate range.

An organic compound according to an embodiment therefore has a first oxidation potential of −1.20 V or more and 0.00 V or less (vs. Fc/Fc+) in DMF as solvent, preferably −1.20 V or more and −0.70 V or less (vs. Fc/Fc+).

The oxidation potential can be measured using cyclic voltammetry (CV). To be more specific, the oxidation potential can be determined from the peak oxidation current measured using CV.

An aspect of the invention was made through the finding of a structure that exhibits good electron injection properties and is inert to oxygen based on the following molecular design.

1. Ensure the greatest oxidation potential that can be achieved without affecting injection The inventors measured the oxidation potential of a synthesized compound having structure 1-B. The oxidation potential was measured to be −0.92 V, a value sufficient in respect of injection.

This compound was then substituted with an electron-attracting substituent in an attempt to improve the stability of the compound.

To be more specific, fluorine atoms were introduced. Introducing fluorine atoms should improve the stability of the compound by increasing the oxidation potential of the compound from −0.90 V to approximately −0.70 V, and should reduce the affinity of the compound for oxygen by making intermolecular interactions smaller.

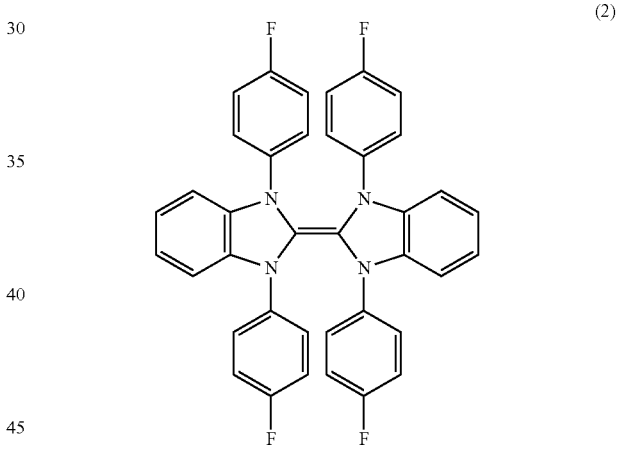

(2)

The compound illustrated in (2), synthesized as an example, had an oxidation potential of −0.85 V, greater than that of 1-B. This compound was stable in the air and more inert to oxygen than 1-B. Introducing fluorine atoms therefore controlled the oxidation potential of the compound and resulted in successful synthesis of a stable compound. Furthermore, introducing fluorine atoms enhanced the stability of the compound by reducing the affinity of the compound for oxygen.

Further substitution, such as substitution with an alkyl group, successfully produced a compound that was stable in the air even with an oxidation potential of −0.90 V or less.

The CV measurements were conducted in a 0.1 M solution of tetrabutylammonium perchlorate in N,N-dimethylformamide using a Ag/Ag$^+$ reference electrode, a Pt counter electrode, and a glassy carbon working electrode. The potential sweep rate was 0.5 V/s. The measuring instrument was ALS 660C Electrochemical Analyzer.

2. Introduce a substituent to protect the HOMO orbital from oxygen

Oxidation of a molecule should occur through the reaction between the orbital where the HOMO of the molecule spreads and an oxygen molecule. The HOMO orbital of 1-A and 1-B spreads mainly over the 1,1',3,3'-tetrahydro-2,2'-bibenzo[d]imidazolidene skeleton. As a result, 1-A is very instable, whereas 1-B, substituted with phenyl groups, is rather stable.

The substitution with phenyl groups alone, however, does not make the compound stable in the air. The inventors thus conducted studies in search of a substituent that would make the compound stable in the air and found two methods through which the material could be stabilized.

2-a. Introducing a bulky substituent, such as a tert-butyl (tBu) group or an isopropyl group, makes the compound stable in the air.

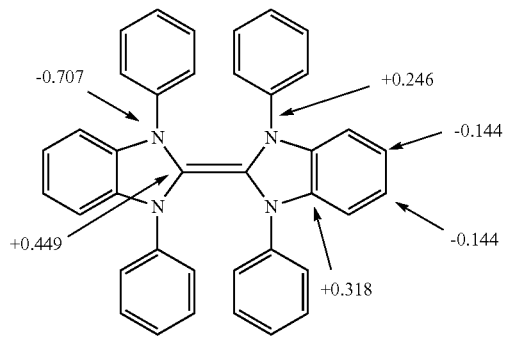

(4)

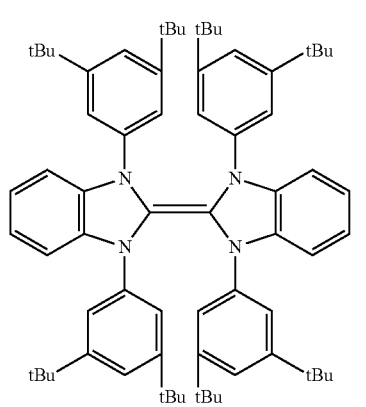

(3)

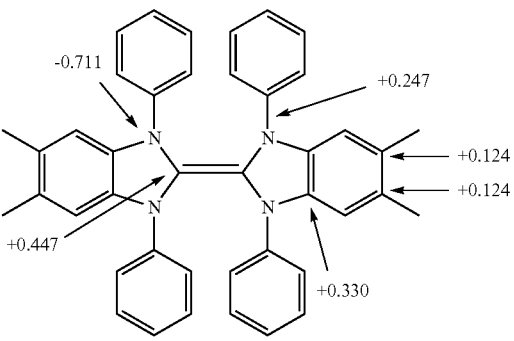

(5)

The compound illustrated in (3), synthesized as an example, was stable in the air. Having a bulky substituent, this compound was more inert to oxygen than 1-B. Introducing a bulky substituent therefore successfully produced a material that was stable in the air despite a small oxidation potential. Such a structure allows the material to be stable in the air even when its oxidation potential is smaller than −0.09 V.

2-b. Introduce a substituent to particular positions in the 1,1',3,3'-tetrahydro-2,2'-bibenzo[d]imidazolidene skeleton to stabilize highly oxidizable sites. This makes the compound stable in the air.

To find highly oxidizable sites in the 1,1',3,3'-tetrahydro-2,2'-bibenzo[d]imidazolidene skeleton, the inventors analyzed the structure for charge density through molecular orbital computation using the following procedure: The structures of the molecule in the electronic ground and excitation states were determined on Gaussian 03 Revision D.01, commercially available software for the computation of electronic states. The density functional theory was used as a quantum chemical computation method with the B3LYP functional. The basis function was 6-31G (d).

As can be seen from the results presented in (4), nitrogen atoms, which should be highly active, had a great negative charge. In an organic compound according to an embodiment, phenyl groups protect these sites to improve the stability of the compound.

Position 5 in the 1,1',3,3'-tetrahydro-2,2'-bibenzo[d]imidazolidene skeleton has a negative value. The 1,1',3,3'-tetrahydro-2,2'-bibenzo[d]imidazolidene skeleton has point symmetry and, therefore, positions 6, 5', and 6, corresponding to position 5, has the same value as position 5. It appears that these sites make the 1,1',3,3'-tetrahydro-2,2'-bibenzo[d]imidazolidene skeleton instable. The inventors thus introduced substituents such as an alkyl group to these sites and observed the resulting change in charge density. As can be seen from the results presented in (5), introduction of a substituent made these sites positively charged, making the entire molecule more stable.

The inventors also studied the inertness of organic compounds according to an embodiment to water to assess them for reactivity with water in the air. Powders of lithium fluoride and cesium fluoride, i.e., alkali-metal-containing materials, and powders of some organic compounds according to an embodiment were left under high-humidity (95%) conditions for 1 hour, and visual observations were compared. The results are summarized in Table 1.

TABLE 11

| | | Reactivity |
|---|---|---|
| Organic compound 1 according to an embodiment | [structure: 2,2'-bis(benzimidazolylidene) with four 4-fluorophenyl groups on the N atoms] | No change |
| Organic compound 2 according to an embodiment | [structure: 2,2'-bis(benzimidazolylidene) with four 3,5-di-tert-butylphenyl groups on the N atoms] | No change |
| Organic compound 3 according to an embodiment | [structure: 2,2'-bis(5,6-dimethylbenzimidazolylidene) with four 4-fluorophenyl groups on the N atoms] | No change |
| Organic compound 4 according to an embodiment | [structure: 2,2'-bis(5,6-dimethylbenzimidazolylidene) with four phenyl groups on the N atoms] | No change |

TABLE 11-continued

| | | Reactivity |
|---|---|---|
| Comparative compound 1 | LiF | Slightly deliquesced |
| Comparative compound 2 | CsF | Deliquesced |
| Comparative compound 3 | 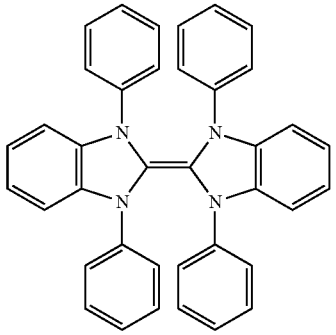 [SMILES: c1ccc(N2C(=C3N(c4ccccc4)c4ccccc4N3c3ccccc3)N(c3ccccc3)c3ccccc32)cc1] | Reddened |
| Comparative compound 4 | 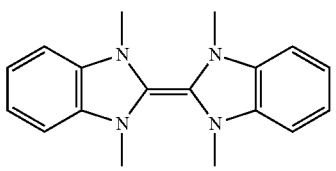 [SMILES: CN1C(=C2N(C)c3ccccc3N2C)N(C)c2ccccc21] | Deliquesced and blackened |

The results indicated that the alkali metal salts (comparative compounds 1 and 2) and the 1,1',3,3'-tetrahydro-2,2'-bibenzo[d]imidazolidene compounds whose nitrogen atoms had a phenyl or alkyl group as a substituent (comparative compounds 3 and 4) deliquesced or oxidized. Comparing comparative compounds 3 and 4 revealed that the compound having methyl groups, i.e., a smaller substituent, around the nitrogen atoms oxidized faster, and blackened while deliquescing. The compounds according to an embodiment experienced no deliquescence, oxidation, or any other change, demonstrating their stability.

The organic compound according to an embodiment has electron injection properties sufficient for use as an electron injection material and is insusceptible to oxidation in the air.

The oxidation potential of compound A1 as an example of the organic compound according to an embodiment was reversible as indicated in FIG. 2, demonstrating that this structure is insusceptible to oxidation and reduction. This compound serves as a strong electron donor because of its low oxidation potential, and mixing it with a material that behaves as a strong electron acceptor produces a charge transfer complex. When an organic light-emitting element has an organic compound layer containing this charge transfer complex in contact with an electrode, the complex helps the injection of the carrier from the electrode.

Comparative compounds 3 and 4 were also subjected to the measurement of oxidation potential after being left in the air. No oxidation potential peak was observed around −1.0 V, confirming that these compounds lost their initial characteristics through oxidation.

The use of a 1,1',3,3'-tetraphenyl-2,2'-bibenzo[d]imidazolidene compound, which has an oxidation potential smaller than those of the comparative compounds and is more inert to water than known materials (e.g., alkali metal salts and alkali metals), in an electron injection layer makes the element stable.

The presence of an organic compound according to an embodiment in an organic light-emitting element can be verified through the analysis of the organic compound layer of the element using TOF-SIMS or similar. This method of analysis is merely an example, and it is possible to extract the organic compound from the organic light-emitting element and analyze it using IR, UV, NMR, or similar.

Examples of 1,1',3,3'-tetraphenyl-2,2'-bibenzo[d]imidazolidene Compounds According to an Embodiment The following illustrates some examples of specific structural formulae of 1,1',3,3'-tetraphenyl-2,2'-bibenzo[d]imidazolidene compounds according to an embodiment. tBu denotes a tertiary butyl group.

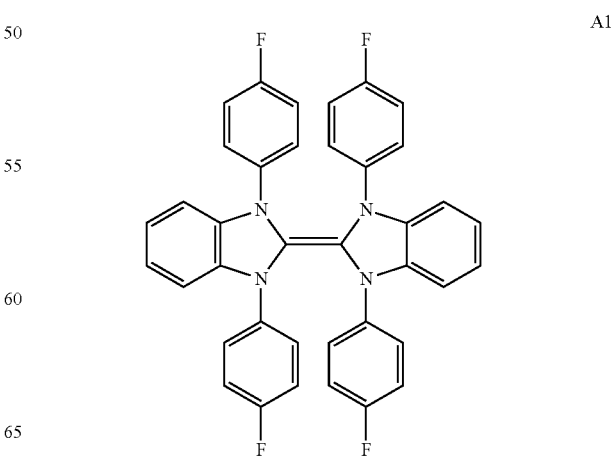

A1

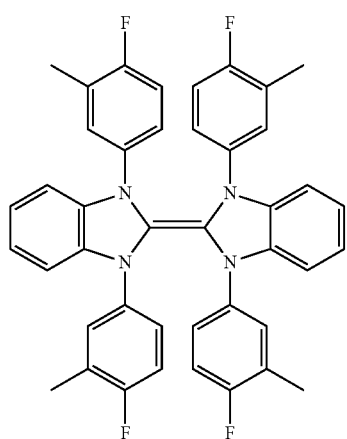
A2
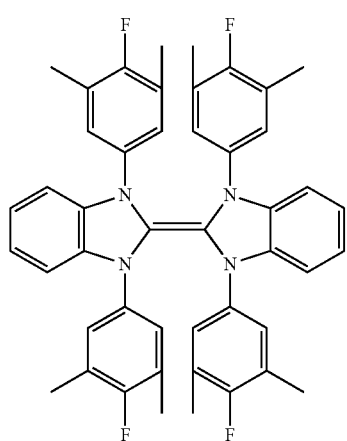
A3
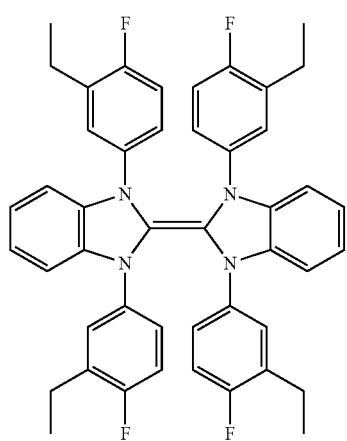
A4
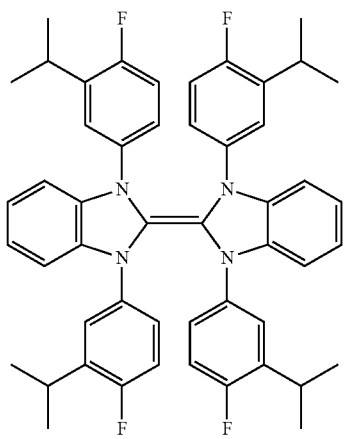
A5
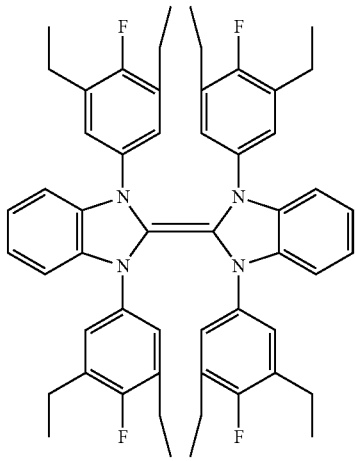
A6
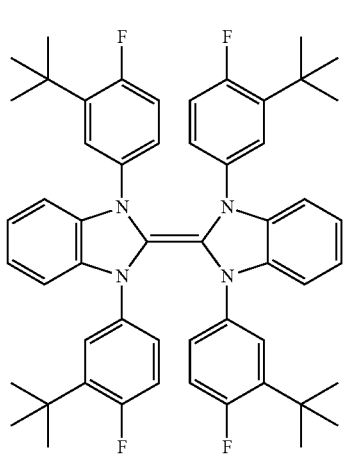
A7

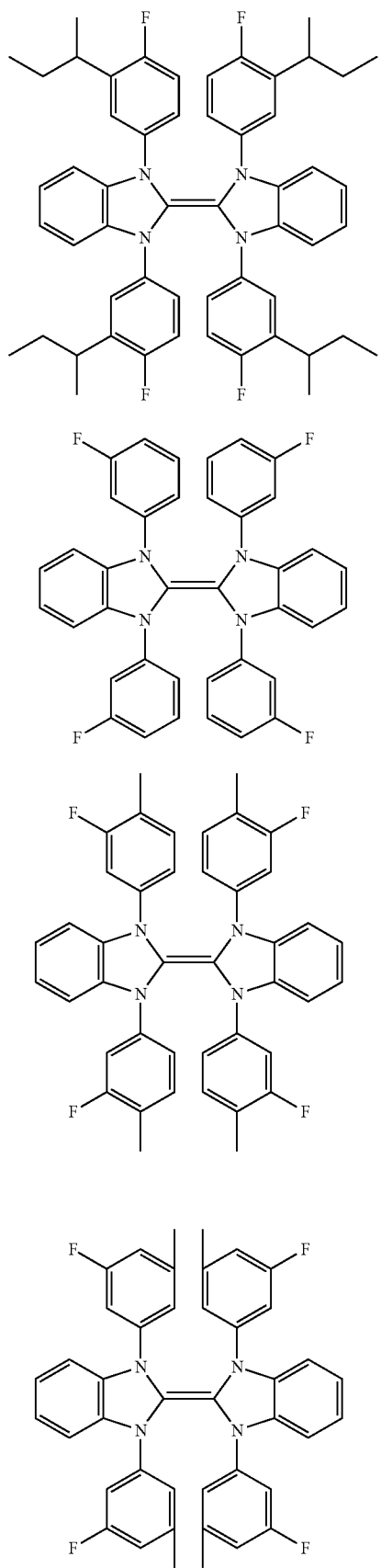
A8
A9
A10
A11
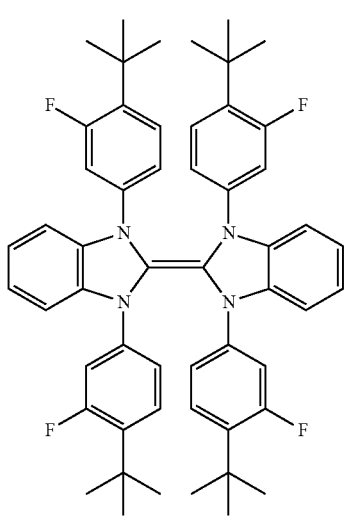
A12
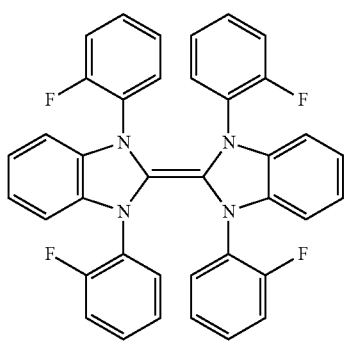
A13
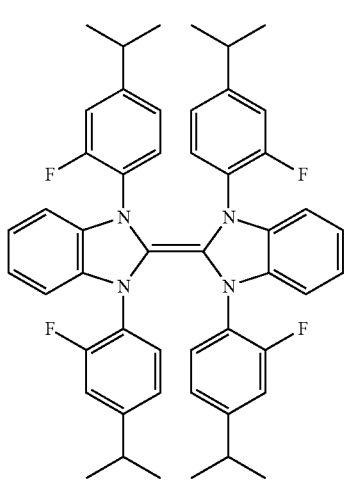
A14

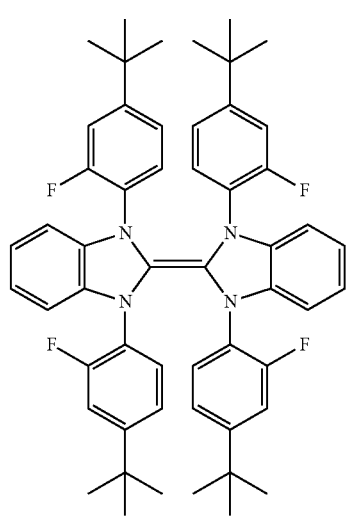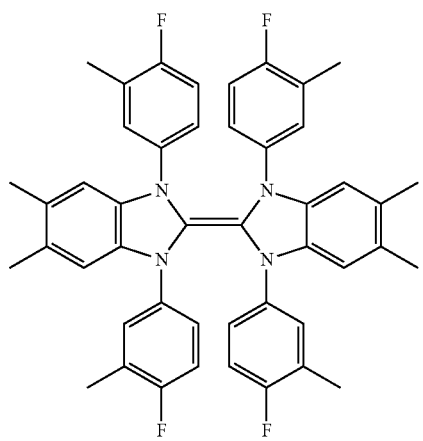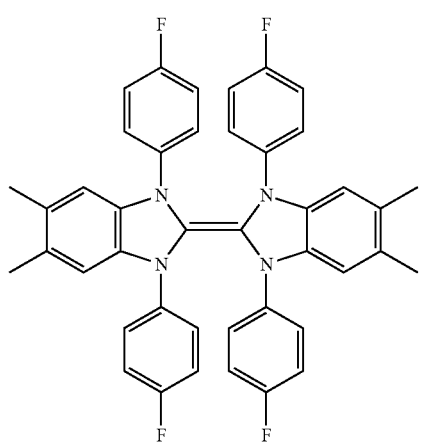

A21
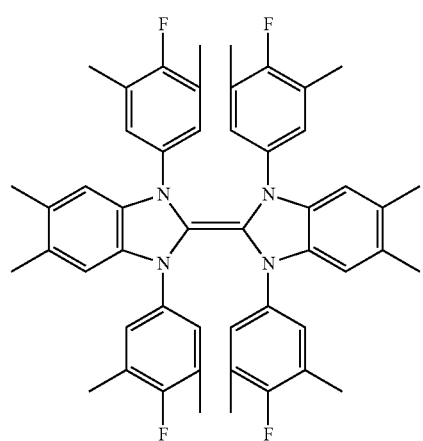
A22
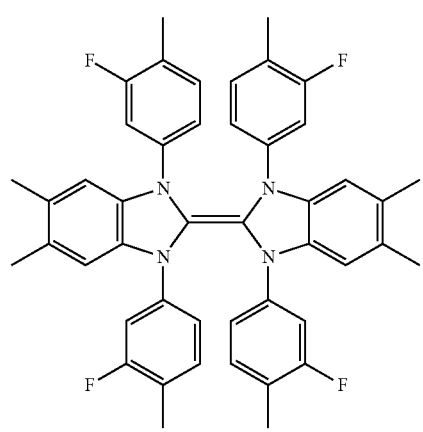
A23
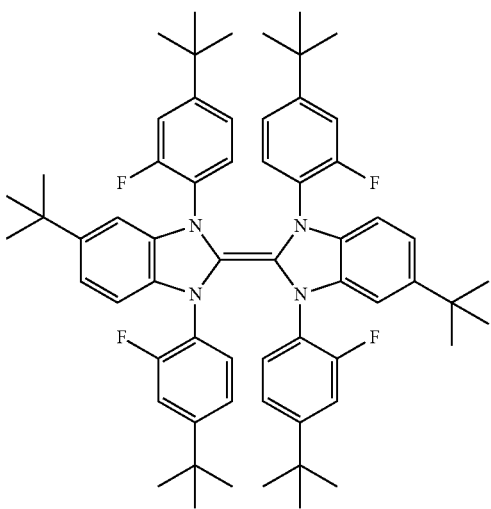
A24
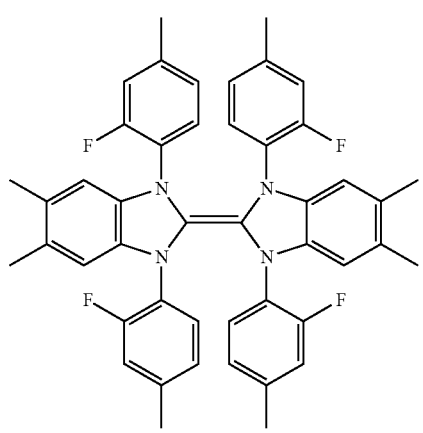
A25
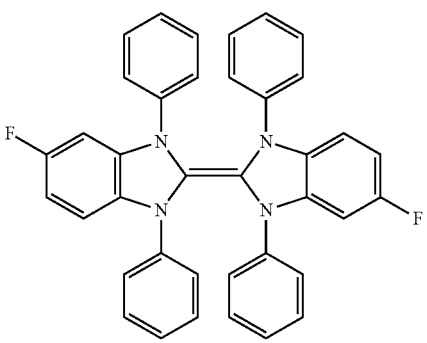
A26
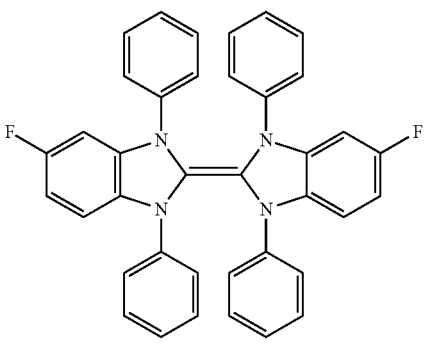
A27
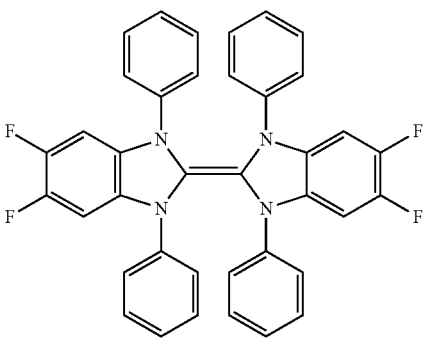

-continued
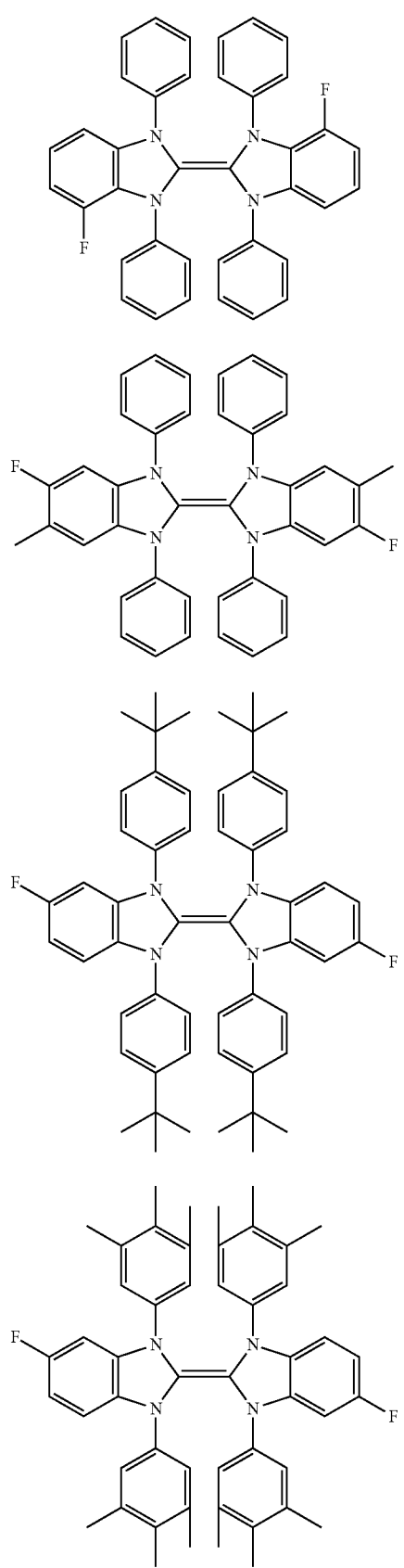
A28
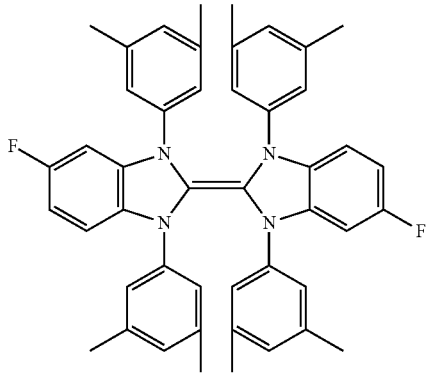
A29
A30
A31
-continued
A32
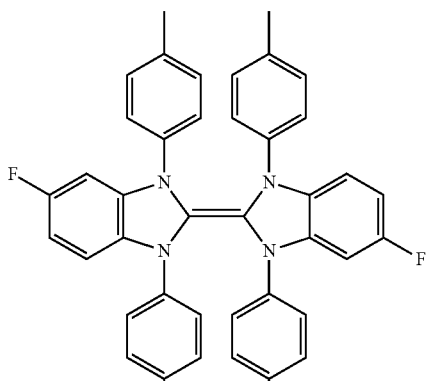
A33
A34
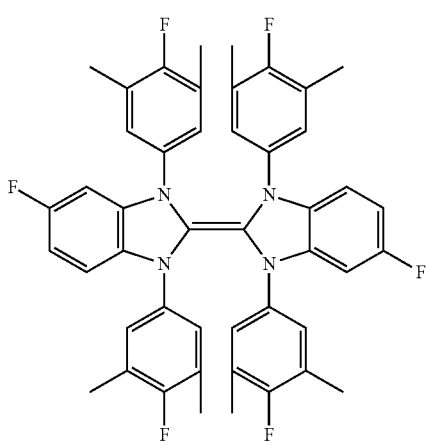
A35
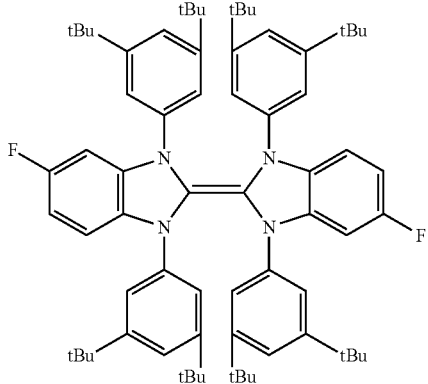

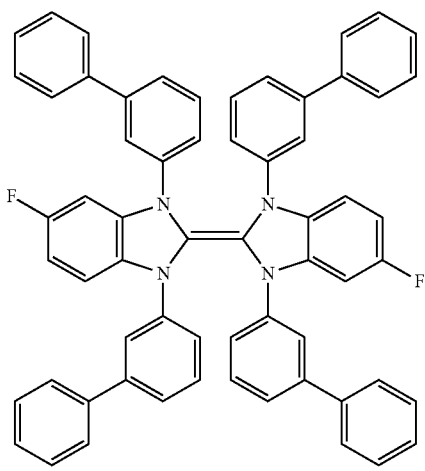
A36
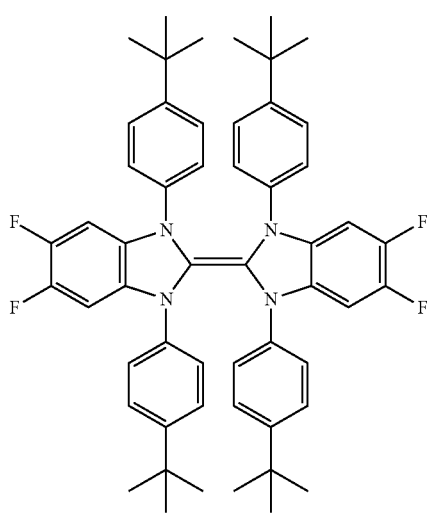
A37
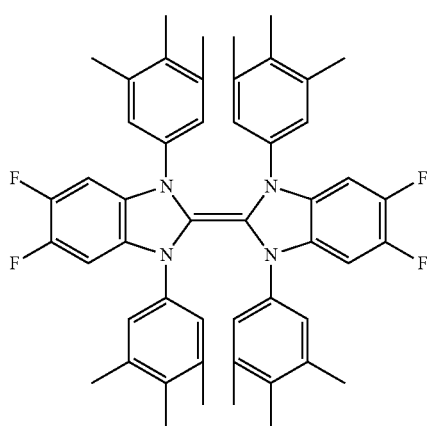
A38
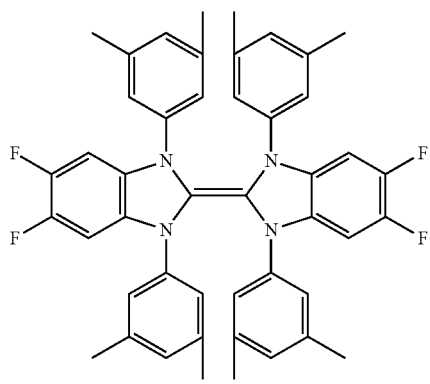
A39
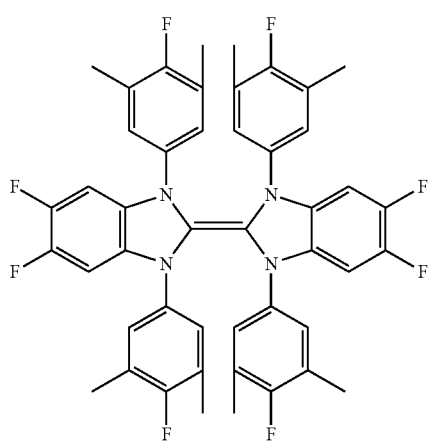
A40
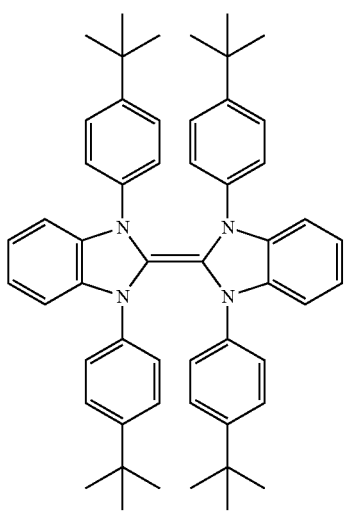
B1

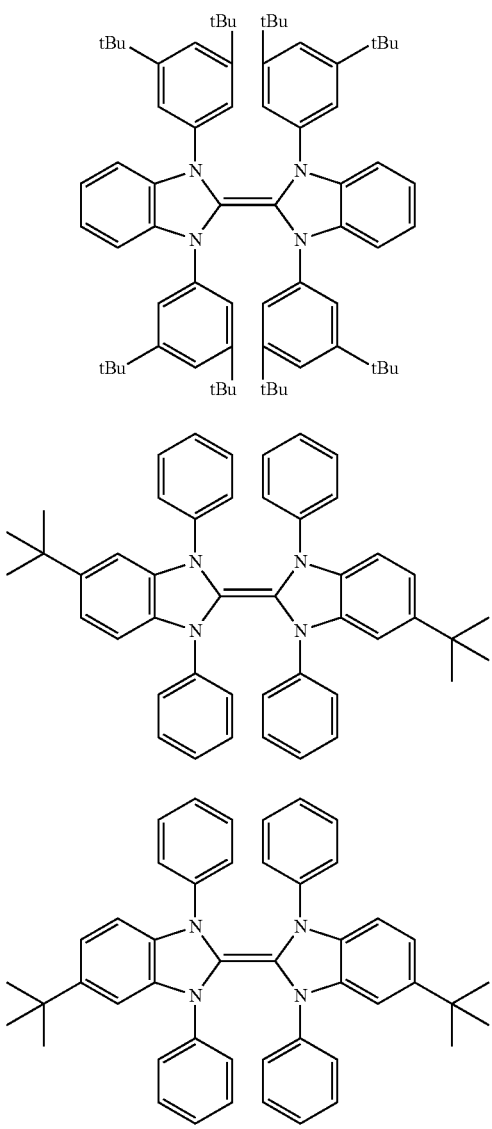
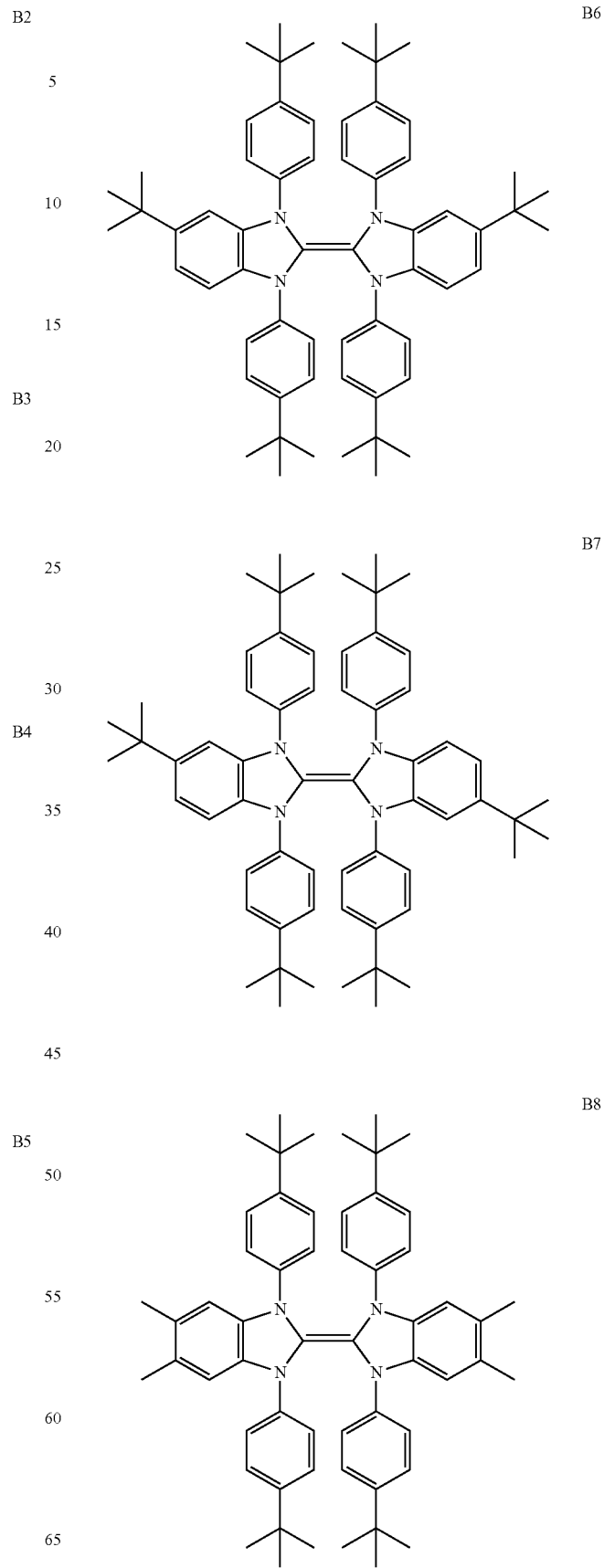

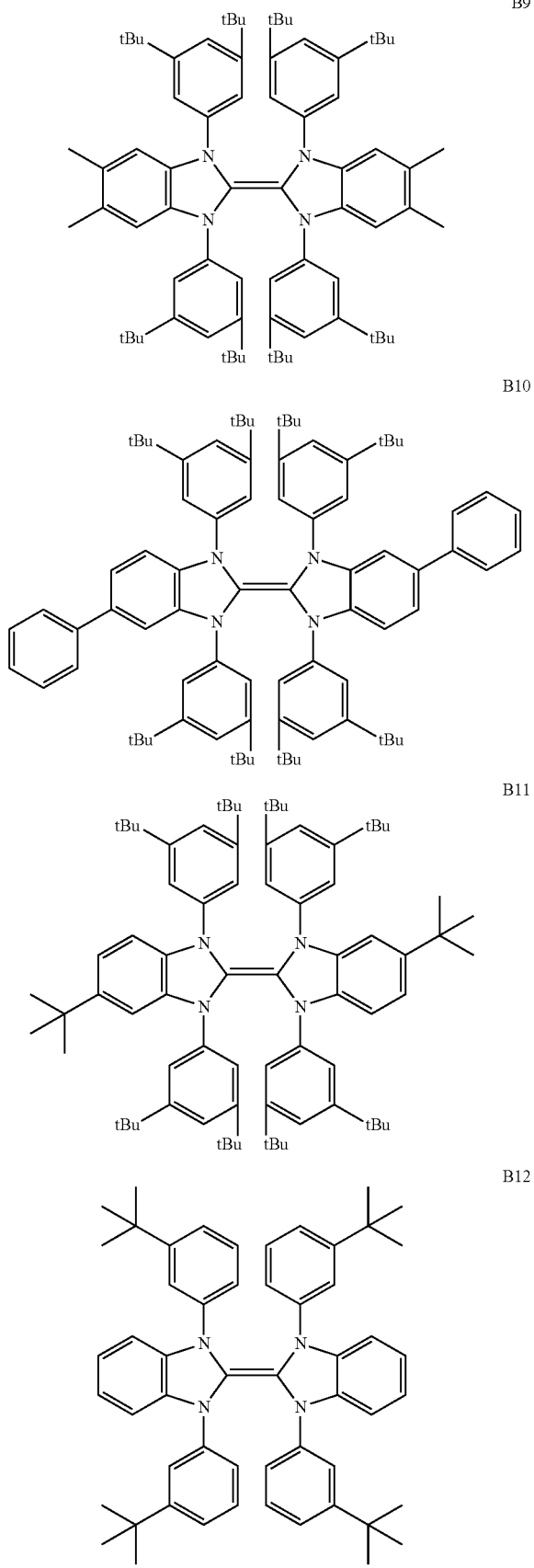
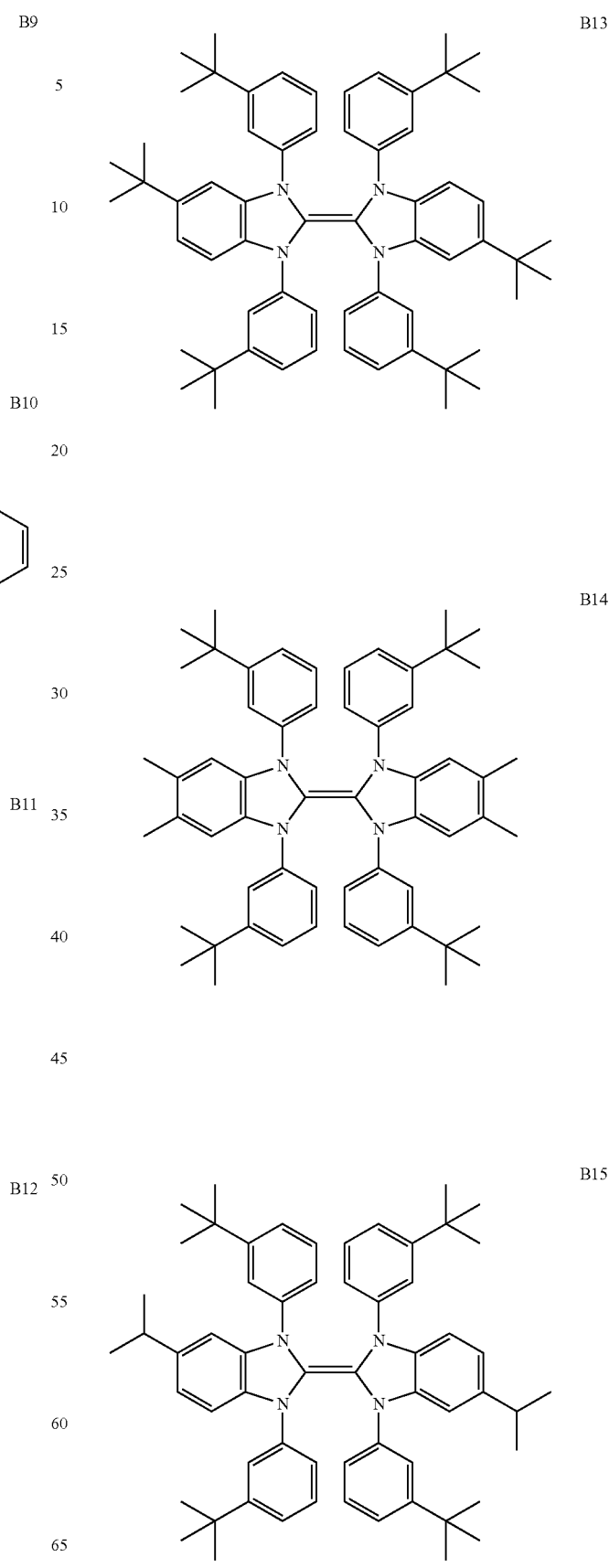

-continued
B16
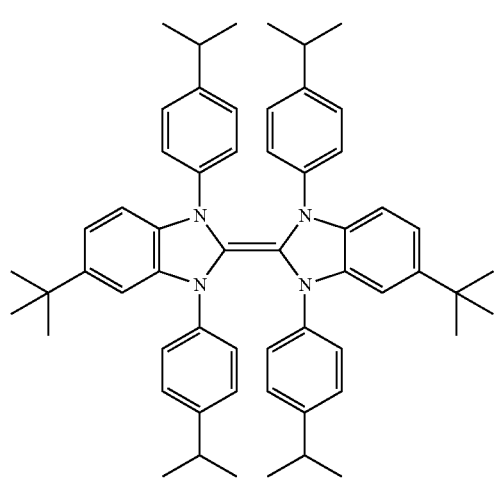
B17
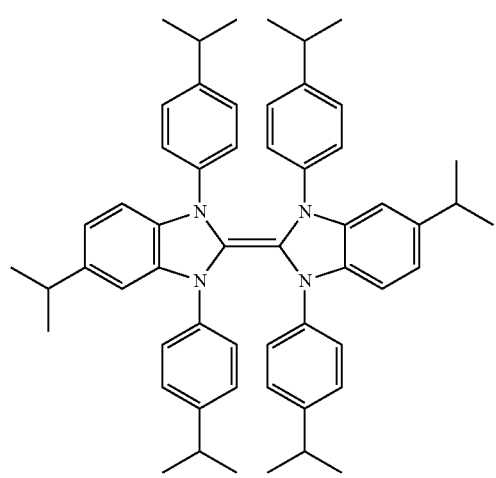
B18
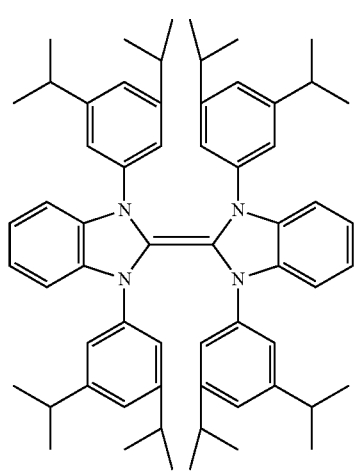
-continued
B19
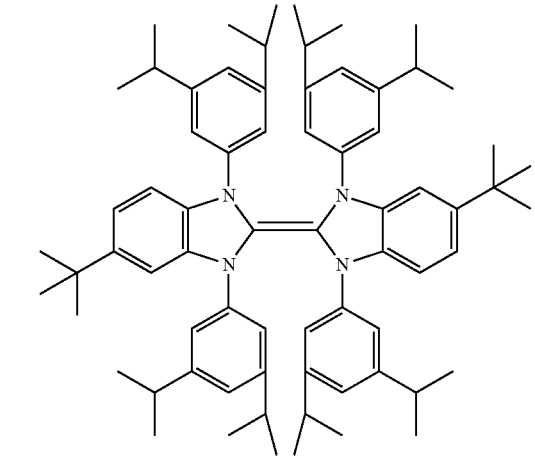
B20
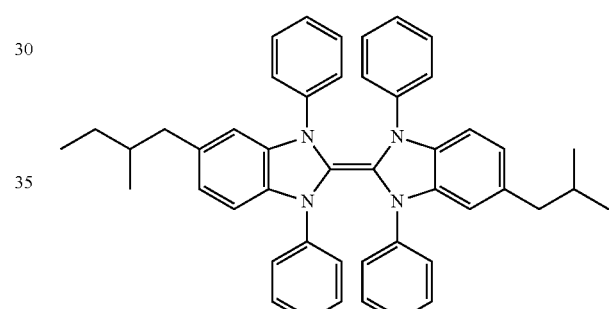
B21
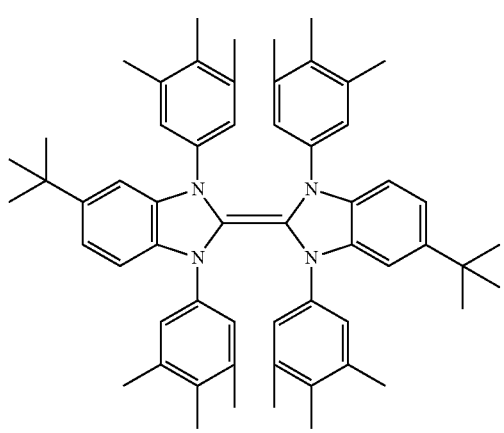

B22 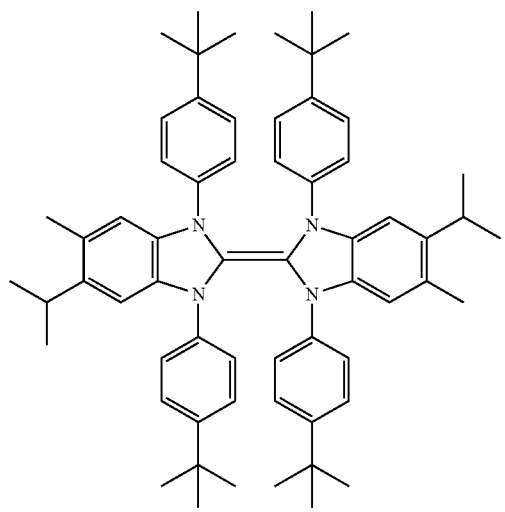
B25 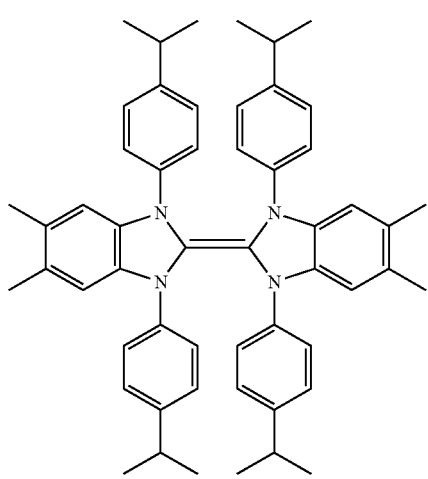
B23 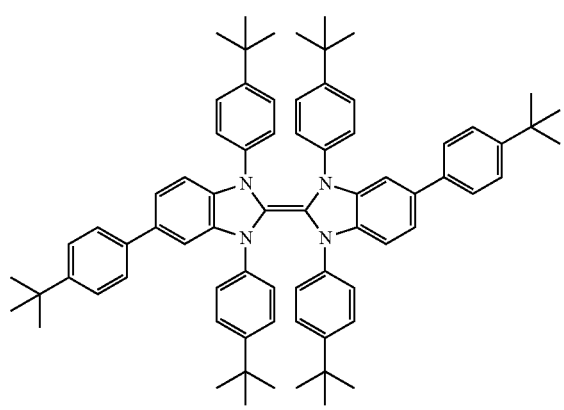
B26 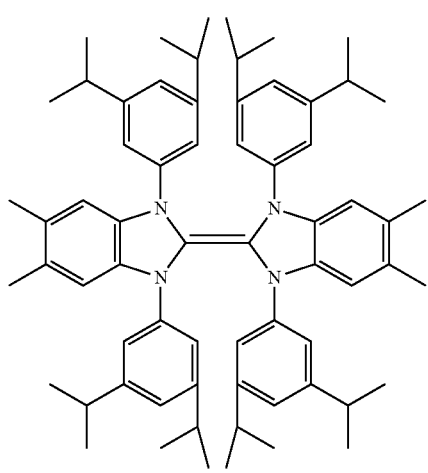
B24 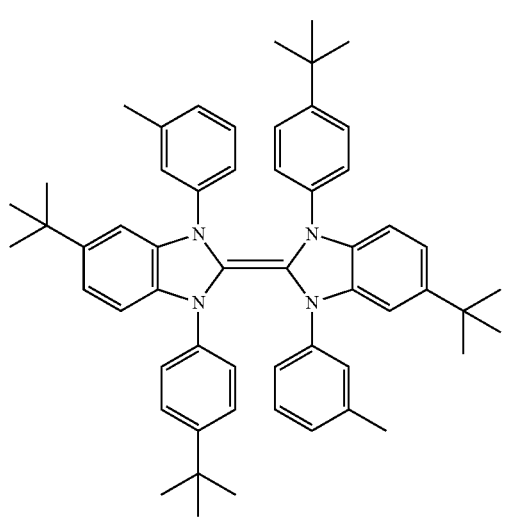
B27 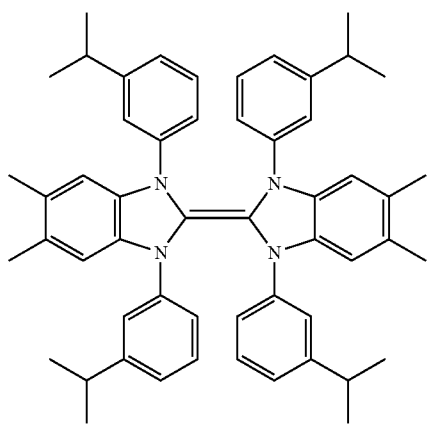

B28
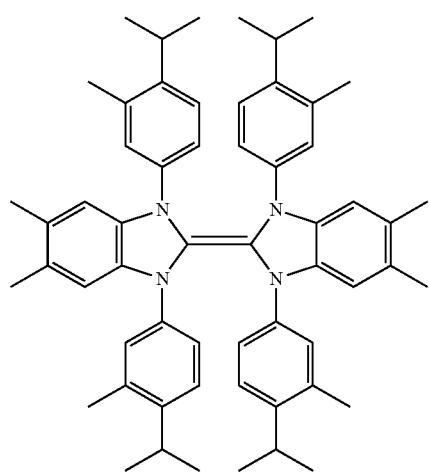
B29
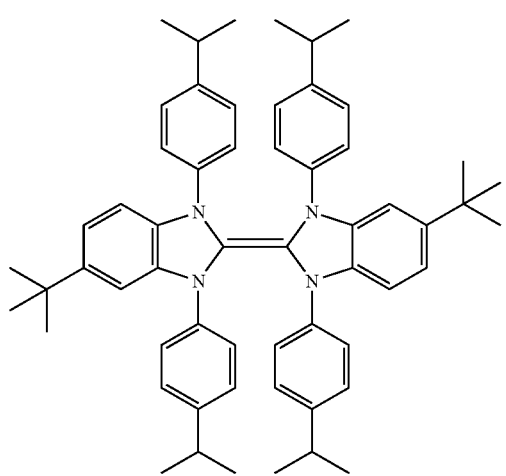
B30
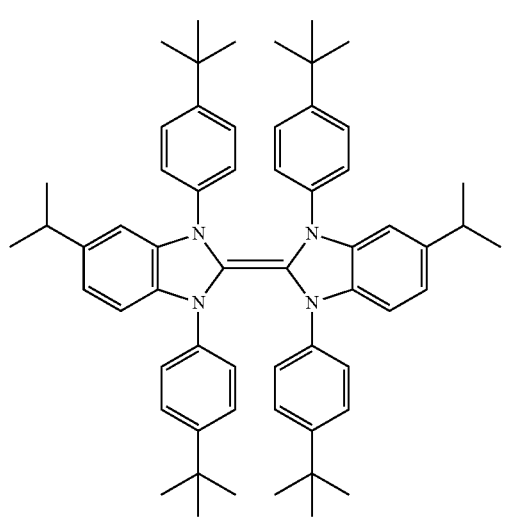
B31
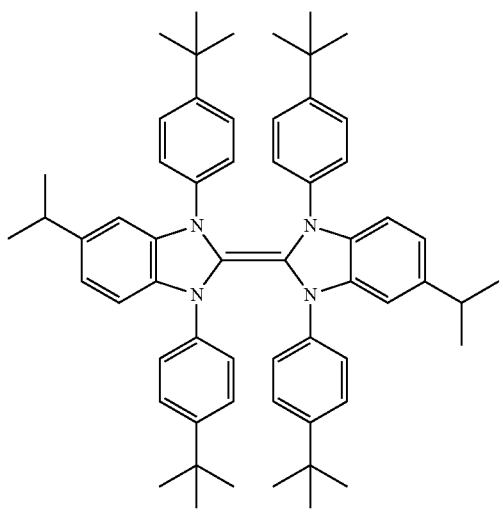
B32
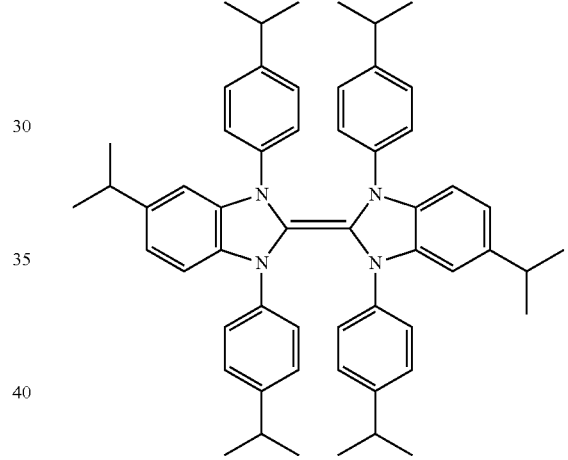
B33
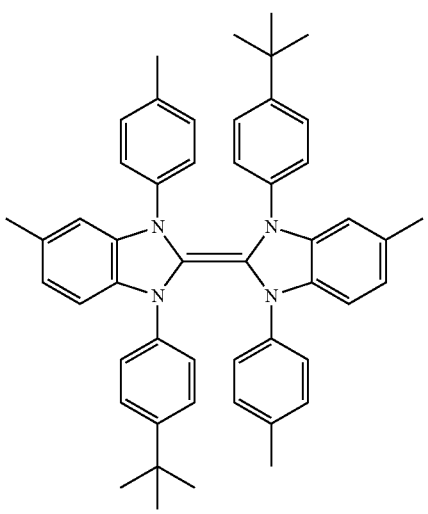

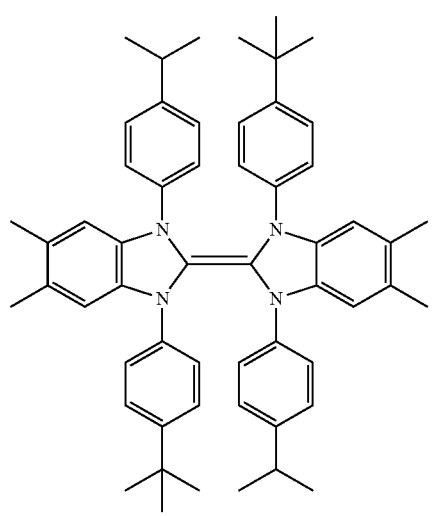
B34
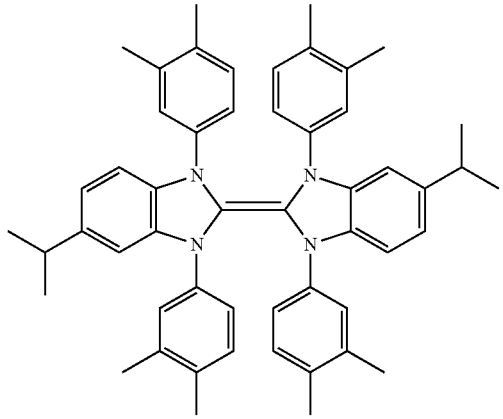
B37
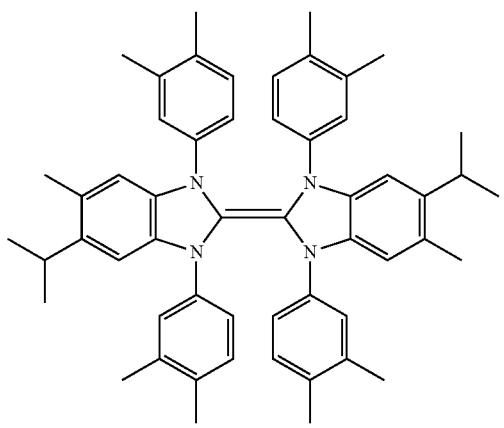
B35
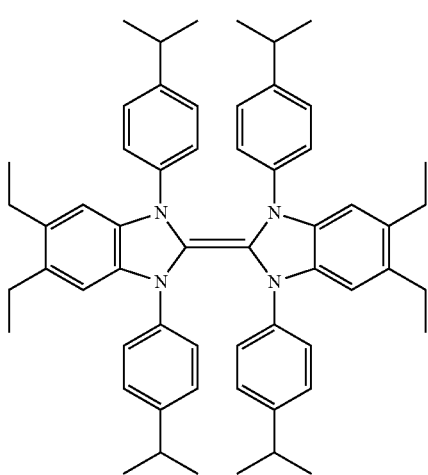
B38
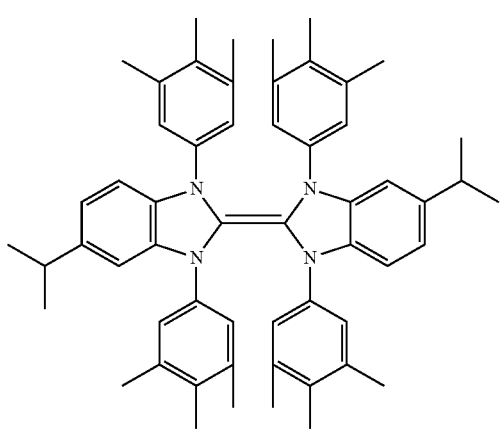
B36
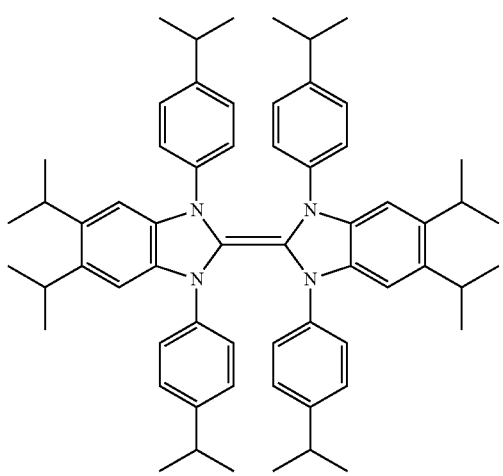
B39

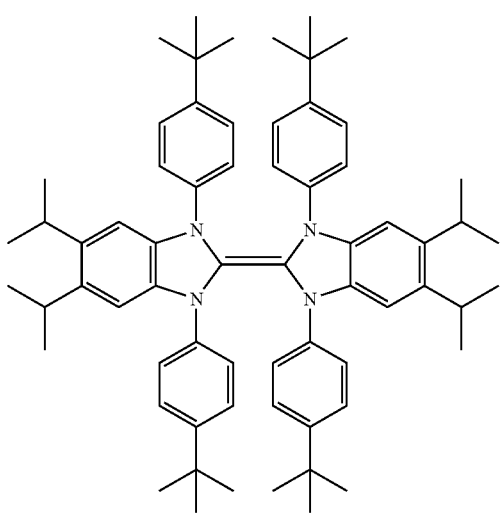
B40
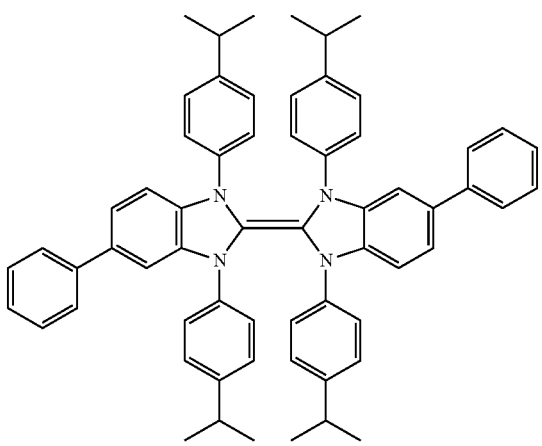
B43
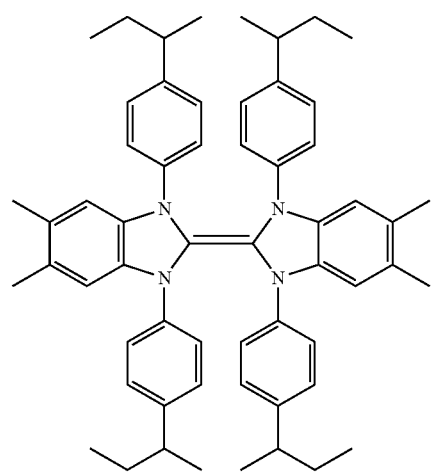
B41
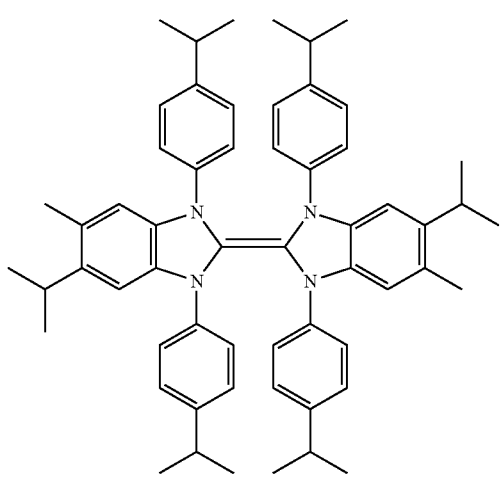
B44
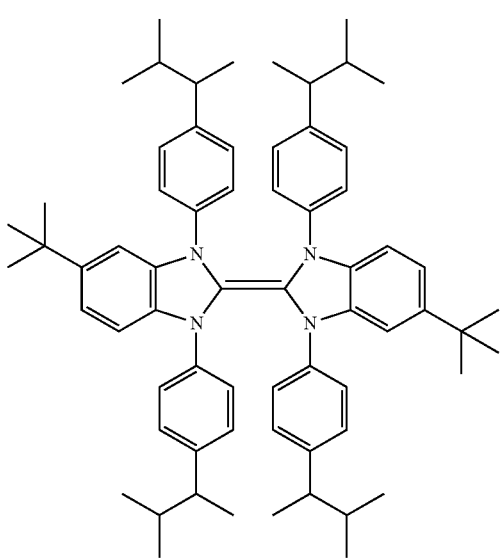
B42
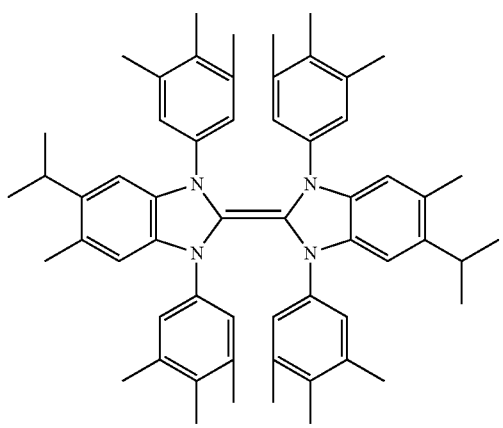
B45

-continued
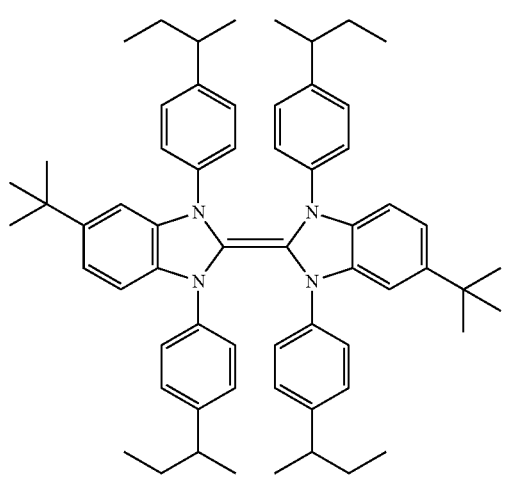 B46
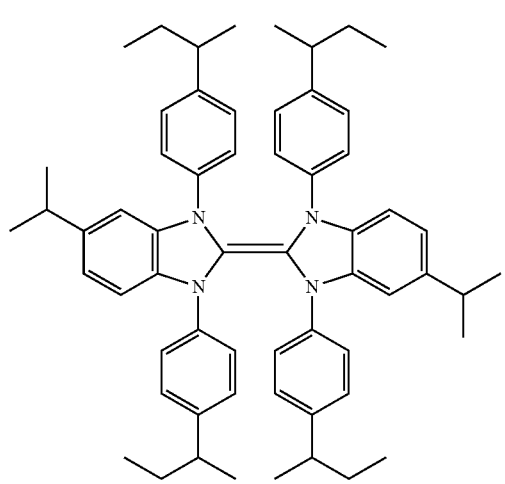 B47
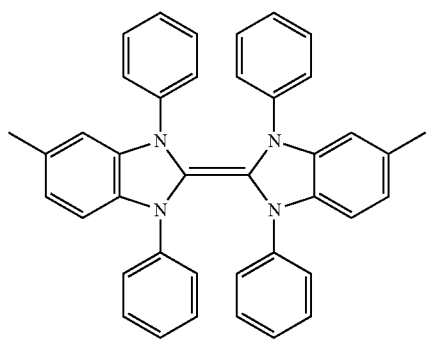 B48
-continued
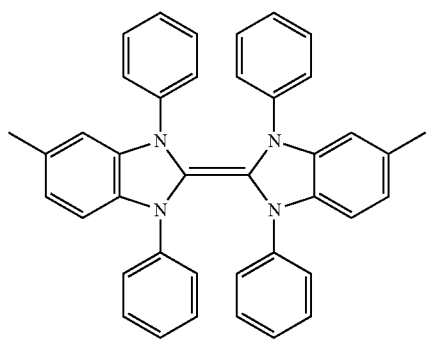 C1
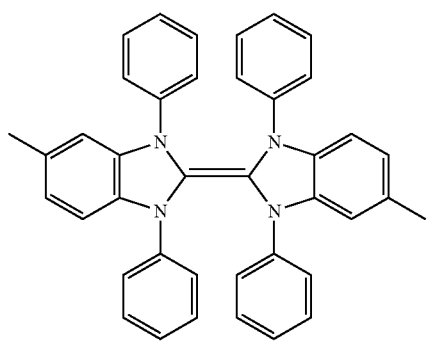 C2
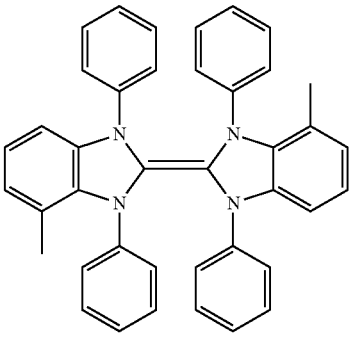 C3
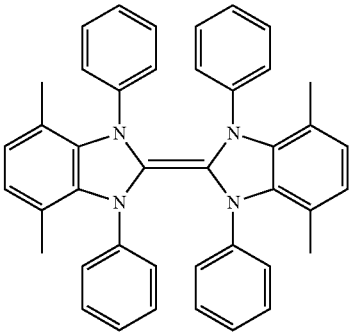 C4

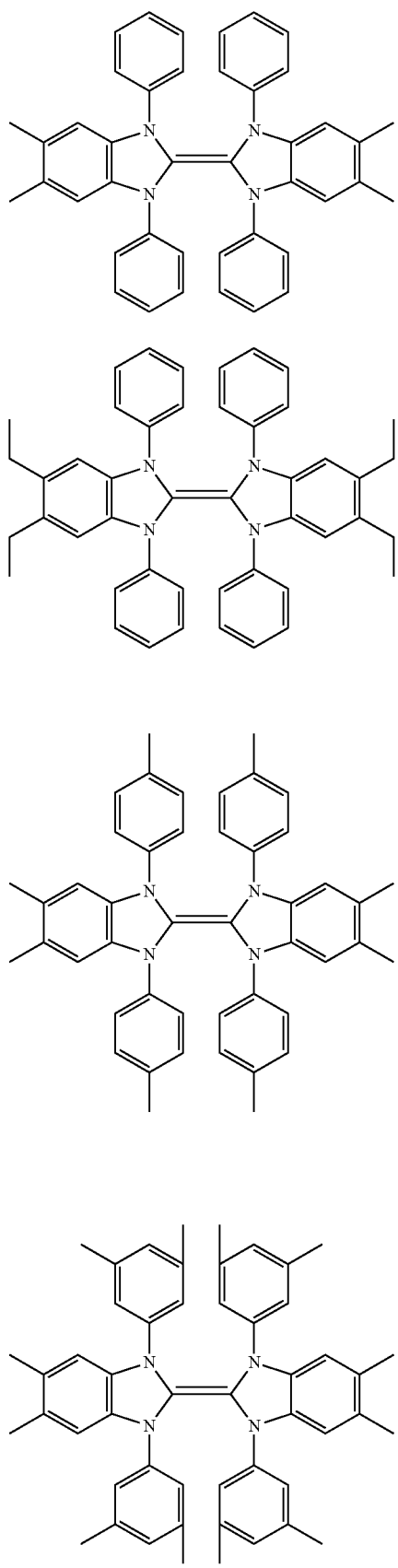
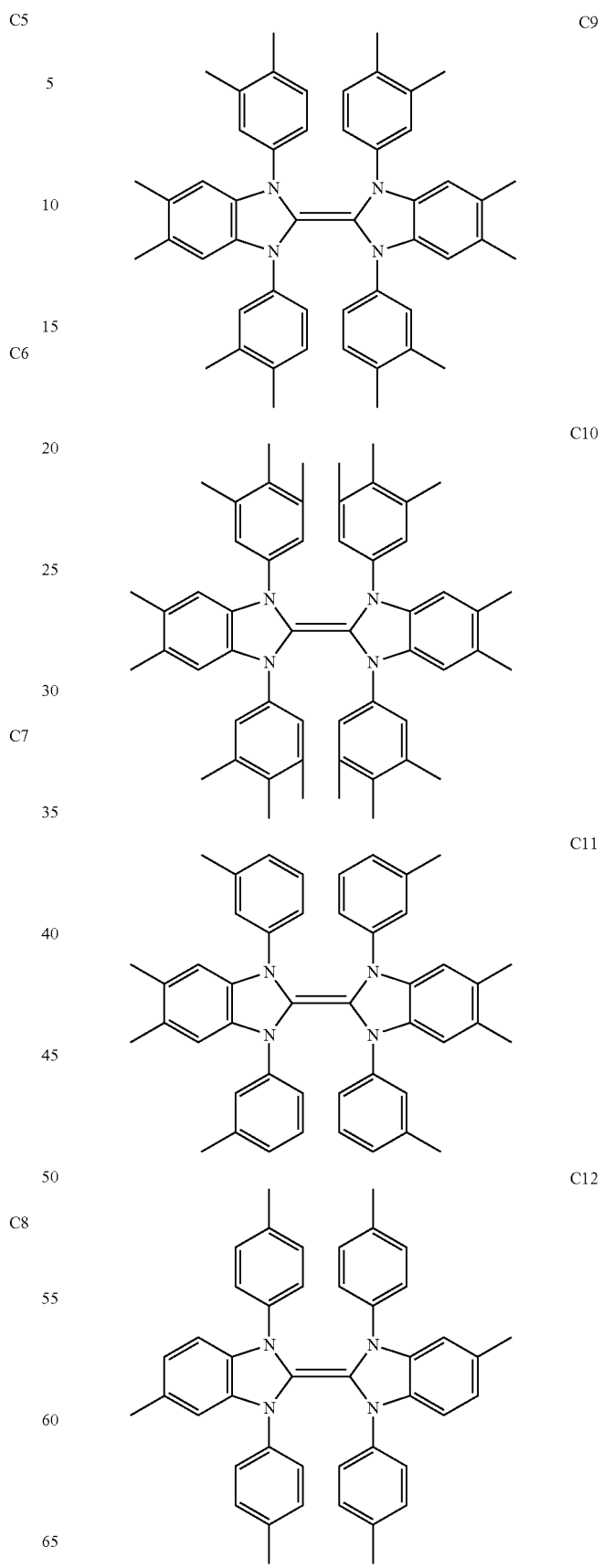

C13
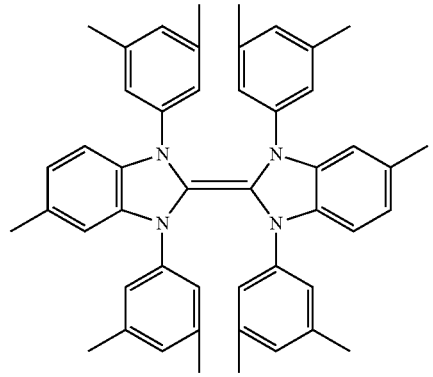
C14
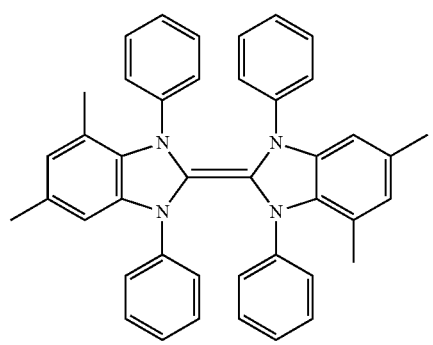
C15
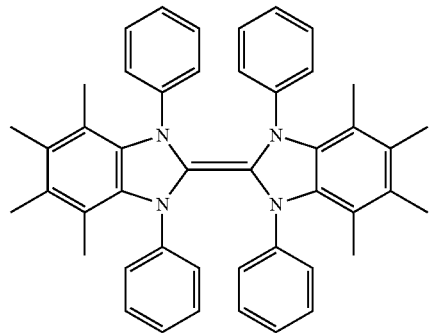
C16
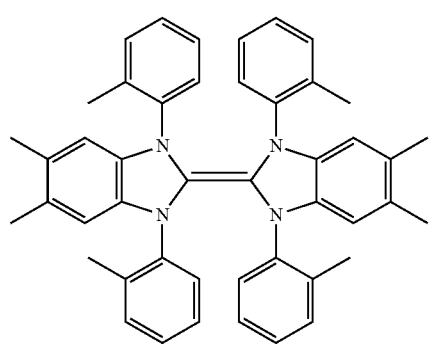
C17
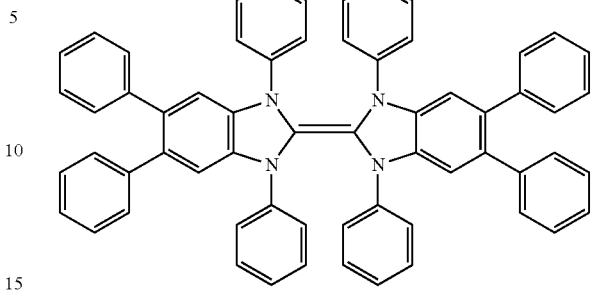
C18
C19

C20

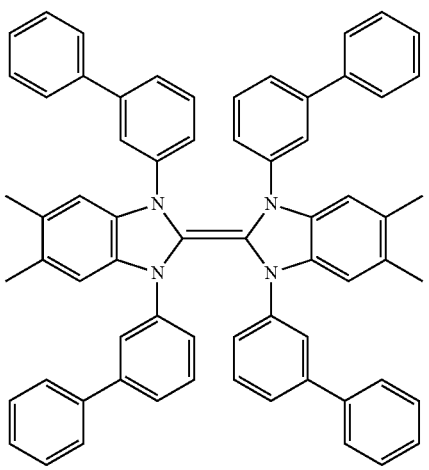

C21

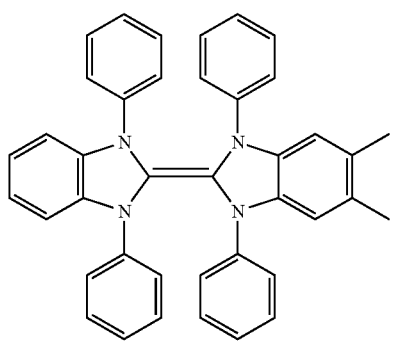

C22

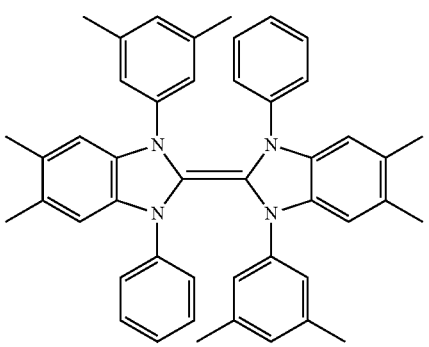

D1

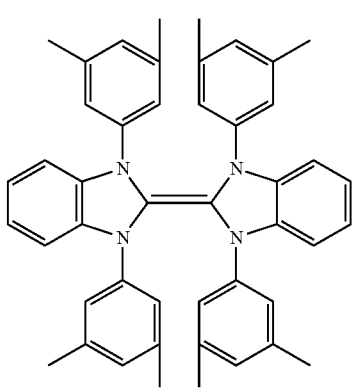

D2

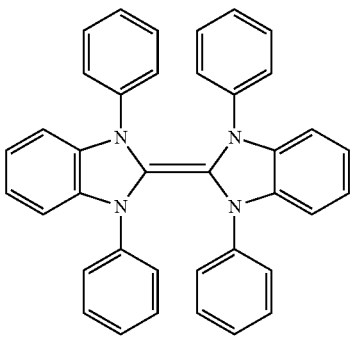

The organic compounds in group A of the illustrated compounds have phenyl groups substituted with fluorine atoms. This is an approach to improve the stability of 1,1',3,3'-tetraphenyl-2,2'-bibenzo[d]imidazolidene compounds by making their oxidation potential slightly high.

In other words, the organic compounds illustrated in group A are of high stability because they have a halogen atom in at least one of $R_1$ to $R_{10}$ and $R_{15}$ to $R_{24}$ in general formula (1). The halogen atom introduced as a substituent can be a fluorine atom.

The organic compounds in group B of the illustrated compounds has a tert-butyl group, an isobutyl group, or an isopropyl group in at least one of $R_1$ to $R_{28}$ in general formula (1).

In the case of compounds like those in group B, a bulky substituent introduced to the 1,1',3,3'-tetraphenyl-2,2'-bibenzo[d]imidazolidene compound prevents oxidation.

These compounds may be represented by structural formulae in which the two benzimidazolyl rings have line or point symmetry.

When an organic compound according to an embodiment has line symmetry, the axis of symmetry is a straight line perpendicular to the double bond connecting the benzimidazolyl rings of the compound. When an organic compound according to an embodiment has point symmetry, the center of symmetry is located on the double bond connecting the benzimidazolyl rings of the compound.

The organic compounds in group C of the illustrated compounds have a substituent in positions 4 to 7 and 4' to 7' of the 1,1',3,3'-tetrahydro-2,2'-bibenzo[d]imidazolidene skeleton. In other words, these compounds have a substituent in at least one of $R_{11}$ to $R_{14}$ and $R_{25}$ to $R_{28}$ in general formula (1).

The substituents in the illustrated compounds C are not bulky ones such as a tert-butyl group, an isobutyl group, or an isopropyl group. This is an approach to prevent oxidation by replacing a hydrogen atom at highly oxidizable sites with another, rather than by using a bulky substituent.

The organic compounds in group D of the illustrated compounds have phenyl groups substituted with an non-bulky substituent, such as a methyl group, in positions 1, 1', 3, and 3' of the 1,1',3,3'-tetrahydro-2,2'-bibenzo[d]imidazolidene skeleton. D2 is unsubstituted 1,1',3,3'-tetraphenyl-2,2'-bibenzo[d]imidazolidene.

These compounds are rather susceptible to oxidation compared with organic compounds according to an embodiment, but can be applied to field elements when used in isolation from the air. It would be, however, better to use the more stable organic compounds according to an embodiment.

Method for Synthesizing an Organic Compound According to an Embodiment

The following describes a method for synthesizing an organic compound according to an embodiment. An organic compound according to an embodiment can be synthesized through, for example, the reaction scheme below. $R_1$ and $R_2$ represent substituents introduced.

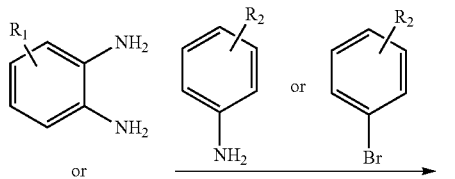

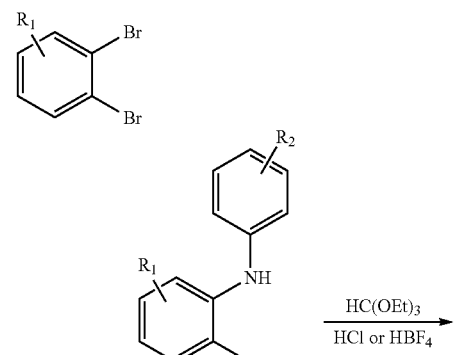

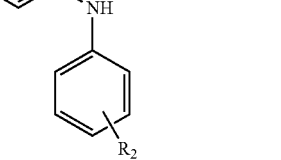

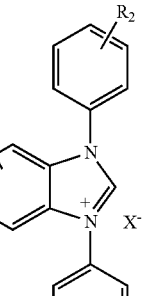

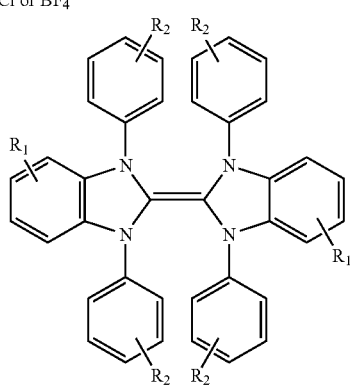

Organic Light-Emitting Elements According to an Embodiment

According to an embodiment, a field element has a pair of electrodes and an organic compound layer between the pair of electrodes. The organic compound layer contains an organic compound represented by general formula (2).

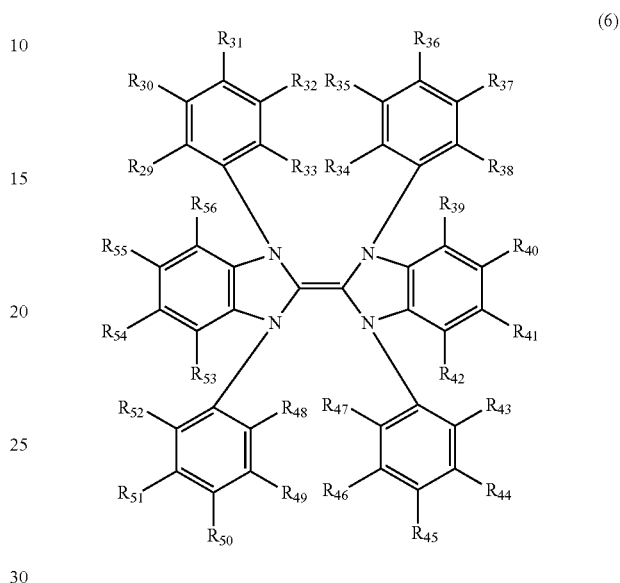

(6)

In formula (6), each of $R_{29}$ to $R_{56}$ represents a hydrogen atom and a substituent. The substituent is any of a halogen atom, an alkyl group containing 1 or more and 8 or less carbon atoms, and a substituted or unsubstituted aryl group.

Specific examples of alkyl groups containing 1 or more and 8 or less carbon atoms and specific examples of aryl groups for this formula are the same as those for general formula (1).

It is preferred that at least one of $R_{29}$ to $R_{56}$ be the substituent.

It is more preferred that at least one of $R_{39}$ to $R_{42}$ and $R_{53}$ to $R_{56}$, even more preferably $R_{40}$, $R_{41}$, $R_{54}$, and $R_{55}$, be an alkyl group containing 1 or more and 8 or less carbon atoms or a phenyl group.

Another preferred combination of substituents is any of a fluorine atom, a tert-butyl group, a sec-butyl group, an isobutyl group, and an isopropyl group located in at least one of $R_{29}$ to $R_{38}$ and $R_{43}$ to $R_{52}$ and hydrogen atoms in $R_{39}$ to $R_{42}$ and $R_{53}$ to $R_{56}$.

Compounds represented by general formula (2), which are capable of generating charge in field elements, can be used in field elements. The field elements as mentioned herein include elements such as organic light-emitting elements, organic solar cells, organic transistors, and organic piezoelectric elements.

An organic light-emitting element according to an embodiment has a pair of electrodes and an organic compound layer between the pair of electrodes. The organic compound layer contains an organic compound represented by general formula (2).

In an organic light-emitting element according to an embodiment, the organic compound layer may be a single layer or a multilayer body having multiple layers.

The organic compound layer may include, besides an emitting layer, layers such as a hole injection layer, a hole transport layer, an electron blocking layer, a hole blocking layer, an electron transport layer, and an electron injection layer. The emitting layer may be a single layer or a multilayer body having multiple layers.

In an organic light-emitting element according to an embodiment, at least one layer in the organic compound layer contains an organic compound according to an embodiment.

To be more specific, the organic compound according to an embodiment is contained in any of the aforementioned hole injection, hole transport, electron blocking, emitting, hole blocking, electron transport, and electron injection layers. It is preferred that the organic compound according to an embodiment be used in at least one of electron injection, electron transport, hole transport, and hole injection layers of the organic light-emitting element, more preferably the electron injection or electron transport layer, in particular, the electron injection layer.

An organic light-emitting element according to an embodiment may be an organic light-emitting element having an anode, a cathode, and an emitting layer between the anode and the cathode. The organic light-emitting element also has an organic compound layer between the cathode and the emitting layer. The organic compound layer contains an organic compound represented by general formula (1).

The organic compound layer between the cathode and the emitting layer may also be referred to as an electron transport layer or an electron injection layer. The organic compound layer may also be referred to as an electron injection layer when it is in contact with the cathode.

The organic compound according to an embodiment can be used alone, but may also be used in mixture with an additional compound of a different kind.

The weight proportion of this additional compound can be more than 0% by weight and 80% by weight or less, with the total weight of the organic compound layer between the cathode and the emitting layer defined as 100% by weight.

The additional compound may have a higher oxidation potential than the organic compound according to an embodiment.

The additional compound can be any of an anthraquinone derivative, a fluorene derivative, a naphthalene derivative, an indene derivative, a terphenyl derivative, an acenaphthofluoranthene derivative, an indenoperylene derivative, and a phenanthroline derivative.

Examples of structures of an organic light-emitting element according to an embodiment include multilayer structures in which the following electrodes and organic compound layers are stacked on a substrate in the indicated order.

(1) Anode/emitting layer/cathode
(2) Anode/hole transport layer/emitting layer/electron transport layer/cathode
(3) Anode/hole transport layer/emitting layer/electron transport layer/electron injection layer/cathode
(4) Anode/hole injection layer/hole transport layer/emitting layer/electron transport layer/cathode
(5) Anode/hole injection layer/hole transport layer/emitting layer/electron transport layer/electron injection layer/cathode
(6) Anode/hole transport layer/electron blocking layer/emitting layer/hole blocking layer/electron transport layer/cathode These element structures are merely basic ones. The structure of an organic light-emitting element in which a compound according to an embodiment is used is not limited to these.

Many other layer structures are also possible. For example, an insulating layer may exist in the interface between each electrode and an organic compound layer, there may be an adhesive or interfering layer, the electron or hole transport layer may be composed of two layers with different ionization potentials, the emitting layer may be composed of two layers with different emitting materials, and so forth.

The element may have the bottom-emission structure, in which light is emitted through the electrode on the substrate side, or the top-emission structure, in which light is emitted from the side opposite the substrate. The element may even have a structure such that light is emitted from both sides.

Structure (6), which includes both of electron and hole blocking layers, is preferred compared with the other listed element structures. Structure (6) provides a carrier leakage-free, high emission-efficiency light-emitting element by ensuring both carriers, i.e., holes and electrons, are confined to the emitting layer.

The emitting layer of an organic light-emitting element according to an embodiment may be composed of multiple ingredients that can be grouped into primary and secondary ingredients. The primary ingredient is the compound that has a weight proportion larger than that of any other compound constituting the emitting layer, and can be referred to as a host material.

All other compounds are secondary ingredients. The secondary ingredients can be referred to as a guest (dopant) material, an emission-assisting material, and a charge injection material. The emission-assisting material and the charge injection material, which are organic compounds, may share the same structure or have different structures. Although these materials are secondary ingredients, they can also be referred to as second host materials to distinguish them from the guest material.

The guest material is a compound that serves as the main light emitter in the emitting layer, whereas the host material, existing as a matrix around the guest material in the emitting layer, is a compound that serves mainly as a carrier transporter and a supplier of excitation energy to the guest material.

The concentration of the guest material is 0.01 wt % or more and less than 50 wt % of the total quantity of the constituents of the emitting layer, preferably 0.1 wt % or more and 20 wt % or less. Ensuring the concentration of the guest material is 10 wt % or less will prevent concentration quenching. The guest material may be distributed uniformly in the entire layer made of the host material or have a concentration gradient. There may even be a case where the guest material is contained only in a particular region in the host material layer.

The emitting layer may be a single layer or include multiple layers. It is also possible to blend colors by using an emitting material that emits light in two or more colors. The term "multiple layers" means that one emitting layer is stacked on another. The color of the light emitted from the organic light-emitting element in this situation ranges from blue to green to red, but the organic emitting layer may emit light in any color.

To be more specific, the color of light may be white or an intermediate color. White light can be produced with the use of emitting layers that emit lights in red, blue, and green. The emitting layer can be formed through a deposition or coating process.

The emitting layer of an organic light-emitting element according to an embodiment may contain multiple emitting materials. Two of the multiple emitting materials emit light in different colors. An element having these materials may emit white light.

An organic light-emitting element according to an embodiment may have multiple emitting layers, at least one of the multiple emitting layers configured to emit light with a wavelength different from those of the lights emitted from the other emitting layers. The organic light-emitting element may emit white light by blending lights from the emitting layers.

In an embodiment, a hole blocking layer refers to a layer that blocks holes, and a layer contiguous to the cathode side of the emitting layer is referred to as a hole blocking layer.

Compounds other than the organic compound according to an embodiment may optionally be used, including known low-molecular-weight and polymeric emitting materials, hole-injecting or hole-transporting compounds, compounds for use as host materials, luminescent compounds, and electron-injecting or electron-transporting compounds.

The following provides examples of these compounds.

The use of a material with high hole mobility as a hole-injecting/transporting material helps the injection of holes from the anode and ensures the injected holes are transported to the emitting layer. The hole-injecting/transporting material can also be a material with a high glass-transition temperature so that crystallization or other forms of qualitative deterioration of layers in the organic light-emitting element will be prevented. Examples of low-molecular-weight and polymeric materials having hole-injecting/transporting properties include triarylamine derivatives, aryl carbazole derivatives, phenylene diamine derivatives, stilbene derivatives, phthalocyanine derivatives, porphyrin derivatives, polyvinyl carbazole), poly(thiophene), and other electroconductive polymers. These hole-injecting/transporting materials are also suitable for use in an electron blocking layer.

Specific examples of compounds that can be used as hole-injecting/transporting materials include, but are not limited to, the following.

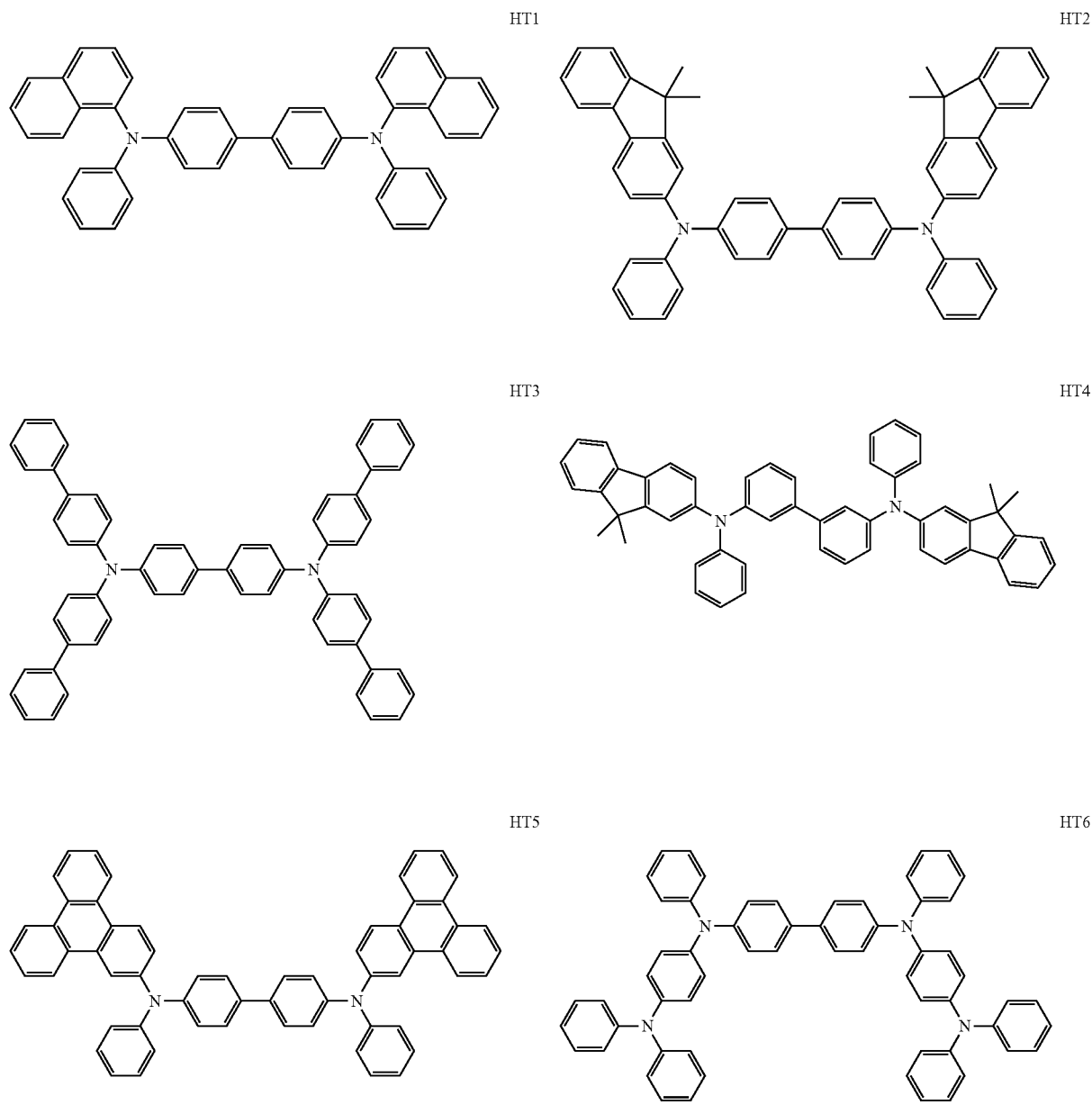

-continued
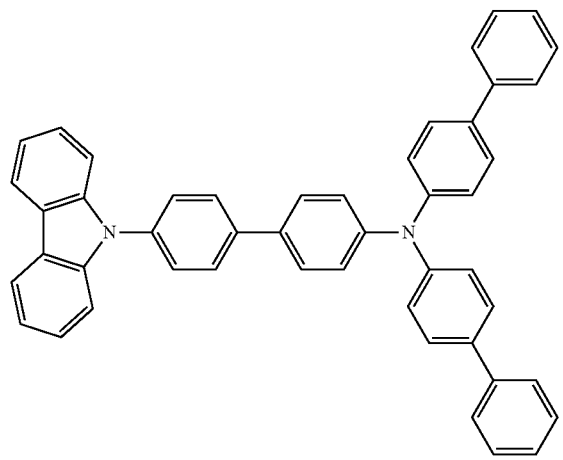
HT7
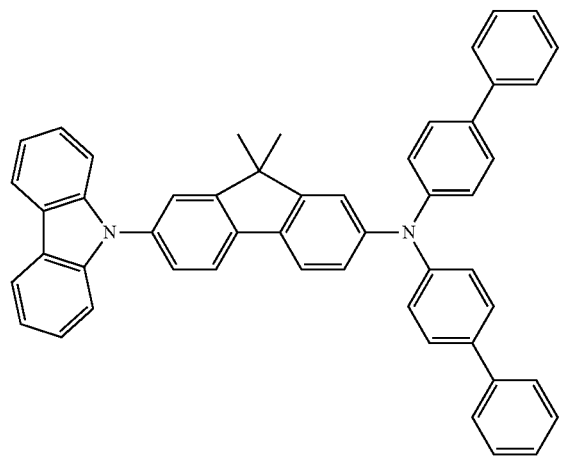
HT8
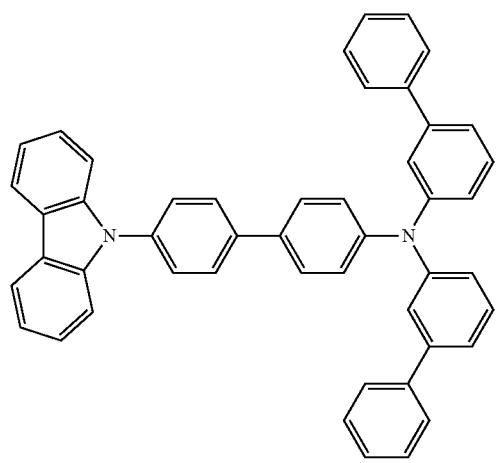
HT9
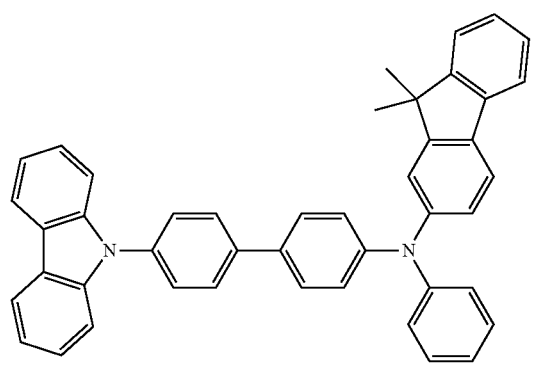
HT10
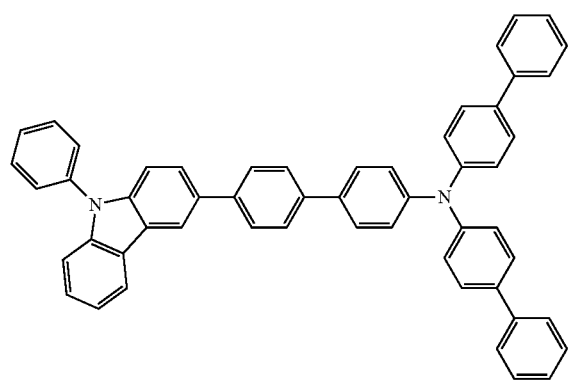
HT11
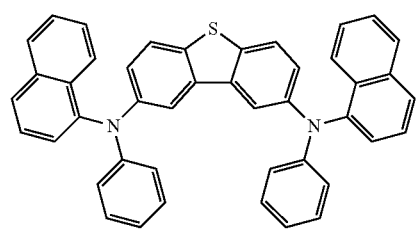
HT12

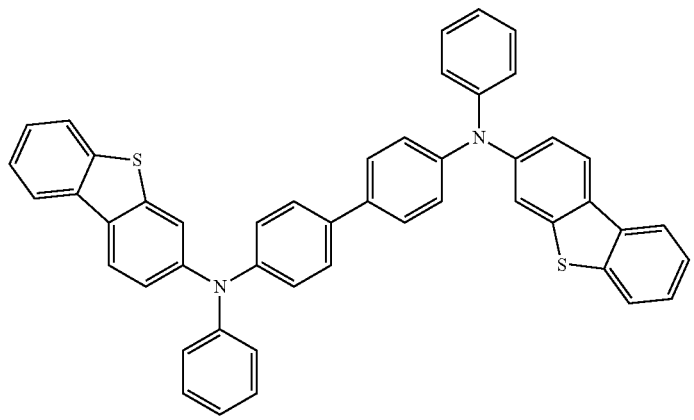

HT13

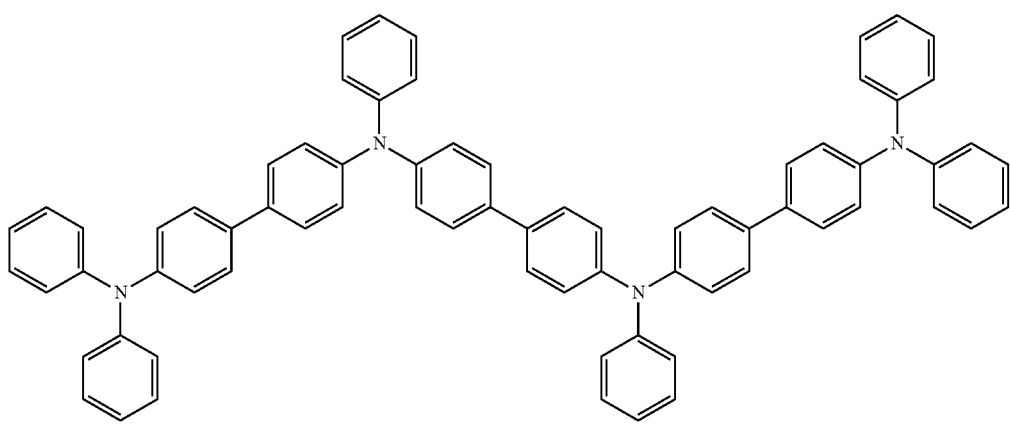

HT14

Examples of emitting materials, which are responsible mainly for light-emitting function, include polycyclic compounds (e.g., fluorene derivatives, naphthalene derivatives, pyrene derivatives, perylene derivatives, tetracene derivatives, anthracene derivatives, and rubrene), quinacridone derivatives, coumarin derivatives, stilbene derivatives, organic aluminum complexes such as tris(8-quinolinolato) aluminum, iridium complexes, platinum complexes, rhenium complexes, copper complexes, europium complexes, ruthenium complexes, and polymer derivatives such as poly(phenylene vinylene) derivatives, poly(fluorene) derivatives, and poly(phenylene) derivatives.

Specific examples of compounds that can be used as emitting materials include, but are not limited to, the following.

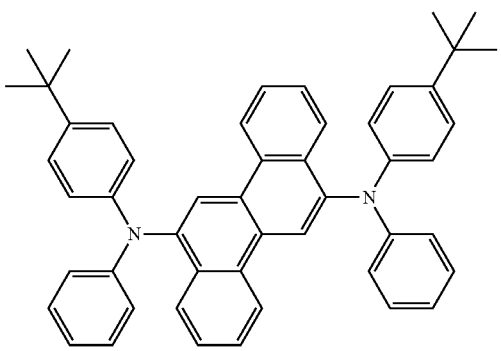

BD1

BD2
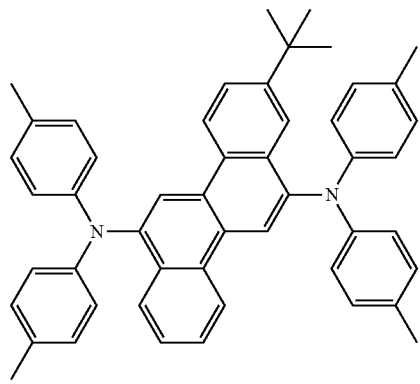
BD3
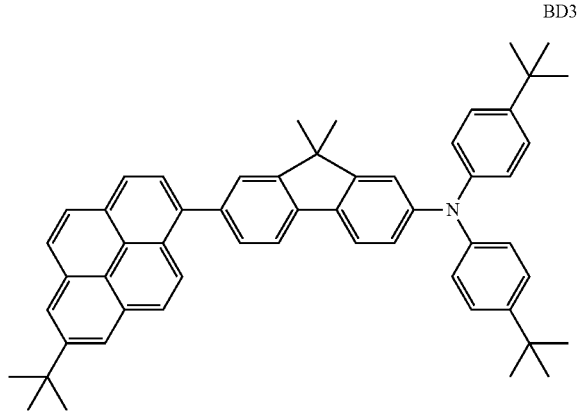
BD4
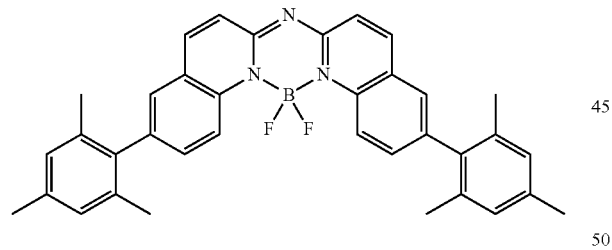
BD5
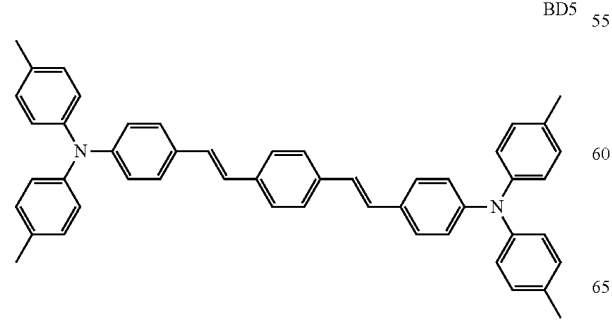
BD6
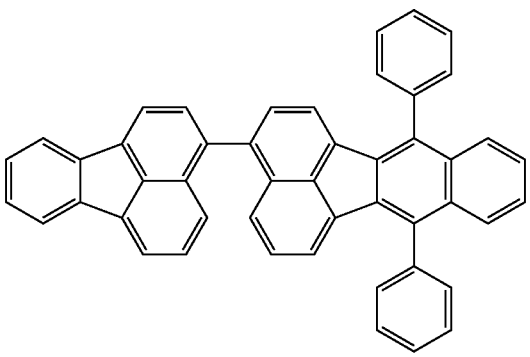
BD7
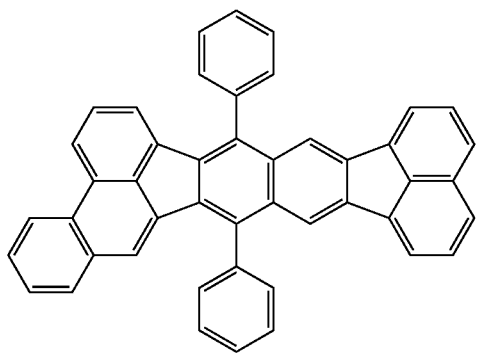
BD8
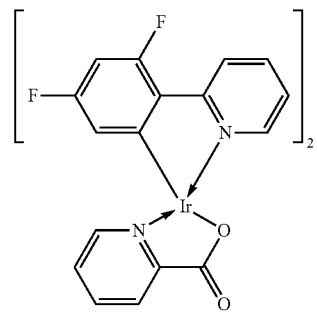
GD1
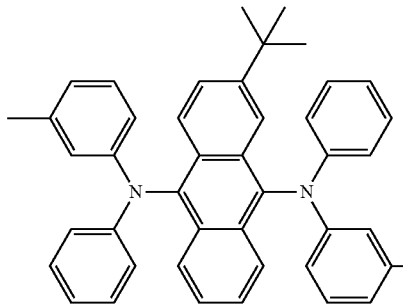
GD2
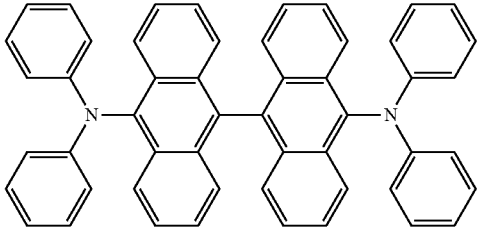

GD3 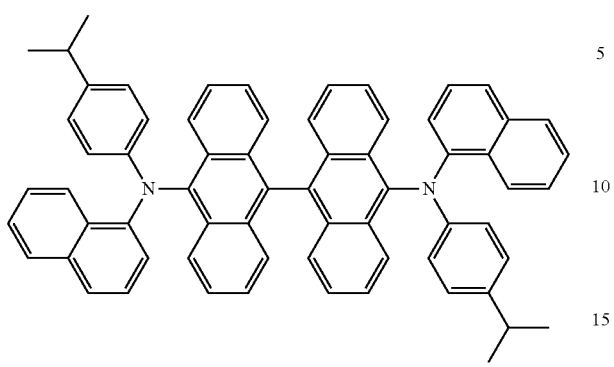
GD4 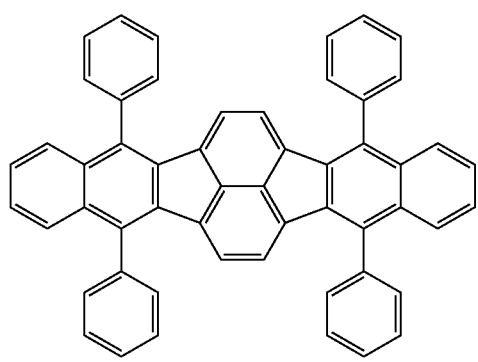
GD5 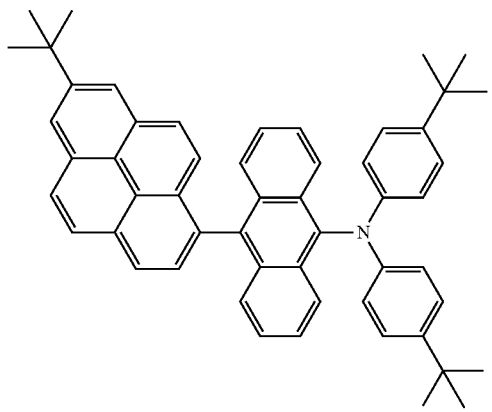
GD6 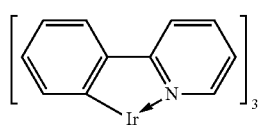
GD7 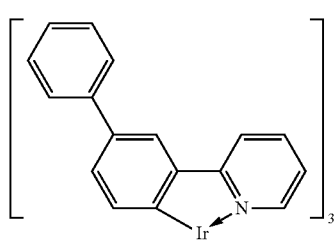
GD8 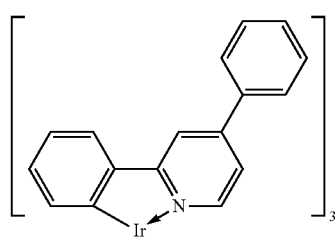
RD1 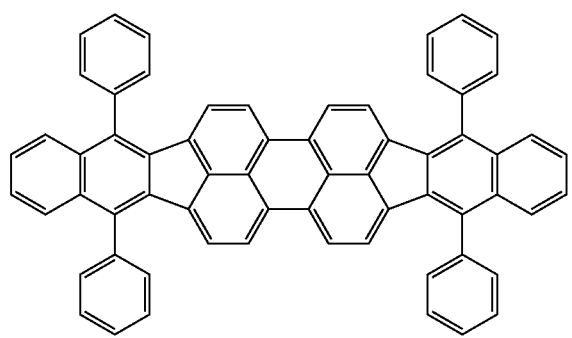
RD2 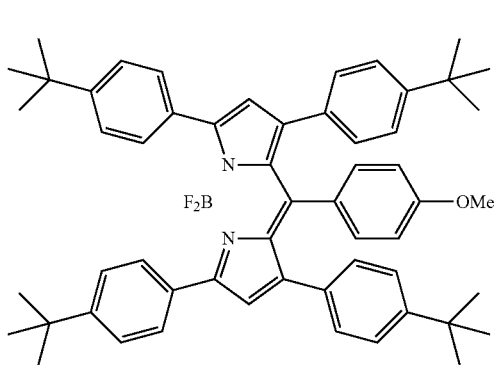
RD3 
RD4 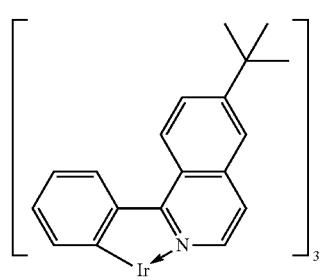

RD5

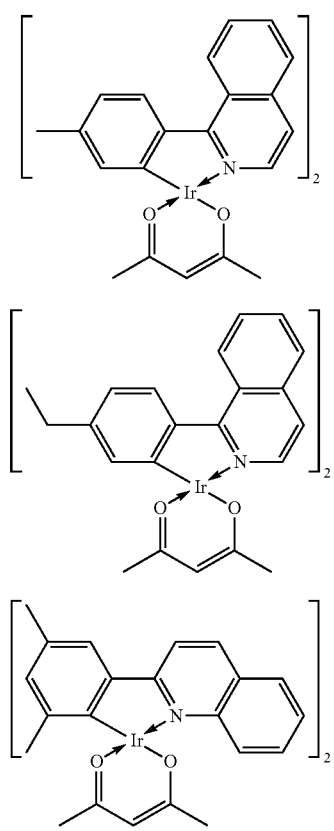

RD6

RD7

RD8

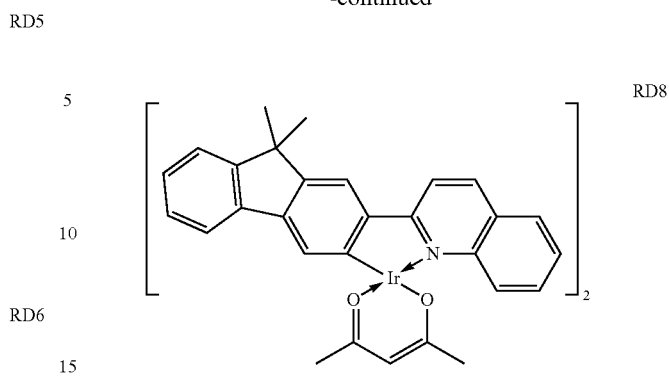

Examples of emitting-layer host or emission-assisting materials in the emitting layer include, besides aromatic hydrocarbon compounds and their derivatives, carbazole derivatives, dibenzofuran derivatives, dibenzothiophene derivatives, organic aluminum complexes such as tris(8-quinolinolato)aluminum, and organic beryllium complexes.

Specific examples of compounds that can be used as emitting-layer host or emission-assisting materials in the emitting layer include, but are not limited to, the following.

EM1

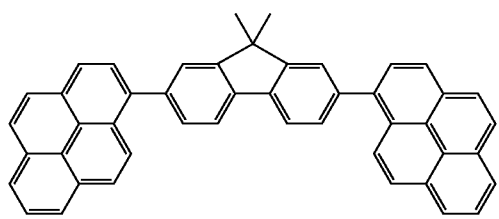

EM2

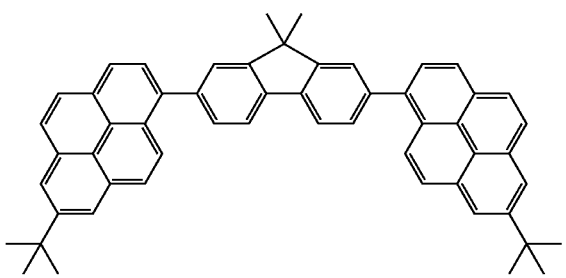

EM3

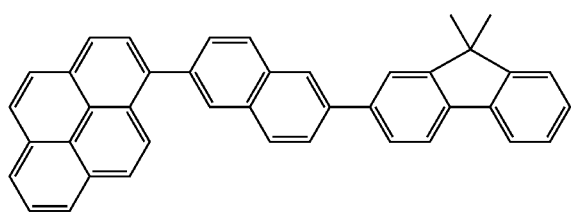

EM4

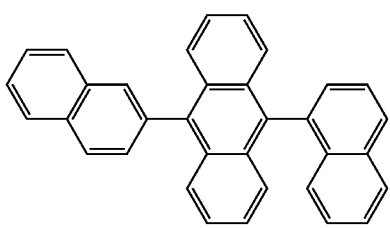

-continued
EM5
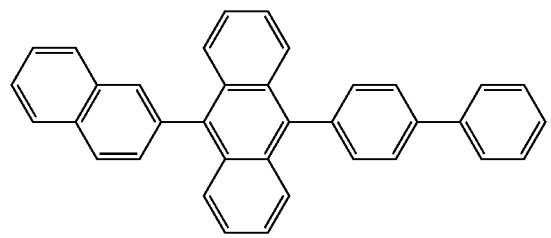
EM6
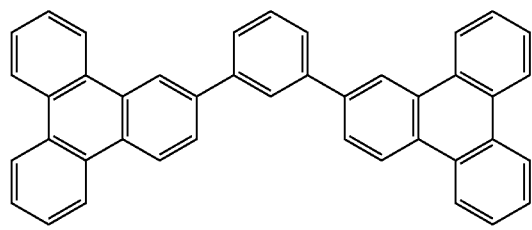
EM7
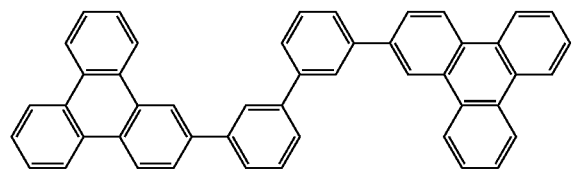
EM8
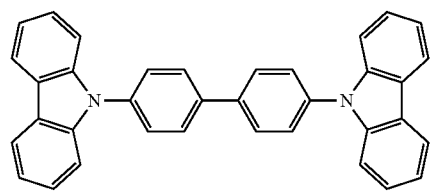
EM9
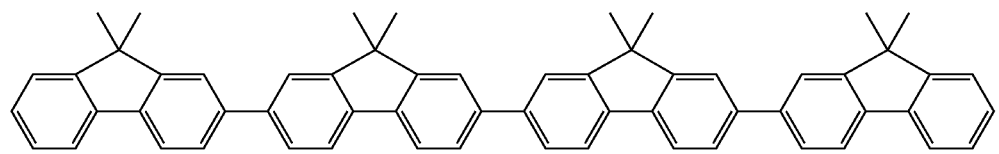
EM10
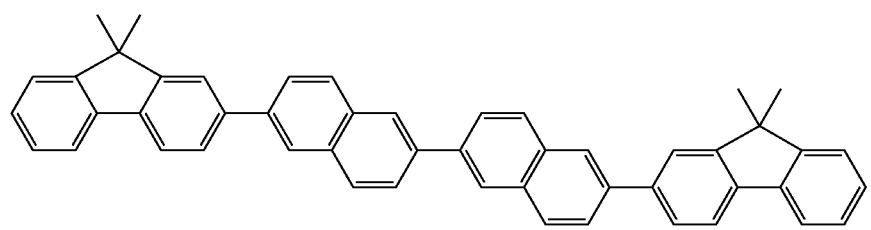
EM11
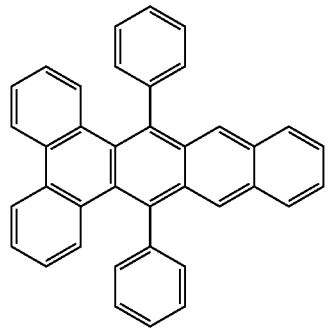
EM12
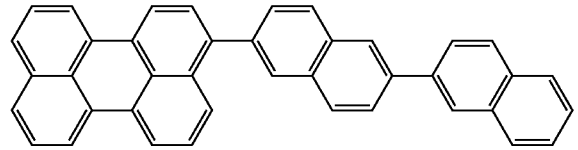
EM13
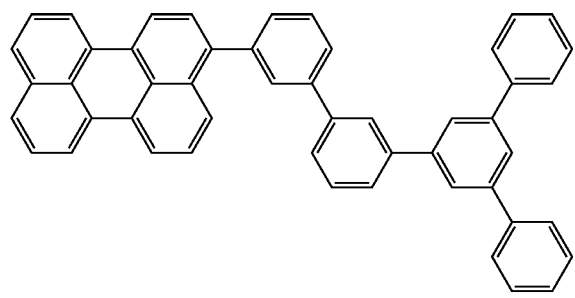
EM14
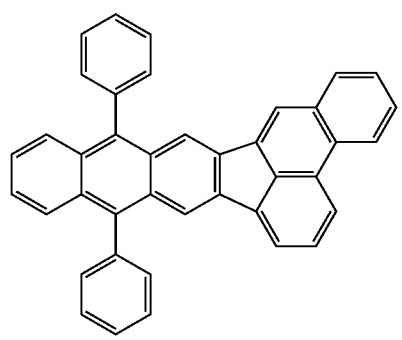

EM15
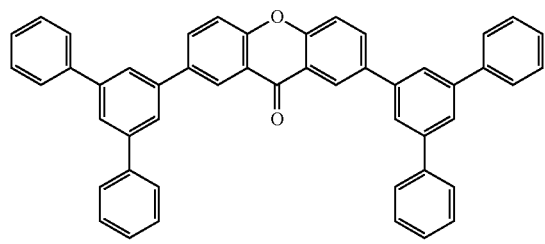

EM16
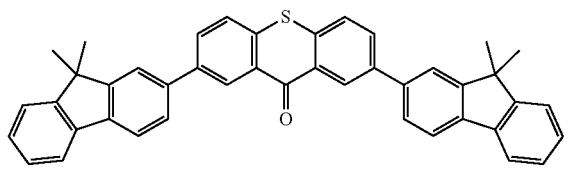

EM17
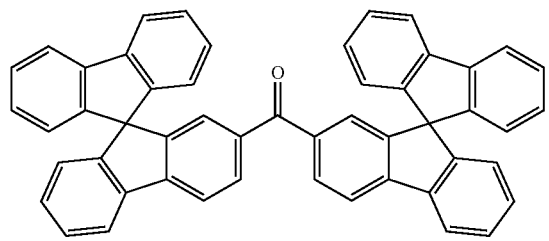

The electron-transporting material can be any compound capable of transporting electrons injected from the cathode to the light-emitting layer, and is selected in consideration of conditions such as the balance with the mobility of holes in the hole-transporting material. Examples of materials capable of transporting electrons include oxadiazole derivatives, oxazole derivatives, pyrazine derivatives, triazole derivatives, triazine derivatives, quinoline derivatives, quinoxaline derivatives, phenanthroline derivatives, organic aluminum complexes, and polycyclic compounds (e.g., fluorene derivatives, naphthalene derivatives, chrysene derivatives, and anthracene derivatives). These electron-transporting materials are also suitable for use in a hole blocking layer.

Specific examples of compounds that can be used as electron-transporting materials include, but are not limited to, the following.

ET1
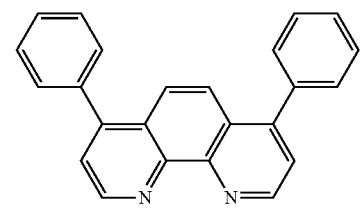

ET2
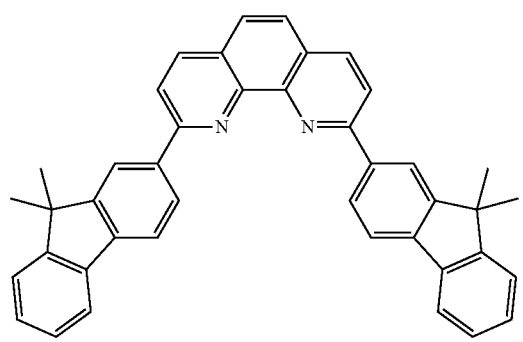

ET3
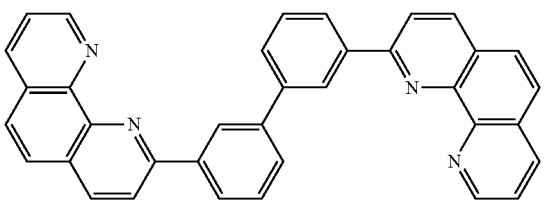

ET4
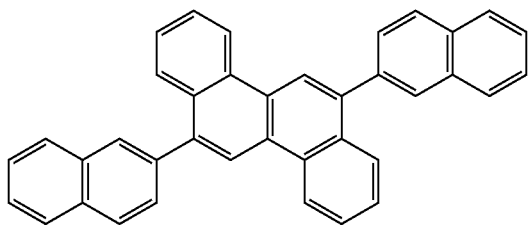

ET5

ET6 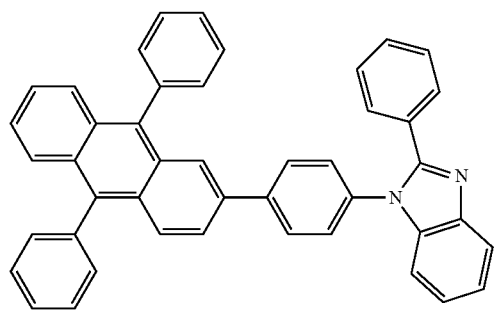

ET7 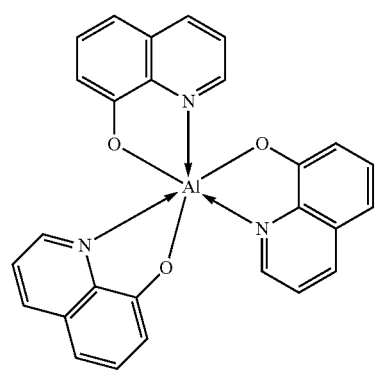

ET8 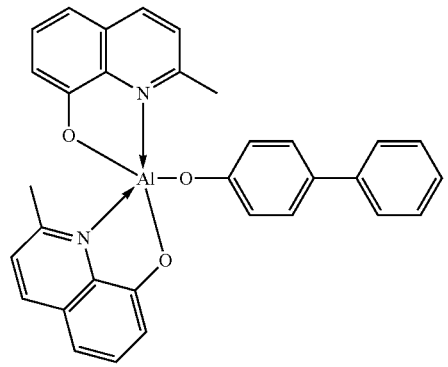

ET9 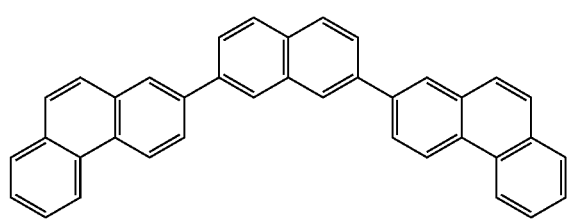

ET10 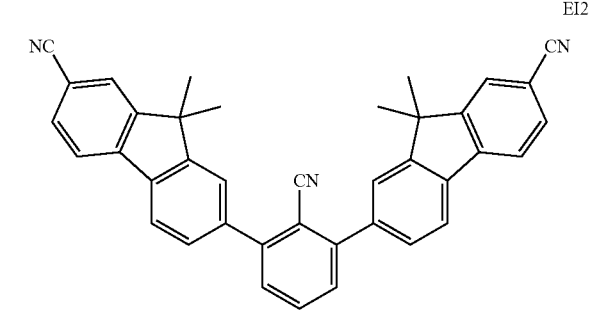

The electron-injecting material can be any compound that helps the injection of electrons from the cathode and is selected in consideration of conditions such as the balance with hole injection. The 1,1',3,3-tetraphenyl-2,2'-bibenzo[d]imidazolidene compound illustrated as an embodiment may be used as a mixture with an electron transport material, and may also be used as a mixture with the materials illustrated below which have a cyano group, a fluorine atom, or a fluoranthene skeleton or containing a polycyclic structure. When mixed with the imidazolidene compound, these electron transport materials are additional compounds in the organic compound layer.

EI1 

EI2 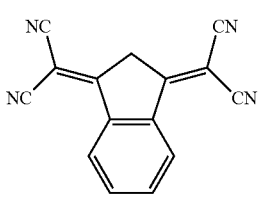

EI3 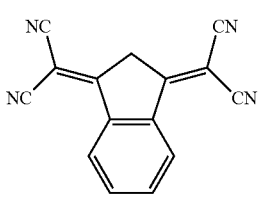

-continued
EI4
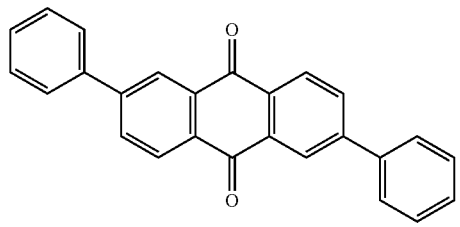
EI5
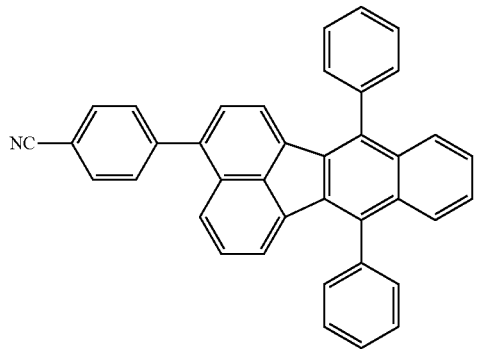
EI6
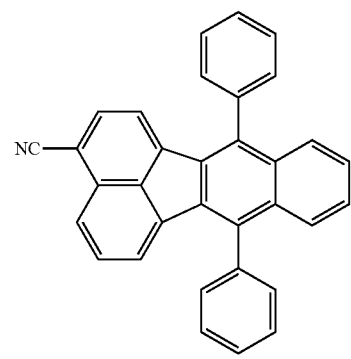
EI7
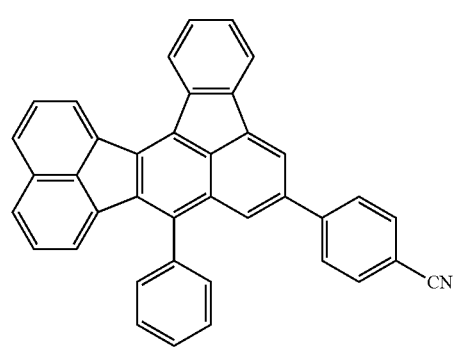
EI8
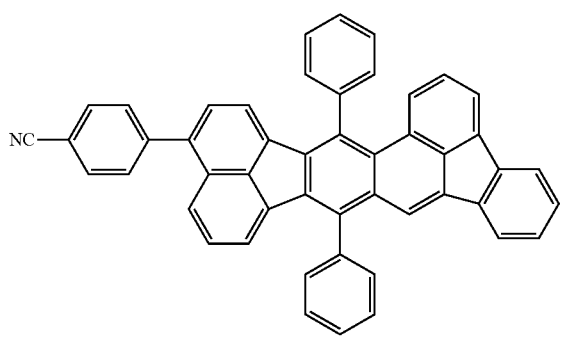
-continued
EI9
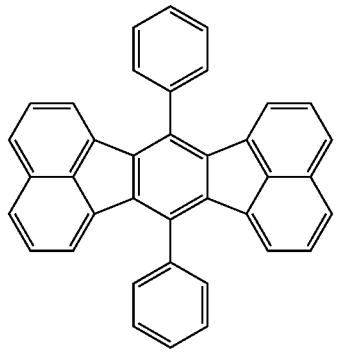
EI10
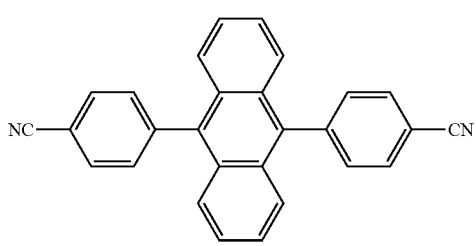
EI11
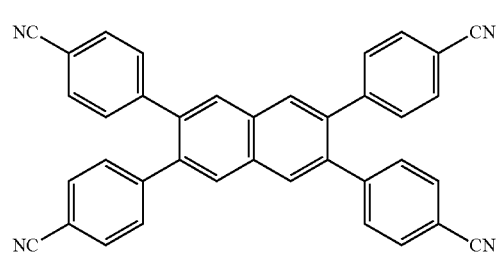
EI12
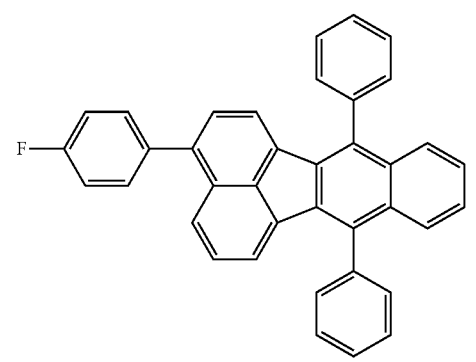
EI13
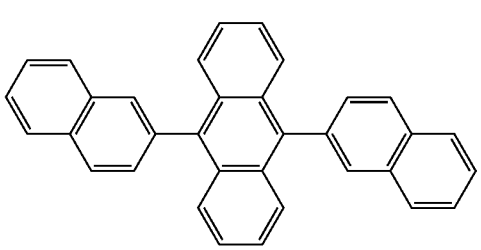

-continued

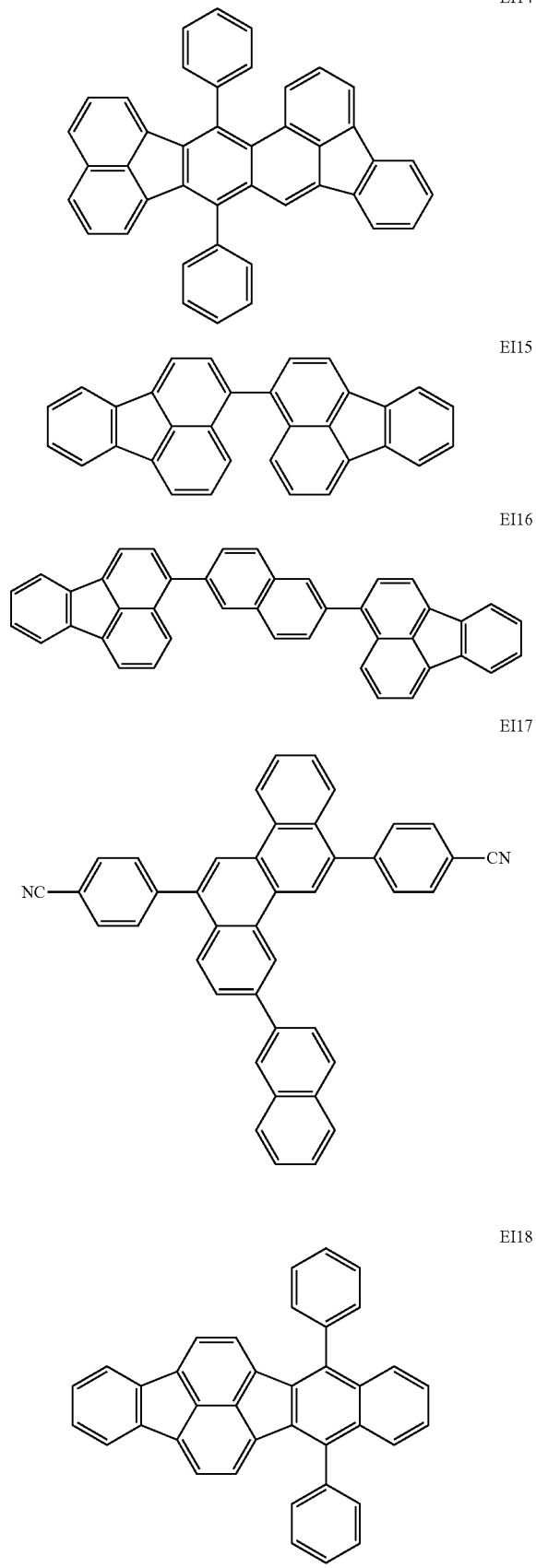

EI14

EI15

EI16

EI17

EI18

-continued

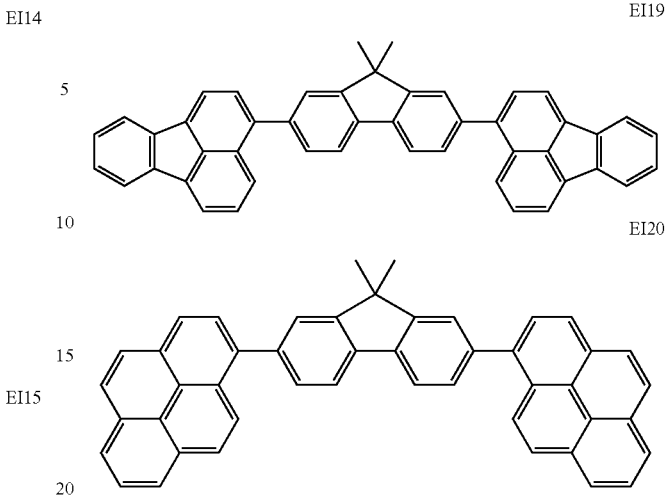

EI19

EI20

The anode can be made of a material having a large work function. Examples include elementary metals such as gold, platinum, silver, copper, nickel, palladium, cobalt, selenium, vanadium, and tungsten, mixtures containing these elementary metals, alloys of these elementary metals, and metal oxides such as tin oxide, zinc oxide, indium oxide, indium tin oxide (ITO), and indium zinc oxide. Electroconductive polymers such as polyaniline, polypyrrole, and polythiophene can also be used.

These electrode materials can be used alone, and it is also possible to use a combination of two or more of them. The anode may be a single layer or include multiple layers.

The cathode can be made of a material having a low work function. Examples include alkali metals such as lithium, alkaline earth metals such as calcium, elementary metals such as aluminum, titanium, manganese, silver, lead, chromium, and mixtures containing these elementary metals. Alloys of these elementary metals can also be used, examples including magnesium-silver, aluminum-lithium, aluminum-magnesium, silver-copper, and zinc-silver. It is also possible to use a metal oxide such as indium tin oxide (ITO). These electrode materials can be used alone, and it is also possible to use a combination of two or more of them. The cathode may have a monolayer or multilayer structure.

Organic compound layers in an organic light-emitting element according to an embodiment (e.g., a hole injection layer, a hole transport layer, an electron blocking layer, an emitting layer, a hole blocking layer, an electron transport layer, and an electron injection layer) can be formed using a method described below.

An organic compound layer in an organic light-emitting element according to an embodiment can be formed using a dry process, such as vacuum deposition, ion deposition, sputtering, and plasma deposition. It is also possible to use a wet process, in which a solution of the material in an appropriate solvent is applied using a known coating technique (e.g., spin coating, dipping, casting, the LB technique, or inkjet printing) to form the layer.

Forming the layer using a technique like vacuum deposition or solution coating reduces the risk of deterioration such as crystallization, making the layer highly stable over time. When the layer is formed using coating, the solution may be used in combination with an appropriate binder resin.

The binder resin can be, but is not limited to, polyvinyl carbazole resin, poly-carbonate resin, polyester resin, ABS resin, acrylic resin, polyimide resin, phenolic resin, epoxy resin, silicone resin, and urea resin.

These binder resins may be used in the form of a single homopolymer or copolymer, and it is also possible to use a mixture of two or more of them. Known additives, such as plasticizers, antioxidants, and ultraviolet absorbers, may optionally be used.

Applications of an Organic Light-Emitting Element According to an Embodiment

An organic light-emitting element according to an embodiment can be used as a component of a display apparatus or a lighting apparatus. Other applications include a light source for exposure in an electrophotographic image-forming apparatus, a backlight in a liquid-crystal display apparatus, and a lighting apparatus having a source of white light and a color filter. An example of the color filter is a filter that allows one of the three colors of red, green, and blue to pass through.

A display apparatus according to an embodiment has multiple pixels at least one of which has an organic light-emitting element according to an embodiment. This pixel has an active element besides the organic light-emitting element according to an embodiment. The active element is, for example, a switching element or an amplifying element, more specifically a transistor. The anode or cathode of this organic light-emitting element is electrically coupled with the drain or source electrode of the transistor. The transistor may have an oxide semiconductor in its active region. The oxide semiconductor can be an amorphous, crystalline, or hybrid semiconductor. A crystalline oxide semiconductor may be monocrystalline, microcrystalline, or oriented (C axis or any other particular axis) or even a mixture of at least two or more of these phases.

An organic light-emitting apparatus having such a switching element can be used as an image display apparatus in which the pixels are organic light-emitting elements or as a lighting apparatus. It is also possible to use such an organic light-emitting apparatus as a light source to expose a photosensitive element in an electrophotographic image-forming apparatus, such as a laser beam printer or a photocopier.

The display apparatus can be used as an image display apparatus for PCs or similar. An example of the aforementioned transistor is a TFT element, and this TFT element is provided on, for example, an insulating surface of a substrate.

The display apparatus can be an image information-processing apparatus having an image input unit configured to receive image information from an area or linear CCD sensor, a memory card, or any other source, an information-processing unit configured to process the input information, and a display unit configured to display the input image.

The display unit of an imaging apparatus or an inkjet printer may have a touchscreen feature. The mode of driving on which the touchscreen feature works is not critical. The touchscreen feature can be an infrared, electrostatic capacitive, resistive, or electromagnetic inductive touch screen, preferably an electrostatic capacitive or electromagnetic inductive touchscreen.

The display apparatus may also be used in the display unit of a multifunctional printer.

The lighting apparatus can be, for example, a room lighting fixture. The lighting apparatus may produce light in white (a color temperature of 4200 K), day white (a color temperature of 5000 K), or any color in the range of blue to red. It is only required that at least one of the organic light-emitting elements the lighting apparatus has be an organic light-emitting element according to an embodiment.

A lighting apparatus according to an embodiment has an organic light-emitting element according to an embodiment and an AC-DC converter coupled to the organic light-emitting element. The AC-DC converter is a circuit configured to convert alternating-current voltage to direct-current voltage. The converter also supplies driving voltage for the organic light-emitting element. The lighting apparatus may optionally have a color filter.

A lighting apparatus according to an embodiment may have a heat dissipation unit. The heat dissipation unit dissipates heat out of the apparatus, examples including metals with high specific heats and liquid silicone. When the heat dissipation unit is liquid silicone, the liquid silicone dissipates heat by flowing.

An image-forming apparatus according to an embodiment has a photosensitive element, a charging unit configured to charge the surface of the photosensitive element, an exposure unit configured to expose the photosensitive element, and a development unit configured to apply a developer to the photosensitive element. The exposure unit of the image-forming apparatus has multiple organic light-emitting elements according to an embodiment. The developer is, for example, toner or ink. The toner can be a dry or liquid toner.

An organic light-emitting element according to an embodiment can be used as a component an exposure apparatus configured to expose a photosensitive element. An exposure apparatus having an organic light-emitting element according to an embodiment has multiple emitting points, at least one of the emitting points having an organic light-emitting element according to an embodiment. The emitting points are arranged in a line in the longitudinal direction of the photosensitive element.

The following describes a display apparatus according to an embodiment with reference to a drawing. FIG. 1 is a schematic cross-sectional diagram illustrating an example of a display apparatus having organic light-emitting elements and TFT elements coupled to the organic light-emitting elements. The TFT elements are an example of active elements.

The display apparatus 1 in FIG. 1 has a substrate 11, which is a glass substrate or similar, and an anti-moisture film 12 on the top thereof, the anti-moisture film 12 configured to protect the TFT elements or an organic compound layer. The display apparatus 1 also has a metallic gate electrode 13, a gate insulating film 14, and a semiconductor layer 15.

A TFT element 18 has the semiconductor layer 15, a drain electrode 16, and a source electrode 17. There is an insulating film 19 on the top of the TFT element 18. The source electrode 17 is coupled to an anode 21 as a component of an organic light-emitting element via a contact hole 20.

The way of electric coupling between the electrodes of the organic light-emitting elements (an anode and a cathode) and the electrodes of the TFTs (source and drain electrodes) is not limited to that in FIG. 1. It is only required that either the anode or the cathode be electrically coupled to either the source or drain electrode of the TFT elements.

Although the organic compound layer in the display apparatus in FIG. 1 looks like a single layer, the organic compound layer 22 may include multiple layers. There are a first protective layer 24 and a second protective layer 25 on the cathode 23 to reduce the deterioration of the organic light-emitting elements.

Although in the display apparatus 1 in FIG. 1 transistors are used as switching elements, MIM elements may be used as switching elements instead.

Transistors that can be used in the display apparatus 1 in FIG. 1 are not limited to transistors on a monocrystalline silicon wafer and can be thin-film transistors having an active layer on an insulating surface of a substrate. The active layer can be made of, for example, monocrystalline silicon, non-monocrystalline silicon, such as amorphous or microcrystalline silicon, or a non-monocrystalline oxide semiconductor, such as indium zinc oxide or gallium zinc oxide. Thin-film transistors are also referred to as TFT elements.

The transistors in the display apparatus 1 in FIG. 1 may be formed in a substrate such as a Si substrate. The expression "formed in a substrate" means that the transistors are produced through processing of a substrate such as a Si substrate. Having transistors in a substrate can therefore be thought as having transistors formed integrally with a substrate.

The decision whether to form the transistors in the substrate depends on definition. The transistors can be formed in a Si substrate when, for example, the intended definition is roughly QVGA in a 1-inch size.

FIG. 3 is a schematic view of an image-forming apparatus 26 according to an embodiment. The image-forming apparatus has a photosensitive element, an exposure light source, a development unit, a charging unit, a transfer device, feed rollers, and a fixing device.

The exposure light source 28 emits light 29 to form an electrostatic latent image on the surface of the photosensitive element 27. This exposure light source has an organic light-emitting element according to an embodiment. The development unit 30 has toner or similar. The charging unit 31 charges the photosensitive element. The transfer device 32 transfers the developed image to a recording medium 34. The feed rollers 33 feed the recording medium 34. The recording medium 34 can be, for example, paper. The fixing device 35 fixes the image formed on the recording medium.

Parts (a) and (b) of FIG. 4 are schematic diagrams illustrating exposure light sources 28 each composed of an elongated substrate and multiple light-emitting sections 36 on the substrate. The arrow 37 indicates the direction in which rows of organic light-emitting elements extend. This direction of rows is identical to the direction of the axis around which the photosensitive element 27 rotates. This direction can also be referred to as the longitudinal direction of the photosensitive element.

Part (a) of FIG. 4 illustrates an arrangement in which the light-emitting sections are aligned in the longitudinal direction of the photosensitive element. Part (b) of FIG. 4 presents an arrangement different from that in part (a) of FIG. 4, illustrating an arrangement in which light-emitting sections in a first row and those in a second row alternate in the direction of rows. The first and second rows are located in different positions in the direction of columns.

The first row has multiple spaced light-emitting sections, and the second row has light-emitting sections in the positions corresponding to the spaces between the light-emitting sections in the first row. This means that multiple light-emitting sections are also arranged in the direction of columns with spaces therebetween.

The arrangement illustrated in part (b) of FIG. 4 can be expressed in other words such as latticework, houndstooth, and a checkered pattern.

FIG. 5 is a schematic view of a lighting apparatus according to an embodiment. The lighting apparatus has a substrate, organic light-emitting elements 38, and an AC-DC converter circuit 39. There may be a heat dissipation unit (not illustrated) on, for example, the back of the substrate, i.e., the side opposite where the organic light-emitting elements are placed.

Display apparatuses, lighting apparatuses, and image-forming apparatuses in which an organic light-emitting element according to an embodiment is used therefore offers stable operation for long periods with good quality of images.

EXAMPLES

Example 1

Synthesis of Illustrative Compound A1

(1. Synthesis of Compound E3)

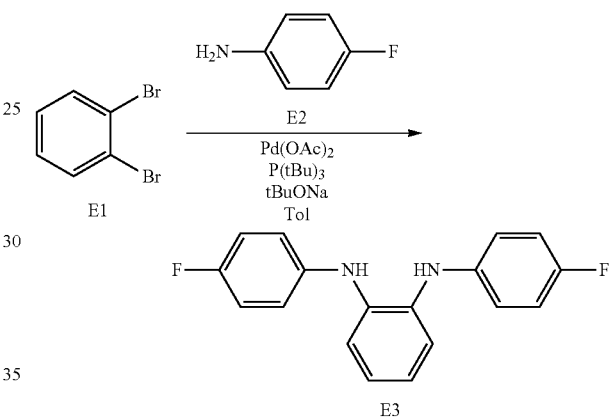

The following reagents and solvent were put into a 100-mL recovery flask.

E1: 2.36 g (10.0 mmol)

E2: 2.33 g (21.0 mmol)

Palladium acetate: 67 mg (0.3 mmol)

Tri-tert-butyl phosphine: 0.17 mL (0.7 mol)

Sodium tert-butoxide: 2.31 g (24.0 mmol)

Toluene: 50 mL

The obtained reaction solution was stirred and heated under reflux for 8 hours. The solution that completed the reaction was combined with water, and the resulting mixture was separated into fractions. Then one of the fractions was purified using silica gel column chromatography (with heptane-chloroform (3:1) as developing solvent), yielding 2.34 g of E3 (79% yield).

(2. Synthesis of Compound E4)

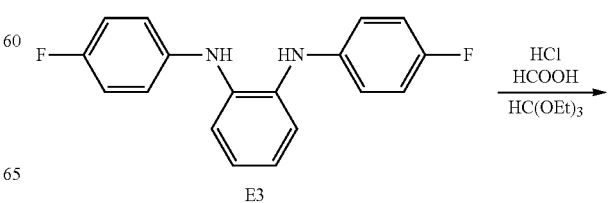

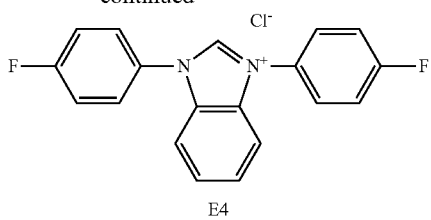

E4

The following reagent and solvent were put into a 100-mL recovery flask.

E3: 1.48 g (5.00 mmol)

Triethyl orthoformate: 25 mL

The obtained solution was stirred for 5 minutes with 0.5 mL of 12 N hydrochloric acid. The solution was then heated at 80° C. for 4 hours with 0.05 mL of formic acid in drops under stirring. After the completion of reaction, triethyl orthoformate was distilled away under reduced pressure. A solution of the residue in chloroform was purified using silica gel column chromatography (with chloroform-methanol (20:1) as developing solvent), yielding 1.20 g of E4 (70% yield).

(3. Synthesis of Illustrative Compound A1)

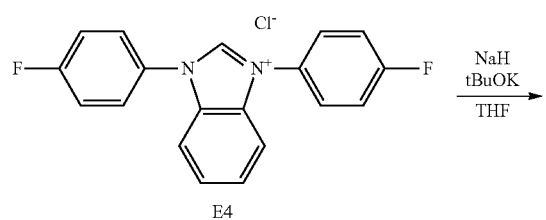

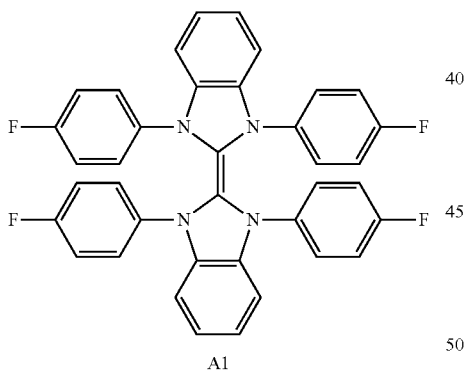

A1

The following reagent and solvent were put into a 100-mL recovery flask under a stream of nitrogen.

E4: 342 mg (11.00 mmol)

Dehydrated THF: 20 mL

The obtained solution was stirred for 2 minutes with 48 mg (2.00 mmol) of sodium hydride. The solution was then heated at 80° C. for 10 hours with 1 mg (0.01 mmol) of tBuOK. A mixture of 20 mL of dehydrated toluene and the solution that completed the reaction was filtered through Celite, the filtrate was concentrated, and the powder residue was washed through dispersion in dehydrated hexane. The resulting mixture was filtered, yielding 160 mg (52% yield) of illustrative compound A1 as a yellow powder.

MALDI-TOF-MS (Matrix-Assisted Laser Desorption/Ionization Time-of-Flight Mass Spectrometry) (Bruker Autoflex LRF)

Measured m/z, 612.38; calculated m/z, 612.19

The CV measurements were performed in a 0.1 M solution of tetrabutylammonium perchlorate in N,N-dimethylformamide using a $Ag/Ag^+$ reference electrode, a Pt counter electrode, and a glassy carbon working electrode. The potential sweep rate was 0.5 V/s.

The oxidation potential measured using ALS 660C Electrochemical Analyzer was −0.85 V.

Example 2

Synthesis of Illustrative Compound A2

Illustrative compound A2 was obtained in the same way as in Example 1, except that compound E2 used in step (1) in Example 1 was changed to compound E5.

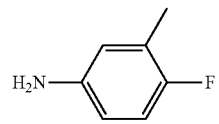

E5

The obtained compound was identified as follows.

<MALDI-TOF-MS (Matrix-Assisted Laser Desorption/Ionization Time-of-Flight Mass Spectrometry) (Bruker Autoflex LRF)>

Measured m/z, 668.66; calculated m/z, 668.26

The oxidation potential measured using ALS 660C Electrochemical Analyzer was −0.87 V.

Example 3

Synthesis of Illustrative Compound A3

Illustrative compound A3 was obtained in the same way as in Example 1, except that compound E2 used in step (1) in Example 1 was changed to compound E6.

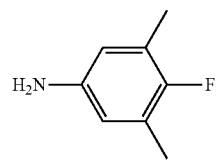

E6

The obtained compound was identified as follows.

<MALDI-TOF-MS (Matrix-Assisted Laser Desorption/Ionization Time-of-Flight Mass Spectrometry) (Bruker Autoflex LRF)>

Measured m/z, 725.11; calculated m/z, 724.32

The oxidation potential measured using ALS 660C Electrochemical Analyzer was −0.89 V.

Example 4

Synthesis of Illustrative Compound A5

Illustrative compound A5 was obtained in the same way as in Example 1, except that compound E2 used in step (1) in Example 1 was changed to compound E7.

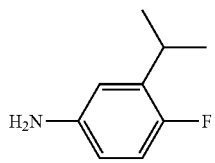

E7

The obtained compound was identified as follows.

<MALDI-TOF-MS (Matrix-Assisted Laser Desorption/Ionization Time-of-Flight Mass Spectrometry) (Bruker Autoflex LRF)>

Measured m/z, 781.22; calculated m/z, 780.38

The oxidation potential measured using ALS 660C Electrochemical Analyzer was −0.87 V.

Example 5

Synthesis of Illustrative Compound A9

Illustrative compound A9 was obtained in the same way as in Example 1, except that compound E2 used in step (1) in Example 1 was changed to compound E8.

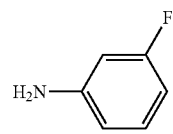

E8

The obtained compound was identified as follows.

<MALDI-TOF-MS (Matrix-Assisted Laser Desorption/Ionization Time-of-Flight Mass Spectrometry) (Bruker Autoflex LRF)>

Measured m/z, 612.77; calculated m/z, 612.19

The oxidation potential measured using ALS 660C Electrochemical Analyzer was −0.73 V.

Example 6

Synthesis of Illustrative Compound A13

Illustrative compound A13 was obtained in the same way as in Example 1, except that compound E2 used in step (1) in Example 1 was changed to compound E9.

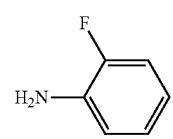

E9

The obtained compound was identified as follows.

<MALDI-TOF-MS (Matrix-Assisted Laser Desorption/Ionization Time-of-Flight Mass Spectrometry) (Bruker Autoflex LRF)>

Measured m/z, 612.82; calculated m/z, 612.19

The oxidation potential measured using ALS 660C Electrochemical Analyzer was −0.84 V.

Example 7

Synthesis of Illustrative Compound A15

Illustrative compound A15 was obtained in the same way as in Example 1, except that compound E2 used in step (1) in Example 1 was changed to compound E10.

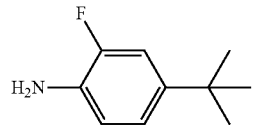

E10

The obtained compound was identified as follows.

<MALDI-TOF-MS (Matrix-Assisted Laser Desorption/Ionization Time-of-Flight Mass Spectrometry) (Bruker Autoflex LRF)>

Measured m/z, 836.98; calculated m/z, 836.44

The oxidation potential measured using ALS 660C Electrochemical Analyzer was −0.89 V.

Example 8

Synthesis of Illustrative Compound A17

Illustrative compound A17 was obtained in the same way as in Example 1, except that compound E1 used in step (1) in Example 1 was changed to compound E11.

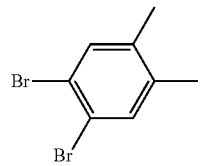

E11

The obtained compound was identified as follows.

<MALDI-TOF-MS (Matrix-Assisted Laser Desorption/Ionization Time-of-Flight Mass Spectrometry) (Bruker Autoflex LRF)>

Measured m/z, 668.98; calculated m/z, 668.26

The oxidation potential measured using ALS 660C Electrochemical Analyzer was −0.93 V.

Example 9

Synthesis of Illustrative Compound A19

Illustrative compound A19 was obtained in the same way as in Example 1, except that compounds E1 and E2 used in step (1) in Example 1 were changed to compounds E12 and E6, respectively.

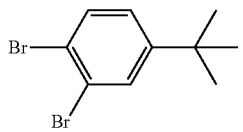

E12

The obtained compound was identified as follows.
<MALDI-TOF-MS (Matrix-Assisted Laser Desorption/Ionization Time-of-Flight Mass Spectrometry) (Bruker Autoflex LRF)>
Measured m/z, 837.11; calculated m/z, 836.44
The oxidation potential measured using ALS 660C Electrochemical Analyzer was −0.93 V.

Example 10

Synthesis of Illustrative Compound A21
Illustrative compound A21 was obtained in the same way as in Example 1, except that compounds E1 and E2 used in step (1) in Example 1 were changed to compounds E11 and E6, respectively.
The obtained compound was identified as follows.
<MALDI-TOF-MS (Matrix-Assisted Laser Desorption/Ionization Time-of-Flight Mass Spectrometry) (Bruker Autoflex LRF)>
Measured m/z, 780.57; calculated m/z, 780.38
The oxidation potential measured using ALS 660C Electrochemical Analyzer was −0.92 V.

Example 11

Synthesis of Illustrative Compound A25
Illustrative compound A25 was obtained in the same way as in Example 1, except that compounds E1 and E2 used in step (1) in Example 1 were changed to compounds E13 and E15, respectively.

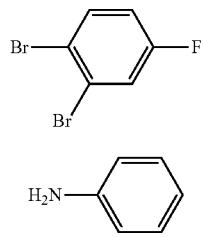

E13

E15

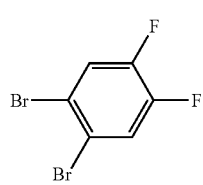

The obtained compound was identified as follows.
<MALDI-TOF-MS (Matrix-Assisted Laser Desorption/Ionization Time-of-Flight Mass Spectrometry) (Bruker Autoflex LRF)>
Measured m/z, 576.88; calculated m/z, 576.21
The oxidation potential measured using ALS 660C Electrochemical Analyzer was −0.84 V.

Example 12

Synthesis of Illustrative Compound A27
Illustrative compound A27 was obtained in the same way as in Example 1, except that compounds E1 and E2 used in step (1) in Example 1 were changed to compounds E14 and E15, respectively.

E14

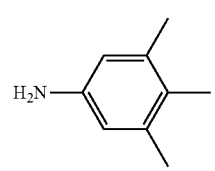

The obtained compound was identified as follows.
<MALDI-TOF-MS (Matrix-Assisted Laser Desorption/Ionization Time-of-Flight Mass Spectrometry) (Bruker Autoflex LRF)>
Measured m/z, 612.99; calculated m/z, 612.19
The oxidation potential measured using ALS 660C Electrochemical Analyzer was −0.77 V.

Example 13

Synthesis of Illustrative Compound A30
Illustrative compound A30 was obtained in the same way as in Example 1, except that compounds E1 and E2 used in step (1) in Example 1 were changed to compounds E13 and E16, respectively.

E16

The obtained compound was identified as follows.
<MALDI-TOF-MS (Matrix-Assisted Laser Desorption/Ionization Time-of-Flight Mass Spectrometry) (Bruker Autoflex LRF)>
Measured m/z, 801.17; calculated m/z, 800.46
The oxidation potential measured using ALS 660C Electrochemical Analyzer was −0.90 V.

Example 14

Synthesis of Illustrative Compound A31
Illustrative compound A31 was obtained in the same way as in Example 1, except that compounds E1 and E2 used in step (1) in Example 1 were changed to compounds E13 and E17, respectively.

E17

The obtained compound was identified as follows.
<MALDI-TOF-MS (Matrix-Assisted Laser Desorption/Ionization Time-of-Flight Mass Spectrometry) (Bruker Autoflex LRF)>
Measured m/z, 744.82; calculated m/z, 744.40
The oxidation potential measured using ALS 660C Electrochemical Analyzer was −0.93 V.

Example 15

Synthesis of Illustrative Compound A34
Illustrative compound A34 was obtained in the same way as in Example 1, except that compounds E1 and E2 used in step (1) in Example 1 were changed to compounds E13 and E6, respectively.

The obtained compound was identified as follows.
<MALDI-TOF-MS (Matrix-Assisted Laser Desorption/Ionization Time-of-Flight Mass Spectrometry) (Bruker Autoflex LRF)>
Measured m/z, 760.45; calculated m/z, 760.30
The oxidation potential measured using ALS 660C Electrochemical Analyzer was −0.89 V.

Example 16

Synthesis of Illustrative Compound A35
Illustrative compound A35 was obtained in the same way as in Example 1, except that compounds E1 and E2 used in step (1) in Example 1 were changed to compounds E13 and E18, respectively.

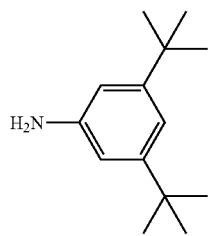

E18

The obtained compound was identified as follows.
<MALDI-TOF-MS (Matrix-Assisted Laser Desorption/Ionization Time-of-Flight Mass Spectrometry) (Bruker Autoflex LRF)>
Measured m/z, 1025.48; calculated m/z, 1024.71
The oxidation potential measured using ALS 660C Electrochemical Analyzer was −0.86 V.

Example 17

Synthesis of Illustrative Compound A36
Illustrative compound A36 was obtained in the same way as in Example 1, except that compounds E1 and E2 used in step (1) in Example 1 were changed to compounds E13 and E19, respectively.

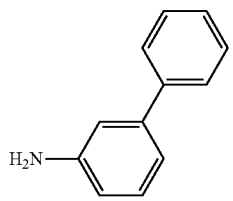

E19

The obtained compound was identified as follows.
<MALDI-TOF-MS (Matrix-Assisted Laser Desorption/Ionization Time-of-Flight Mass Spectrometry) (Bruker Autoflex LRF)>
Measured m/z, 880.87; calculated m/z, 880.34
The oxidation potential measured using ALS 660C Electrochemical Analyzer was −0.86 V.

Example 18

Synthesis of Illustrative Compound B1
Illustrative compound B1 was obtained in the same way as in Example 1, except that compound E2 used in step (1) in Example 1 was changed to compound E16.

The obtained compound was identified as follows.
<MALDI-TOF-MS (Matrix-Assisted Laser Desorption/Ionization Time-of-Flight Mass Spectrometry) (Bruker Autoflex LRF)>
Measured m/z, 746.90; calculated m/z, 746.48
The oxidation potential measured using ALS 660C Electrochemical Analyzer was −0.96 V.

Example 19

Synthesis of Illustrative Compound B2
Illustrative compound B2 was obtained in the same way as in Example 1, except that compound E2 used in step (1) in Example 1 was changed to compound E18.
The obtained compound was identified as follows.
<MALDI-TOF-MS (Matrix-Assisted Laser Desorption/Ionization Time-of-Flight Mass Spectrometry) (Bruker Autoflex LRF)>
Measured m/z, 989.65; calculated m/z, 988.73

Example 20

Synthesis of Illustrative Compound B3
Illustrative compound B3 was obtained in the same way as in Example 1, except that compounds E1 and E2 used in step (1) in Example 1 were changed to compounds E12 and E15, respectively.
The obtained compound was identified as follows.
<MALDI-TOF-MS (Matrix-Assisted Laser Desorption/Ionization Time-of-Flight Mass Spectrometry) (Bruker Autoflex LRF)>
Measured m/z, 652.94; calculated m/z, 652.36
The oxidation potential measured using ALS 660C Electrochemical Analyzer was −0.95 V.

Example 21

Synthesis of Illustrative Compound B7
Illustrative compound B7 was obtained in the same way as in Example 1, except that compounds E1 and E2 used in step (1) in Example 1 were changed to compounds E12 and E16, respectively.
The obtained compound was identified as follows.
<MALDI-TOF-MS (Matrix-Assisted Laser Desorption/Ionization Time-of-Flight Mass Spectrometry) (Bruker Autoflex LRF)>
Measured m/z, 877.22; calculated m/z, 876.61
The oxidation potential measured using ALS 660C Electrochemical Analyzer was −0.99 V.

Example 22

Synthesis of Illustrative Compound B8
Illustrative compound B8 was obtained in the same way as in Example 1, except that compounds E1 and E2 used in step (1) in Example 1 were changed to compounds E11 and E16, respectively.
The obtained compound was identified as follows.
<MALDI-TOF-MS (Matrix-Assisted Laser Desorption/Ionization Time-of-Flight Mass Spectrometry) (Bruker Autoflex LRF)>
Measured m/z, 820.73; calculated m/z, 820.54
The oxidation potential measured using ALS 660C Electrochemical Analyzer was −1.03 V.

Example 23

Synthesis of Illustrative Compound B9

Illustrative compound B9 was obtained in the same way as in Example 1, except that compounds 1 and E2 used in step (1) in Example 1 were changed to compounds E11 and E18, respectively.

The obtained compound was identified as follows.
<MALDI-TOF-MS (Matrix-Assisted Laser Desorption/Ionization Time-of-Flight Mass Spectrometry) (Bruker Autoflex LRF)>

Measured m/z, 1045.11; calculated m/z, 1044.79

Example 24

Synthesis of Illustrative Compound B14

Illustrative compound B14 was obtained in the same way as in Example 1, except that compounds E1 and E2 used in step (1) in Example 1 were changed to compounds E11 and E20, respectively,

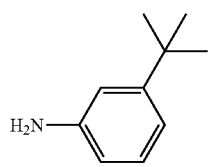

E20

The obtained compound was identified as follows.
<MALDI-TOF-MS (Matrix-Assisted Laser Desorption/Ionization Time-of-Flight Mass Spectrometry) (Bruker Autoflex LRF)>

Measured m/z, 1101.10; calculated m/z, 1100.86

Example 25

Synthesis of Illustrative Compound B17

Illustrative compound B17 was obtained in the same way as in Example 1, except that compounds E1 and E2 used in step (1) in Example 1 were changed to compounds E21 and E22, respectively.

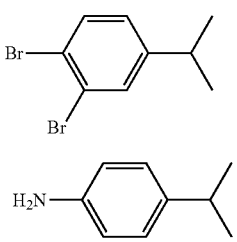

The obtained compound was identified as follows.
<MALDI-TOF-MS (Matrix-Assisted Laser Desorption/Ionization Time-of-Flight Mass Spectrometry) (Bruker Autoflex LRF)>

Measured m/z, 792,88; calculated m/z, 792.51

The oxidation potential measured using ALS 660C Electrochemical Analyzer was −0.99 V.

Example 26

Synthesis of Illustrative Compound B19

Illustrative compound B19 was obtained in the same way as in Example 1, except that compounds E1 and E2 used in step (1) in Example 1 were changed to compounds E12 and E23, respectively.

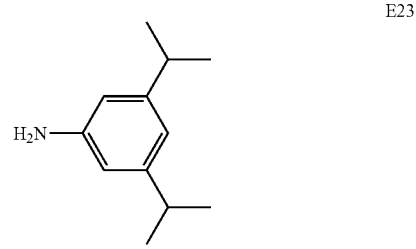

E23

The obtained compound was identified as follows.
<MALDI-TOF-MS (Matrix-Assisted Laser Desorption/Ionization Time-of-Flight Mass Spectrometry) (Bruker Autoflex LRF)>

Measured m/z, 988.46; calculated m/z, 988.73

The oxidation potential measured using ALS 660C Electrochemical Analyzer was −0.96 V.

Example 27

Synthesis of Illustrative Compound B23

Illustrative compound B23 was obtained in the same way as in Example 1, except that compounds E1 and E2 used in step (1) in Example 1 were changed to compounds E24 and E16, respectively.

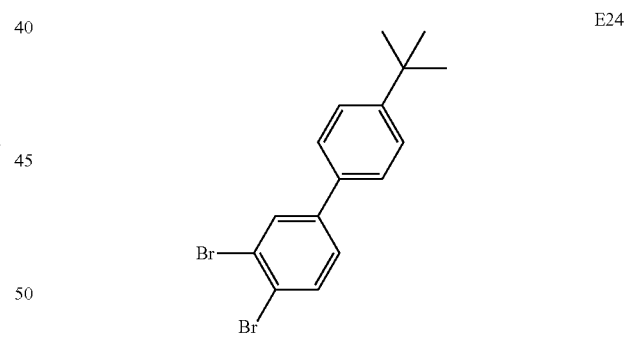

E24

The obtained compound was identified as follows.
<MALDI-TOF-MS (Matrix-Assisted Laser Desorption/Ionization Time-of-Flight Mass Spectrometry) (Bruker Autoflex LRF)>

Measured m/z, 1028.96; calculated m/z, 1028.67

Example 28

Synthesis of Illustrative Compound B25

Illustrative compound B25 was obtained in the same way as in Example 1, except that compounds E1 and E2 used in step (1) in Example 1 were changed to compounds E11 and E22 respectively.

The obtained compound was identified as follows.
<MALDI-TOF-MS (Matrix-Assisted Laser Desorption/ Ionization Time-of-Flight Mass Spectrometry) (Bruker Autoflex LRF)>
Measured m/z, 764.88; calculated m/z, 764.48

Example 29

Synthesis of Illustrative Compound B29

Illustrative compound B29 was obtained in the same way as in Example 1, except that compounds E1 and E2 used in step (1) in Example 1 were changed to compounds E12 and E22 respectively.

The obtained compound was identified as follows.
<MALDI-TOF-MS (Matrix-Assisted Laser Desorption/ Ionization Time-of-Flight Mass Spectrometry) (Bruker Autoflex LRF)>
Measured m/z, 820.12; calculated m/z, 820.54

Example 30

Synthesis of Illustrative Compound B41

Illustrative compound B41 was obtained in the same way as in Example 1, except that compounds E1 and E2 used in step (1) in Example 1 were changed to compounds E11 and E25, respectively.

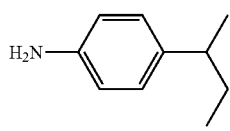

E25

The obtained compound was identified as follows.
<MALDI-TOF-MS (Matrix-Assisted Laser Desorption/ Ionization Time-of-Flight Mass Spectrometry) (Bruker Autoflex LRF)>
Measured m/z, 820.01; calculated m/z, 820.54

Example 31

Synthesis of Illustrative Compound B48

Illustrative compound B48 was obtained in the same way as in Example 1, except that compounds E1 and E2 used in step (1) in Example 1 were changed to compounds E11 and E26, respectively.

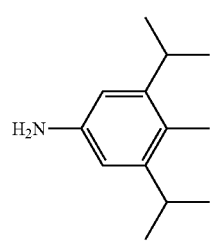

E26

The obtained compound was identified as follows.
<MALDI-TOF-MS (Matrix-Assisted Laser Desorption/ Ionization Time-of-Flight Mass Spectrometry) (Bruker Autoflex LRF)>
Measured m/z, 988.33; calculated m/z, 988.73

Examples 32 to 35 and Comparative Examples 1 and 2

In these examples, organic light-emitting elements were prepared each composed of a substrate and an anode, a hole transport layer, an electron blocking layer, an emitting layer, a hole blocking layer, an electron transport layer, an electron injection layer, and a cathode formed in this order on the substrate.

First, an ITO film on a glass substrate was processed into an intended pattern to form an ITO electrode (the anode). The thickness of the ITO electrode was 100 nm. This substrate having an ITO electrode formed thereon, hereinafter referred to as the ITO substrate, was used in the following process.

The organic compound and electrode layers indicated in Table 2 were then formed sequentially on the ITO substrate. The area of the opposing electrode (the metallic electrode layer as cathode) was 3 mm$^2$.

TABLE 2

|  | Materials | Thickness (nm) |
|---|---|---|
| Hole transport layer | G1 | 30 |
| Electron blocking layer | G2 | 10 |
| Emitting layer | G3 (host) | 30 |
|  | G4 (guest) |  |
|  | (G3:G4 = 98:2 (weight ratio)) |  |
| Hole blocking layer | G5 | 10 |
| Electron transport layer | G6 | 15 |
| Electron injection layer | G7 | 15 |
|  | G8 |  |
|  | (G7:G8 = 50:50 (weight ratio)) |  |
| Metallic electrode layer | Al | 100 |

Prior to the formation of the metallic electrode layer, the workpiece was left in the air for 10 minutes.

Compounds G1 to G7 were as summarized in Table 3, and G8 was selected from 1,1',3,3'-tetraphenyl-2,2'-bibenzo[d] imidazolidene compounds according to an embodiment and comparative compounds 3 and 4. The obtained organic light-emitting elements were tested.

TABLE 3

|  | G1 | G2 | G3 | G4 | G5 | G6 | G7 | G8 | Light emission |
|---|---|---|---|---|---|---|---|---|---|
| Example 32 | HT1 | HT7 | EM13 | RD1 | ET2 | ET2 | EI6 | A1 | ○ |
| Example 33 | HT1 | HT7 | EM13 | RD1 | ET2 | ET2 | EI6 | A3 | ○ |
| Example 34 | HT1 | HT7 | EM13 | RD1 | ET2 | ET2 | EI6 | B2 | ○ |

TABLE 3-continued

|  | G1 | G2 | G3 | G4 | G5 | G6 | G7 | G8 | Light emission |
|---|---|---|---|---|---|---|---|---|---|
| Example 35 | HT1 | HT7 | EM13 | RD1 | ET2 | ET2 | EI6 | B7 | ○ |
| Comparative Example 1 | HT1 | HT7 | EM13 | RD1 | ET2 | ET2 | EI6 | Comparative compound 3 | X |
| Comparative Example 2 | HT1 | HT7 | EM13 | RD1 | ET2 | ET2 | EI6 | Comparative compound 4 | X |

Light emission under a voltage of 8 V was observed with compounds according to an embodiment, but not with comparative compounds 3 and 4.

This should be because the comparative compounds were denatured and lost their electron injection properties upon exposure to the air.

Examples 36 to 45

Organic light-emitting elements were prepared each composed of a substrate and an anode, a hole transport layer, an electron blocking layer, an emitting layer, a hole blocking layer, an electron transport layer, an electron injection layer, and a cathode formed in this order on the substrate.

First, an ITO film on a glass substrate was processed into an intended pattern to form an ITO electrode (the anode). The thickness of the ITO electrode was 100 nm. This substrate having an ITO electrode formed thereon, hereinafter referred to as the ITO substrate, was used in the following process.

The organic compound and electrode layers indicated in Table 4 were then formed sequentially on the ITO substrate. The area of the opposing electrode (the metallic electrode layer as cathode) was 3 mm$^2$.

TABLE 4

|  | Materials | Thickness (nm) |
|---|---|---|
| Hole transport layer | G1 | 30 |
| Electron blocking layer | G2 | 10 |
| Emitting layer | G3 (host) | 30 |
|  | G4 (guest) |  |
|  | (G3:G4 = 98:2 (weight ratio)) |  |
| Hole blocking layer | G5 | 10 |
| Electron transport layer | G6 | 15 |
| Electron injection layer | G7 | 15 |
|  | G8 |  |
|  | (G7:G8 = 50:50 (weight ratio)) |  |
| Metallic electrode layer | Al | 100 |

Compounds G1 to G7 were as summarized in Table 5, and G8 was selected from 1,1',3,3'-tetraphenyl-2,2'-bibenzo[d]imidazolidene compounds according to an embodiment. The obtained organic light-emitting elements were tested.

TABLE 5

|  | G1 | G2 | G3 | G4 | G5 | G6 | G7 | G8 | Emission efficiency (cd/A) | Voltage (V) |
|---|---|---|---|---|---|---|---|---|---|---|
| Example 36 | HT1 | HT7 | EM3 | BD1 | ET2 | ET2 | EI6 | A1 | 3 | 8 |
| Example 37 | HT1 | HT7 | EM4 | BD7 | EM16 | EM16 | EI7 | A3 | 3 | 7 |
| Example 38 | HT2 | HT8 | EM12 | RD1 | ET4 | ET3 | EI6 | A15 | 4 | 6 |
| Example 39 | HT2 | HT6 | EM7 | RD4 | ET5 | ET3 | EI5 | A31 | 7 | 7 |
| Example 40 | HT2 | HT7 | EM1 | BD4 | EM16 | EM15 | EI8 | B1 | 3 | 6 |
| Example 41 | HT6 | HT7 | EM5 | GD1 | ET4 | ET3 | EI7 | B2 | 15 | 7 |
| Example 42 | HT6 | HT7 | EM8 | GD4 | EM15 | ET3 | EI6 | B6 | 12 | 6 |
| Example 43 | HT6 | HT7 | EM11 | RD2 | EM15 | EM15 | EI8 | B6 | 3 | 6 |
| Example 44 | HT2 | HT7 | EM3 | BD6 | ET4 | ET2 | EI6 | B8 | 3 | 7 |
| Example 45 | HT6 | HT7 | EM13 | RD1 | ET10 | ET2 | EI7 | B14 | 5 | 6 |

Examples 46 to 51

Organic light-emitting elements were prepared each composed of a substrate and an anode, a hole transport layer, an electron blocking layer, an emitting layer, a hole blocking layer, an electron transport layer, an electron injection layer, and a metallic electrode layer (cathode) formed in this order on the substrate.

First, an ITO film on a glass substrate was processed into an intended pattern to form an ITO electrode (the anode). The thickness of the ITO electrode was 100 nm. This substrate having an ITO electrode formed thereon, hereinafter referred to as the ITO substrate, was used in the following process.

The organic compound and electrode layers indicated in Table 6 were then formed on the ITO substrate. The area of the opposing electrode (the metallic electrode layer as cathode) was 3 mm$^2$.

TABLE 6

|  | Materials | Thickness (nm) |
|---|---|---|
| Hole transport layer | G1 | 30 |
| Electron blocking layer | G2 | 10 |
| Emitting layer | G3 (host) | 30 |
|  | G4 (guest) |  |
|  | (G3:G4 = 98:2 (weight ratio)) |  |
| Hole blocking layer | G5 | 10 |
| Electron transport layer | G6 | 25 |
| Electron injection layer | G8 | 5 |
| Metallic electrode layer | Al | 100 |

Compounds G1 to G6 were as summarized in Table 7, and G8 was selected from 1,1',3,3'-tetraphenyl-2,2'-bibenzo[d]imidazolidene compounds according to an embodiment. The obtained organic light-emitting elements were tested.

TABLE 7

| | G1 | G2 | G3 | G4 | G5 | G6 | G8 | Emission efficiency (cd/A) | Voltage (V) |
|---|---|---|---|---|---|---|---|---|---|
| Example 46 | HT1 | HT7 | EM13 | RD1 | ET2 | EI6 | A19 | 5 | 7 |
| Example 47 | HT2 | HT7 | EM4 | BD7 | EM15 | EI6 | A20 | 3 | 10 |
| Example 48 | HT2 | HT7 | EM14 | RD2 | EM17 | EI7 | A21 | 6 | 7 |
| Example 49 | HT2 | HT7 | EM15 | RD1 | EM15 | EI8 | B8 | 4 | 6 |
| Example 50 | HT2 | HT7 | EM16 | GD4 | EM16 | EI8 | B9 | 12 | 9 |
| Example 51 | HT2 | HT7 | EM17 | RD4 | EM14 | EI6 | B17 | 4 | 7 |

Example 52

Synthesis of Illustrative Compound C5

(1. Synthesis of Compound E27)

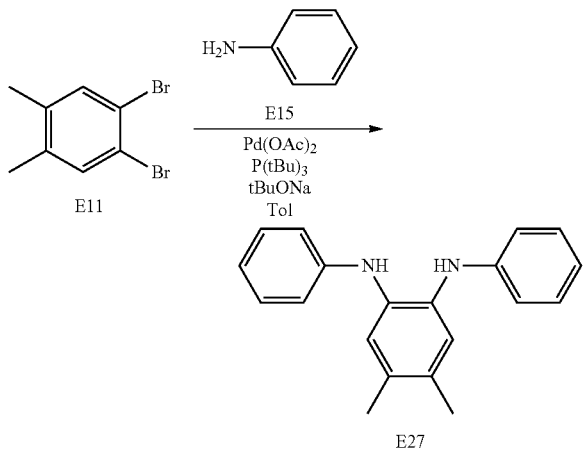

The following reagents and solvent were put into a 100-mL recovery flask.

E11: 2.64 g (10.0 mmol)
E15: 1.96 g (21.0 mmol)
Palladium acetate: 67 mg (0.3 mmol)
Tri-tert-butyl phosphine: 0.17 mL (0.7 mol)
Sodium tert-butoxide: 2.31 g (24.0 mmol)
Toluene: 50 mL The obtained reaction solution was stirred and heated under reflux for 8 hours. The solution that completed the reaction was filtered through Celite, and the filtered solution was combined with water. The resulting mixture was separated into fractions, and one of the fractions was purified using silica gel column chromatography (with heptane-chloroform (3:1 to 2:1) as developing solvent), yielding 2.45 g of E27 (85% yield).

(2. Synthesis of Compound E28)

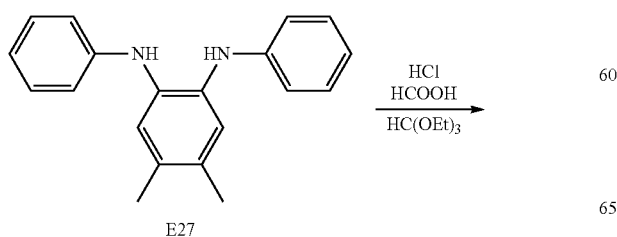

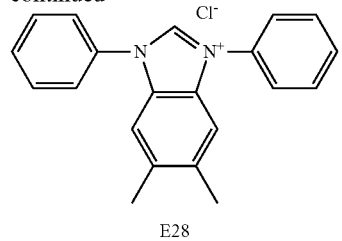

The following reagent and solvent were put into a 100-mL recovery flask.

E27: 1.44 g (5.00 mmol)
Triethyl orthoformate: 50 mL

The obtained solution was stirred for 5 minutes with 0.8 mL of 12 N hydrochloric acid. The solution was then heated at 80° C. for 4 hours with 0.05 mL of formic acid in drops under stirring. The solution that completed the reaction was allowed to cool and combined with 20 mL of diethyl ether. The crystals that separated out were collected through filtration and washed with diethyl ether. The crystals were then dried under reduced pressure at 120° C., yielding 1.60 g of E28 (95% yield).

(3. Synthesis of Illustrative Compound C5)

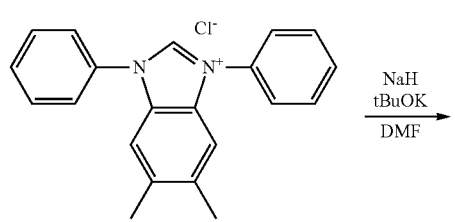

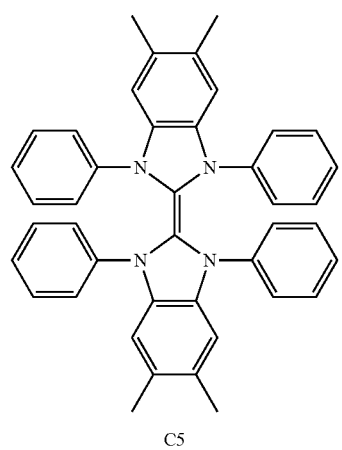

The following reagent and solvent were put into a 100-mL recovery flask under a stream of nitrogen.

E28: 335 mg (1.00 mmol)

Dehydrated DMF: 5 mL

The obtained solution was degassed with nitrogen and stirred for 2 minutes with 96 mg (4.00 mmol) of sodium hydride. The solution was then heated at 30° C. for 24 hours with 22 mg (0.2 mmol) of tBuOK. To the solution that completed the reaction, 10 mL of nitrogen-degassed water was gradually added under stirring. The solvent was removed using a syringe after the intended product separated out. After two cycles of adding 10 mL of nitrogen-degassed water and removing solvent using a syringe, the residue was washed through dispersion in 10 mL of degassed hexane using ultra-sonication. The resulting mixture was passed through a membrane filter. The residue was washed with hexane, yielding 241 mg (72% yield) of illustrative compound C5 as a yellow powder.

<MALDI-TOF-MS (Matrix-Assisted Laser Desorption/ Ionization Time-of-Flight Mass Spectrometry) (Bruker Autoflex LRF)>

Measured m/z, 596.55; calculated m/z, 596.29

The CV measurements were performed in a 0.1 M solution of tetrabutylammonium perchlorate in N,N-dimethylformamide using a Ag/Ag$^+$ reference electrode, a Pt counter electrode, and a glassy carbon working electrode. The potential sweep rate was −0.5 V/s.

The oxidation potential measured using ALS 660C Electrochemical Analyzer was −0.99 V.

Example 53

Synthesis of Illustrative Compound C8

Illustrative compound C8 was obtained in the same way as in Example 52, except that compound E15 used in step (1) in Example 52 was changed to compound E29.

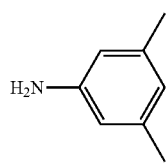

E29

The obtained compound was identified as follows.

<MALDI-TOF-MS (Matrix-Assisted Laser Desorption/ Ionization Time-of-Flight Mass Spectrometry) (Bruker Autoflex LRF)>

Measured m/z, 708.22; calculated m/z, 708.42

The oxidation potential measured using ALS 660C Electrochemical Analyzer was −1.05 V.

Example 54

Synthesis of Illustrative Compound C10

Illustrative compound C10 was obtained in the same way as in Example 52, except that compound E15 used in step (1) in Example 52 was changed to compound E17.

The obtained compound was identified as follows.

<MALDI-TOF-MS (Matrix-Assisted Laser Desorption/ Ionization Time-of-Flight Mass Spectrometry) (Bruker Autoflex LRF)>

Measured m/z, 764.83; calculated m/z, 764.48

The oxidation potential measured using ALS 660C Electrochemical Analyzer was −1.05 V.

Example 55

Synthesis of Illustrative Compound C14
Synthesis of Compound E32

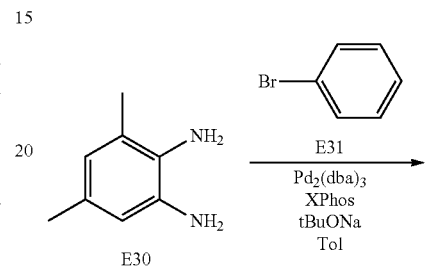

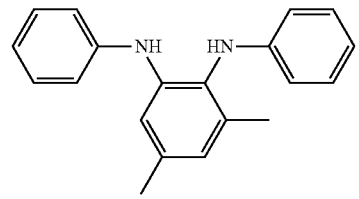

E32

The following reagents and solvent were put into a 100-mL recovery flask.

E30: 1.36 g (10.0 mmol)

E31: 2.75 g (22.0 mmol)

Tris(dibenzylideneacetone)dipalladium: 183 mg (0.2 mmol)

2-Dicyclohexylphosphino-2',4',6'-triisopropylbiphenyl: 380 mg (0.8 mmol)

Sodium tert-butoxide: 2.31 g (24.0 mmol)

Toluene: 50 mL

The obtained reaction solution was stirred and heated under reflux for 8 hours. The solution that completed the reaction was filtered through Celite, and the filtered solution was combined with water. The resulting mixture was separated into fractions, and one of the fractions was purified using silica gel column chromatography (with heptane-chloroform (3:1 to 2:1) as developing solvent), yielding 1.73 g of E32 (60% yield).

Illustrative compound C14 was then obtained by performing subsequent reactions in the same way as in Example 52.

The obtained compound was identified as follows.
<MALDI-TOF-MS (Matrix-Assisted Laser Desorption/Ionization Time-of-Flight Mass Spectrometry) (Bruker Autoflex LRF)>
Measured m/z, 596.68; calculated m/z, 596.29
The oxidation potential measured using ALS 660C Electrochemical Analyzer was −0.91 V.

Examples 56 to 71

Organic light-emitting elements were prepared each composed of a substrate and an anode, a hole transport layer, an electron blocking layer, an emitting layer, a hole blocking layer, an electron transport layer, an electron injection layer, and a cathode formed in this order on the substrate.

First, an ITO film on a glass substrate was processed into an intended pattern to form an ITO electrode (the anode). The thickness of the ITO electrode was 100 nm. This substrate having an ITO electrode formed thereon, hereinafter referred to as the ITO substrate, was used in the following process.

The organic compound and electrode layers indicated in Table 8 were then formed sequentially on the ITO substrate. The area of the opposing electrode (the metallic electrode layer as cathode) was 3 mm$^2$.

TABLE 8

|  | Materials | Thickness (nm) |
| --- | --- | --- |
| Hole transport layer | G1 | 30 |
| Electron blocking layer | G2 | 10 |
| Emitting layer | G3 (host) | 30 |
|  | G4 (guest) |  |
|  | (G3:G4 = 98:2 (weigh ratio)) |  |
| Hole blocking layer | G5 | 10 |
| Electron transport layer | G6 | 26 |
| Electron injection layer | G8 | 4 |
| Metallic electrode layer | G9 | 100 |

Compounds G1 to G6 were as summarized Table 9, and G9 was the metal indicated in Table 9. Any mixture of metals was in the indicated weight ratio. G8 was selected from organic compounds according to an embodiment. The obtained organic light-emitting elements were tested.

Examples 72 to 79

Organic light-emitting elements were prepared each composed of a substrate and an anode, a hole transport layer, an electron blocking layer, an emitting layer, a hole blocking layer, an electron transport layer, an electron injection layer, and a cathode formed in this order on the substrate. Compound D2 was always controlled under nitrogen until vapor deposition.

First, an ITO film on a glass substrate was processed into an intended pattern to form an ITO electrode (the anode). The thickness of the ITO electrode was 100 nm. This substrate having an ITO electrode formed thereon, hereinafter referred to as the ITO substrate, was used in the following process.

The organic compound and electrode layers indicated in Table 10 were then formed sequentially on the ITO substrate. The area of the opposing electrode (the metallic electrode layers as cathode) was 3 mm$^2$.

TABLE 10

|  | Materials | Thickness (nm) |
| --- | --- | --- |
| Hole transport layer | G1 | 30 |
| Electron blocking layer | G2 | 10 |
| Emitting layer | G3 (host) | 30 |
|  | G4 (guest) |  |
|  | (G3:G4 = 98:2 (weight ratio)) |  |
| Hole blocking layer | G5 | 10 |
| Electron transport layer | G6 | 26 |
| Electron injection layer | G8 | 4 |
| Metallic electrode layers | G9 | 100 |
|  | G10 | 100 |

Compounds G1 to G6 were as summarized in Table 11, and G9 and G10 were the metals indicated in Table 11. Any mixture of metals was in the indicated weight ratio. G8 was selected from organic compounds according to an embodiment. The obtained organic light-emitting elements were tested.

TABLE 9

|  | G1 | G2 | G3 | G4 | G5 | G6 | G8 | G9 | Emission efficiency (cd/A) | Voltage (V) |
| --- | --- | --- | --- | --- | --- | --- | --- | --- | --- | --- |
| Example 56 | HT1 | HT7 | EM13 | RD1 | ET2 | EI8 | A21 | Ag | 4 | 6 |
| Example 57 | HT2 | HT7 | EM4 | BD7 | ET6 | EI14 | B1 | Ag | 4 | 5 |
| Example 58 | HT2 | HT7 | EM1 | GD4 | EM17 | EI19 | B9 | Au | 19 | 6 |
| Example 59 | HT2 | HT7 | EM4 | BD4 | ET5 | EI17 | B25 | Ag:Mg = 1:1 | 6 | 5 |
| Example 60 | HT2 | HT7 | EM14 | RD2 | EI16 | EI16 | B25 | Ag | 6 | 5 |
| Example 61 | HT6 | HT7 | EM13 | RD1 | EI17 | EI9 | C5 | Al | 5 | 5 |
| Example 62 | HT6 | HT7 | EM13 | RD1 | EI17 | EI9 | C5 | Ag | 5 | 5 |
| Example 63 | HT6 | HT7 | EM13 | RD1 | EI17 | EI9 | C5 | Au | 5 | 5 |
| Example 64 | HT6 | HT7 | EM13 | RD1 | EI17 | EI9 | C5 | Ag:Mg = 1:1 | 5 | 5 |
| Example 65 | HT6 | HT7 | EM7 | GD7 | EM15 | EI14 | C7 | Ag | 25 | 6 |
| Example 66 | HT6 | HT7 | EM9 | RD3 | EM15 | EI13 | C7 | Ag:Mg = 2:1 | 10 | 5 |
| Example 67 | HT6 | HT7 | EM4 | BD6 | ET6 | EI12 | C8 | Ag | 5 | 7 |
| Example 68 | HT6 | HT7 | EM12 | RD2 | EI16 | EI6 | C8 | Au | 5 | 5 |
| Example 69 | HT6 | HT7 | EM9 | RD7 | EI13 | EI19 | C10 | Ag | 8 | 7 |
| Example 70 | HT6 | HT7 | EM4 | BD7 | EI14 | EI14 | C14 | Au | 6 | 5 |
| Example 71 | HT6 | HT7 | EM1 | GD4 | ET5 | EI16 | C19 | Ag:Cu = 5:1 | 15 | 6 |

TABLE 11

|  | G1 | G2 | G3 | G4 | G5 | G6 | G8 | G9 | G10 | Emission efficiency (cd/A) | Voltage (V) |
|---|---|---|---|---|---|---|---|---|---|---|---|
| Example 72 | HT1 | HT7 | EM13 | RD1 | ET2 | EI8 | B2 | Ag | Ag:Mg = 1:1 | 4 | 5 |
| Example 73 | HT2 | HT7 | EM4 | BD7 | ET6 | EI14 | B9 | Ag | Ag:Cu = 4:1 | 4 | 5 |
| Example 74 | HT2 | HT7 | EM14 | RD2 | EI16 | EI16 | B25 | Ag | Ag:Mg = 1:1 | 6 | 5 |
| Example 75 | HT6 | HT7 | EM13 | RD1 | EI17 | EI9 | C5 | Ag:Mg = 1:1 | Cu | 5 | 5 |
| Example 76 | HT2 | HT7 | EM14 | RD2 | EI16 | EI16 | C8 | Ag | Cu | 5 | 5 |
| Example 77 | HT6 | HT7 | EM13 | RD1 | EI17 | EI9 | C8 | Al | Ag:Bi = 99:1 | 5 | 5 |
| Example 78 | HT6 | HT7 | EM4 | BD7 | EI14 | EI14 | D1 | Ag | Ag:Mg = 1:1 | 6 | 5 |
| Example 79 | HT2 | HT7 | EM1 | GD4 | EM17 | EI19 | D2 | Au | Al | 19 | 6 |

As can be seen from the Examples, the use of an organic compound according to an embodiment in an electron injection layer of a light-emitting element makes the element insusceptible to oxygen and, therefore, stable and long-lived.

INDUSTRIAL APPLICABILITY

As the foregoing demonstrates, organic light-emitting elements according to an aspect of the invention, having an electron injection layer which contains a 1,1',3,3'-tetraphenyl-2,2'-bibenzo[d]imidazolidene compound, are resistant to water and humidity. An aspect of the invention therefore provides organic light-emitting elements with high emission efficiency and good lifetime properties.

An aspect of the invention, furthermore, provides a 1,1',3,3'-tetraphenyl-2,2'-bibenzo[d]imidazolidene compound insusceptible to oxidation in the air.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An organic light-emitting element comprising:
an anode;
a cathode;
an emitting layer between the anode and the cathode; and
an organic compound layer between the cathode and the emitting layer,
the organic compound layer containing a compound represented by general formula (2):

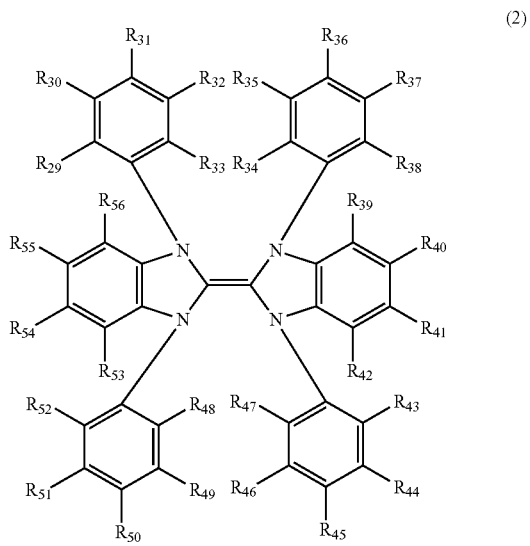

where $R_{29}$ to $R_{56}$ are each independently selected from a hydrogen atom and a substituent, the substituent being any of a halogen atom, an alkyl group containing 1 or more and 8 or less carbon atoms, and a substituted or unsubstituted aryl group.

2. The organic light-emitting element according to claim 1, wherein at least one of the $R_{29}$ to the $R_{56}$ is the substituent.

3. The organic light-emitting element according to claim 1, wherein at least one of the $R_{39}$ to the $R_{42}$ and the $R_{53}$ to the $R_{56}$ is any of an alkyl group containing 1 or more and 8 or less carbon atoms and a phenyl group.

4. The organic light-emitting element according to claim 1, wherein each of the $R_{40}$, the $R_{41}$, the $R_{54}$, and the $R_{55}$ is an alkyl group containing 1 or more and 8 or less carbon atoms or a phenyl group.

5. The organic light-emitting element according to claim 1, wherein at least one of the $R_{29}$ to the $R_{38}$ and the $R_{43}$ to the $R_{52}$ is any of a fluorine atom, a tert-butyl group, a sec-butyl group, an isobutyl group, and an isopropyl group with the $R_{39}$ to the $R_{42}$ and the $R_{53}$ to the $R_{56}$ being hydrogen atoms.

6. The organic light-emitting element according to claim 1, wherein the organic compound layer contains an additional compound of a kind different from the organic compound,
wherein the additional compound is any of an anthraquinone derivative, a fluorene derivative, a naphthalene derivative, an indene derivative, a terphenyl derivative, an acenaphthofluoranthene derivative, an indenoperylene derivative, and a phenanthroline derivative.

7. The organic light-emitting element according to claim 1, further comprising a second emitting layer configured to emit light in a color different from a color of light emitted by the emitting layer, wherein:
the element emits white light as a result of blending of the color of the light emitted by the emitting layer with the color of the light emitted by the second emitting layer.

8. The organic light-emitting element according claim 1, further comprising a color filter.

9. A display apparatus comprising:
a plurality of emitting points,
at least one of the plurality of emitting points having an organic light-emitting element according to claim 1 and an active element coupled to the organic light-emitting element.

10. The display apparatus according to claim 9, wherein:
the active element is a transistor,
the transistor having an oxide semiconductor in an active layer thereof.

11. An image information-processing apparatus comprising:
a display unit configured to display an image;
an input unit configured to receive image information; and
an information-processing unit configured to process the image information,
the display unit being a display apparatus according to claim 9.

12. A lighting apparatus comprising:
an organic light-emitting element according to claim 1; and
an AC-DC converter coupled to the organic light-emitting element.

13. A lighting apparatus comprising:
an organic light-emitting element according to claim 1; and
a heat dissipation unit configured to dissipate heat out of the apparatus.

14. An image-forming apparatus comprising:
a photosensitive element;
a charging unit configured to charge a surface of the photosensitive element;
an exposure unit configured to expose the photosensitive element; and
a development unit configured to apply a developer to the surface of the photosensitive element,
the exposure unit having an organic light-emitting element according to claim 1.

15. An exposure apparatus configured to expose a photosensitive element, the exposure apparatus comprising:
a plurality of organic light-emitting elements according to claim 1,
the plurality of organic light-emitting elements arranged in a line in a longitudinal direction of the photosensitive element.

16. The organic light-emitting element according to claim 6, wherein the additional compound has a higher oxidation potential than the organic compound.

17. The organic light-emitting element according to claim 6, wherein the additional compound is any of an anthraquinone derivative, a fluorene derivative, a naphthalene derivative, an indene derivative, a terphenyl derivative, an acenaphthofluoranthene derivative, an indenoperylene derivative, and a phenanthroline derivative.

18. The organic light-emitting element according to claim 1, wherein:
the emitting layer contains a plurality of emitting materials;
at least one of the plurality of emitting materials emits light in a color different from a color of light emitted by another; and
the emitting layer emits white light.

* * * * *